(12) United States Patent
Iuchi et al.

(10) Patent No.: US 7,482,509 B2
(45) Date of Patent: Jan. 27, 2009

(54) TRANSGENIC PLANTS CARRYING NEOXANTHIN CLEAVAGE ENZYME GENE

(75) Inventors: Satoshi Iuchi, Tsukuba (JP); Masatomo Kobayashi, Tsukuba (JP); Kazuo Shinozaki, Tsukuba (JP)

(73) Assignee: Riken, Saitama (JP)

( * ) Notice: Subject to any disclaimer, the term of this patent is extended or adjusted under 35 U.S.C. 154(b) by 22 days.

(21) Appl. No.: 11/385,832

(22) Filed: Mar. 22, 2006

(65) Prior Publication Data

US 2006/0212969 A1    Sep. 21, 2006

Related U.S. Application Data

(62) Division of application No. 09/758,269, filed on Jan. 12, 2001, now Pat. No. 7,049,487.

(30) Foreign Application Priority Data

Jan. 13, 2000  (JP) ............................... 2000/10056
Jan. 11, 2001  (JP) ............................... 2001/003476

(51) Int. Cl.
*C12N 15/82* (2006.01)
*C12N 15/29* (2006.01)
*A01H 5/00* (2006.01)

(52) U.S. Cl. ................... 800/289; 536/23.6; 435/320.1; 435/419; 435/468; 800/298

(58) Field of Classification Search ....................... None
See application file for complete search history.

(56) References Cited

U.S. PATENT DOCUMENTS 5,981,842 A    11/1999 Wu et al.
7,049,487 B2    5/2006 Iuchi et al.

FOREIGN PATENT DOCUMENTS

WO    WO 96/38566    12/1996
WO    WO 01/12801     2/2001

OTHER PUBLICATIONS

Iuchi K. et al., GenBank Accession No. BD017434, Aug. 27, 2002, Source Vigna unguiculata (cowpea).*
Hill M.A. et al Functional analysis of conserved histidines in ADP-glucose pyrophosphorylase from *Escherichia coli*. Biochem Biophys Res Commun. Mar 17, 1998;244(2):573-7.*
Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 13, 1998;273(46):30750-6.*
Muthukumar B. et al. Genetic transformation of cotyledon explants of cowpea (Vigna unguiculata L. Walp) using Agrobacterium tumefaciens. Plant Cell Rep, 1996, 15:980-985.*
Tamura T et al. Osmotic stress tolerance of transgenic tobacco expressing a gene encoding a membrane-located receptor-like protein from tobacco plants. Plant Physiol. Feb. 2003;131(2):454-62.*
Bevan et al. GenBank Accession No. AL021710 (2006).

Kasuga et al. "Improving plant drought, salt, and freezing tolerance by gene transfer of a single-stress inducible transcription factor" Nature Biotech. 17:287-291 (1999).
Liu et al. "Two transcription factors DREB1 and DREB2, with an EREBP/AP2 DNA binding domain separate two cellular signal transduction pathways in drought- and low-temperature-responsive gene expression, respectively, in Arabidopsis" Plant Cell 10:1391-1406 (1998).
Bevan et al. "*Arabidopsis thaliana* DNA, chromosome 4, BAC clone F28j12 (ESSAII project)" Accession No. AL021710 (1998).
Bevan et al. "Neoxanthin cleavage enzyme-like protein" Accession No. 049505 (1998).
Burbidge et al. "Structure and expression of a cDNA encoding a putative neoxanthin cleavage enzyme (NCE), isolated from a wilt-related tomato (*Lycopersicon esculentum* Mill.) library" J. Exp. Botany 47:2111-2112 (1997).
Burbidge et al. "Characterization of the ABA-deficient tomato mutant notabilis and its relationship with maize VP14" Plant J. 17:427-431 (1999).
Burbidge et al. "*Lycopersicon esculentum* mRNA for nine-cis-epoxycarotenoid dioxygenase" Accession No. Z97215 (1997).
Burbidge et al. "Neoxanthin cleavage enzyme" Accession No. 024023 (1998).
Chernys et al. "Characterization of the 9-cis-epoxycarotenoid dioxygenase gene family and the regulation of abscisic acid biosynthesis in avocado" Plant Physiol. 124:343-353 (2000).
Iuchi et al. "A stress-inducible gene for 9-cis-epoxycarotenoid dioxygenase involved in abscisic acid biosynthesis under water stress in drought-tolerant cowpea" Plant Physiol. 123:553-562 (2000).
Iuchi et al. "Neoxanthin cleavage enzyme" Accession No. Q9FS24 (2001).
Iuchi et al. "Vigna Unguiculata CPRD65 mRNA for neoxanthin cleavage enzyme complete cds" Accession No. AB030293 (2000).
Jaglo-Ottoson et al. "Arabidopsis CBF-1 overexpression induces COR genes and enhances freezing tolerance" Science 180:104-106 (1998).
Neill et al. "Regulation of gene expression during water deficit stress" Plant Growth Regulation 29:23-33 (1999).
Qin et al. "9-cis-epoxycarotenoid dioxygenase" Accession No. Q9M6E8 (2000).
Qin et al. "*Phaseolus vulgaris* 9-cis-epoxycarotenoid dioxygenase (NCED1) mRNA, complete cds" Accession No. AF190462 (2000).
Qin et al. "The 9-cis-epoxycarotenoid cleavage reaction is the key regulatory step of abscisic acid biosynthesis in water-stressed bean" Proc. Natl. Acad. Sci. USA 96:1534-15361 (1999).
Sato et al. "9-cis-epoxycarotenoid dioxygenase" Accession No. Q9LRM7 (2000).

(Continued)

*Primary Examiner*—Cynthia Collins
(74) *Attorney, Agent, or Firm*—Nixon & Vanderhye P.C.

(57) ABSTRACT

A DNA encoding a neoxanthin cleavage enzyme used for improving stress tolerance in a plant, a method for increasing stress tolerance in a plant by introducing the DNA into the plant, and a transgenic plant into which a neoxanthin cleavage enzyme gene is introduced, are provided. A DNA used for reducing stress tolerance in a plant, a method for decreasing stress tolerance in a plant by introducing the DNA into the plant, and a transgenic plant into which the DNA is introduced, are also provided. The present invention enables creating a plant in which stress tolerance has been increased or decreased.

22 Claims, 15 Drawing Sheets

OTHER PUBLICATIONS

Sato et al. "*Arabidopsis thaliana* genomic DNA, chromosome 3, P1 clone: MUJ8" Accession No. AB028621 (1999).

Sato et al. "*Arabidopsis thaliana* genomic DNA, chromosome 3, P1 clone: MOA2" Accession No. AB028617 (1999).

Sato et al. "Structural analysis of *Arabidopsis thaliana* chromosome 3. I. sequence features of the regions of 4,504,864 bp covered by sixty P1 and TAC clones" DNA Res. 7:131-135 (2000).

Swamy et al. "Role of abscisic acid in plant stress tolerance" Science 76:1220-1227 (1999).

Schwartz et al. "Specific oxidative cleavage of carotenoids by VP14 of maize" Science 276:1872-1874 (1997).

Tan et al. "Genetic control of abscisic acid biosynthesis in maize" Proc. Natl. Acad. Sci. USA 94:12235-2240 (1997).

Tan et al. "Viviparous 14", Accession No. 024592 (1998).

Tan et al. "*Zea mays* viviparous-14 (vp14) mRNA complete" Accession No. ZMU95953 (1997).

Thompson et al. "Ectopic expression of a tomato 9-cis-epoxycarotenoid dioxygenase gene causes over-production of abscisic acid" Plant J. 23:363-374 (2000).

Thompson et al. "Abscisic acid biosynthesis in tomato: Regulation of zeaxanthin epoxidase and 9-cis-epoxycarotenoid dioxygenase mRNAs by light/dark cycles, water stress and abscisic acid" Plant Mol. Biol. 42:833-845 (2000).

Int'l Search Report for EP 01300218.3 dated Oct. 29, 2001.

Int'l Search Report for EP 01300218.3 dated Jun. 7, 2001.

* cited by examiner

Figure 1

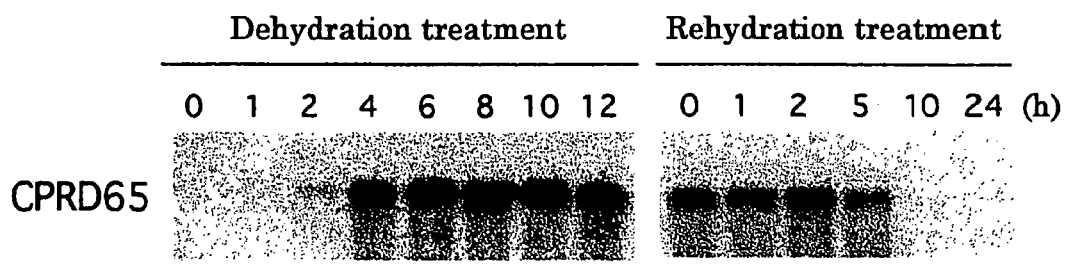

Figure 2

```
CPRD65    MPSSASNTWFNATLPSPPFKDLPSTSSPTNLLPLRKTSSSNTITCSLQFLHFPKQYQPTSTSTSTATTTTPTPIKTTTITTTTPPRETNP     90
VP14      MQGLAPPTSVSIHRHLPA-RSRARASNSVRFSP-RAVSSVPPAEC-LQA-PFHK-----PVADLPAPSRKPAAI--AVPGHAAAPRKAEG     79
LeNCED1   MATTTSH---ATNTWIKT-KLSMPSSKEFGFAS-NSISLLKNQHN-RQSLNINS---SLQAPPILHFPKQSSNYQTPKNNTISHPKQEN-     80

CPRD65    LSDTNQPLPQKWNFLQKAAATALDLVETALVSHERKHHLPKTADPRVQIAGNFAPVPEHAADQGLPVMGKIPKCIDGVYMRNGANPLYSP    180
VP14      -GKKQLNLFQR-AAAAALDAFEEGFVANVL---ERPHGLPSIADPAVQIAGNFAPVGERPPVHELPVSGKIPPFIDGVYARNGANPCFDP    164
LeNCED1   -NNSSSSSTSKWNLVQKAAAMALDAVESALTKHELEHLPKTADPRVQISGNFAPVPENPVCQSLPVFGKIPKCVQGVYMRNGANPLFEP    169

CPRD65    VAGHHFDGDGMVHAVKFTNGMAI-SYACRFTETHRLHQEKSLGRPVFPKAIGELHGHSGIARLLLFYARGLFGLVDHSHGMGVANAGLVY    269
VP14      VAGHHLFDGDGMVHALRIRNGMAHSYACRFTETHRLHQERAIGRPVFPKAIGELHGHSGIARLALFYARAAGLVDPSAGITGVANAGLVY    254
LeNCED1   TAGHHFFDGDGMVHAVQFKNGSAHSYACRFTETFKLVQEKALGRPVFPKAIGELHGHSGIARLMLFYARGLFGLVDHSKGITGVANAGLVY    258

CPRD65    FNNHLLAMSEDDLPYHVRITPNGDLITVGRMDFNGQLNSTMIAHPKLDPVDGQLHALSYDVIQKPYLKYFNFSPDGMKSPDVEIPLKEPT    359
VP14      FNGRLLAMSEDDLPYHVRVADDGDLETVGRMDFDGQLGCAMIAHPKLDPATGELHALSYDVIKRPYLKYFTFRPDGMKSDDVEIPLEQPT    344
LeNCED1   FNNRLLAMSEDDLPYHVKVTPTGDLKTEGRMDFDGQLKSTMIAHPKLDPVSGELHALSYDVIQKPYLKYFNFSKNGEKSNDVEIPVEDPT    348

CPRD65    PAHDFAITENFVVIPDQQVVFKLTEMITGGSPVVLDKNISRFGDLLKNAKEANAMRNKDAPDCFCFHLWNAWEEPETEEMVVIGSCMTP    449
VP14      MLHDFAITENFVVLPDHQVVFKLQEMLRGGSPVVLDKEKITSRFGVLPKHANDASEMAMWDVPDCFCFHLWNAWEDEATQEMVVIGSCMTP    434
LeNCED1   KMHDFAITENFVVIPDQQVVFKMSEMIRGGSPVVMDKNKVSRFGDLPKMAKDGSDLKMWEVPDCFCFHLWNAWEFAETTELVVIGSCMTP    438

CPRD65    ADSIFNELEELSKSVLSEIRLNLRTGKSTRRPIISDAEQ-VNLENGMVNRNKLGRKTQFAYLALAEPWPKMSGFAKVDLLSGEVKKYMYG    538
VP14      ADSIFNESDERLFSVLMEIRLDARTGRSTRRAVLPPSQQ-ENLEVQMVRNLLGRESRYAYLAMAEPWPKESGFAKFDLSTGELTKFEYG    523
LeNCED1   PDSIFNELDEFLKEVLSEIRLNLKIGKSTRKSIIENPDEQVNLENGMVNRNKLGRKTEYAYLAHAEPWPKVSGFAKVNLFTGEVEKFIYG    528

CPRD65    EEKFGGEPLFLPL-----NGQKEDDGYILNFVHDEKEWKSELQIVNAQNLKLEASIKLPSRVPMGFHGTFIHSKDLRKDAH          612
VP14      EGRFGGEPLFVPMDPAAAHPRGEDDGYVALFVHDERAGTSELLVWNAADIRLEAIVQLPSRVPHGFHGTFIIGQELEADAA           604
LeNCED1   DNKYGGEPLFLPRDP---NSKEEDDGYILNFVHDEKEWKSELQIVNAMSLKLEAFVKLPSRVPMGFHGTFINANDLANDAH           605
```

Figure 4
(A)
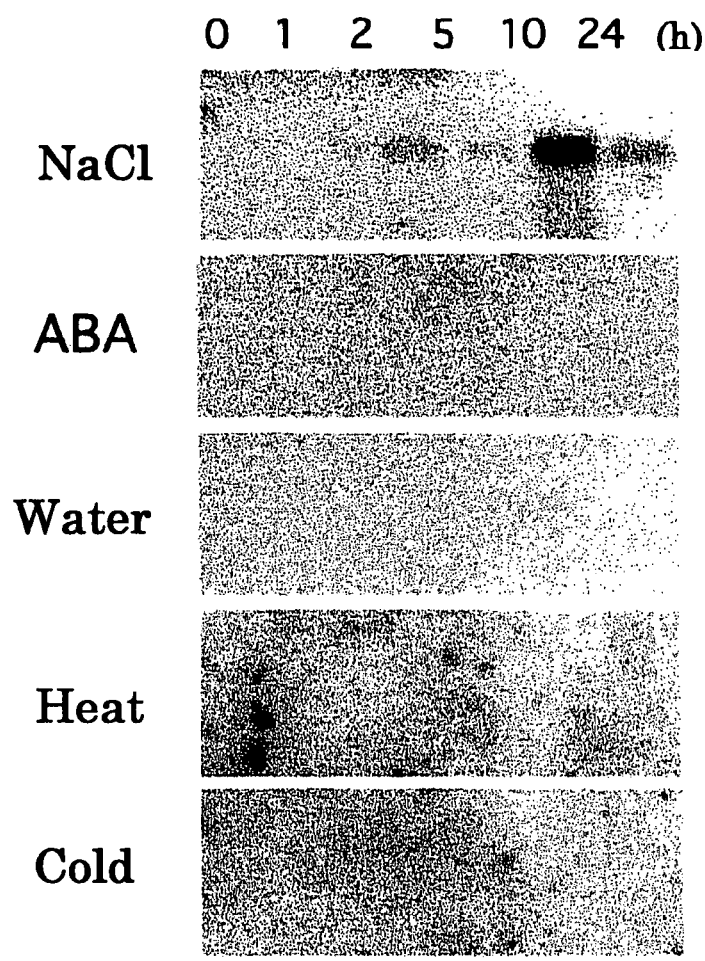
(B)
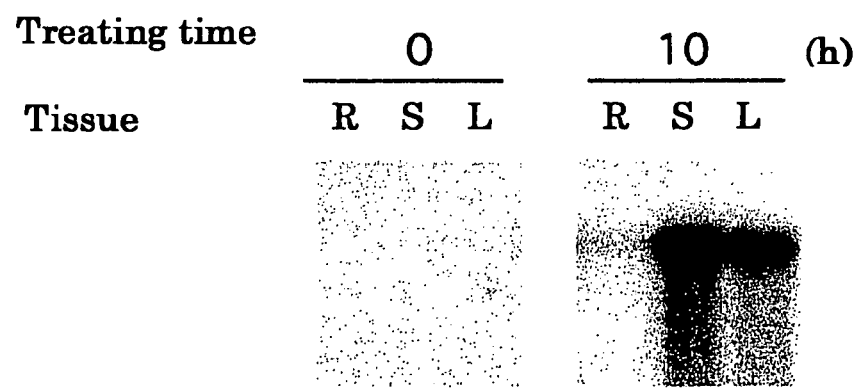

Figure 5
(A)
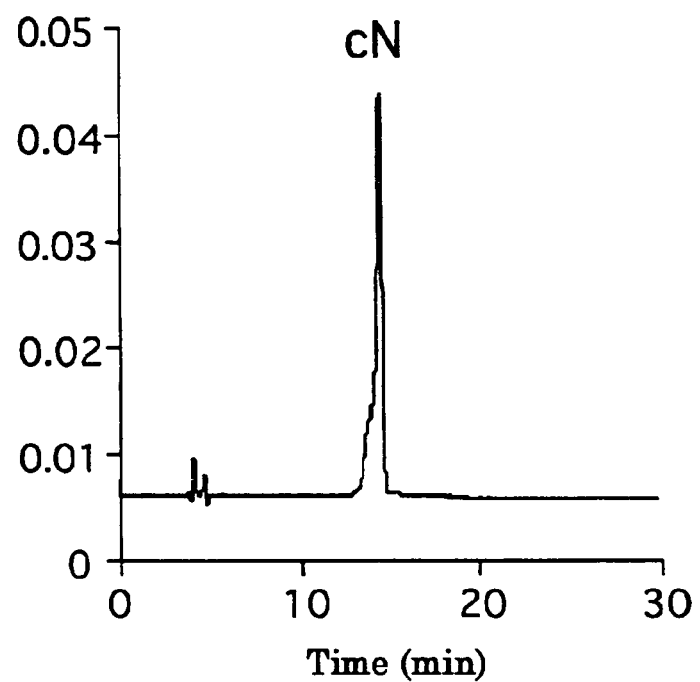
(B)
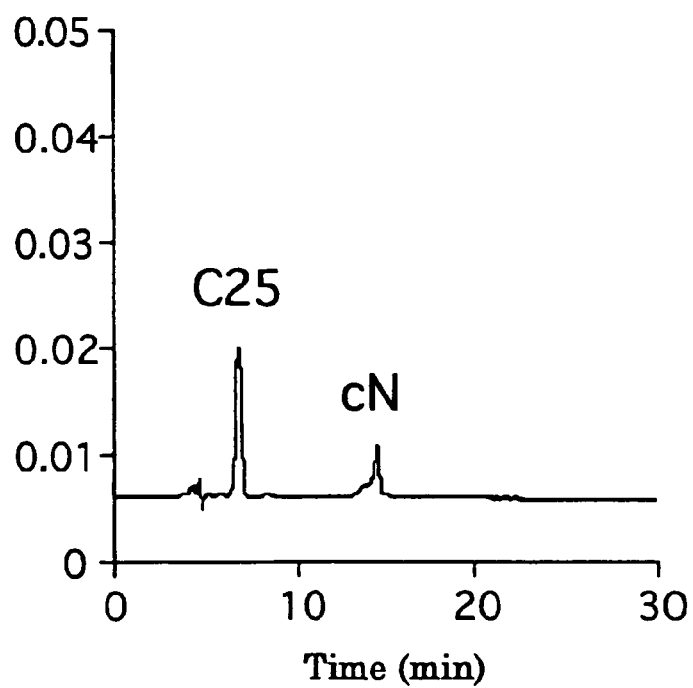

Figure 9

```
AtNCED3    MAS-----FTATAAVSG-RHLGGNHTQP---PLSSSQSSDLSYCS--SL--PMASRVTRKLNVSSALHTPPALH      61
CPRD65     MSSASNTWFNATLPSPPFKDLPSTSSPTNLLPLRKTSSSNTITCSLQTLHPKQYQRTSTSTSTATTTTPTPIK     75

AtNCED3    FPKQSSNSPAIVVKP--KAKESNTKQMNLFQKAAAHALDAAEGHLVSHEKLHPLPKTADPHVQIAGNFAPVNEQP   134
CPRD65     TTTITTTTPPRETNPLSDTNQPLPQKWNFLQKAAATALDLVETALVSHERKHPLPKTADPHVQIAGNFAPVREHA   150

AtNCED3    VRRNLPVVGKLPDSIKGVYVRNGANPLHEPVIGHHFFDGDGMVHAVKFEHGHASYACRFTQTNRFVQERQLGRPY   209
CPRD65     ADQGLPVVGKIPKQIDGVYVRNGANPLHEPVIGHHFFDGDGMVHAVKFTNGHASYACRFTETQRLSQEKSLGRPY   225

AtNCED3    FPKAIGELHGHTGIARLHLFYARAAAGIVDPAHGIGVANAGLVYFNGRLLAMSEDDLPYQVQITPNGDLHTVGRF   284
CPRD65     FPKAIGELHGHSGIARLILFYARGLFGIVDGSQGHGVANAGLVYFNNHLLAMSEDDLPYHVRITPNGDLITTVGRY  300

AtNCED3    DFDGQLHSTMIAHPKVDPESGHLHALSYDVVSKPYLKYFRFSPDGIKSPDVEIQLDQPTMMHDFAITENFVVVPD   359
CPRD65     DFNGQLNSTMIAHPKLDPVDGDLHALSYDVLQKPYLKYFRFSPDGVKSPDVEIHLKEPTMMHDFAITENFVVVPD   375

AtNCED3    QQVVFKLHEMIKGGSPVVYDKNKVARFGILDKMAHDSSNIKWIDAPDCFCFHLMNAWEEPETHEVVVIGSCMTPP   434
CPRD65     QQVVFKLIEMITGGSPVVYDKNKTSRFGILHKNAKDANAMRWIDAPDCFCFHLMNAWEEPETEEVVVIGSCMTPA   450

AtNCED3    DSIFNESDEHLKSVLSEIRLNLKTGESTRRPIISNEDQQVNLEAGMVNRNHLGRKTKFAYLALAEPWPKVSGFAK   509
CPRD65     DSIFNECEEHLKSVLSEIRLNLRTGKSTRRPIISDAEQHVNLEAGMVNRNHLGRKTQFAYLALAEPWPKVSGFAK   524

AtNCED3    VDLTTGEVKKHLYGDNRYGGEPLFLPGEGGEEDHGYILQFVHDEKTWKSELQIVNAVSLEVEATVKLPSRVPYGF   584
CPRD65     VDLLSGEVKKYMYGEEKFGGEPLFLPFNGDKEDHGYILHFVHDEKEWKSELQIVNAQNLKLEASIKLPSRVPYGF   598

AtNCED3    HGTFIGADDLAKQVV    599
CPRD65     HGTFIHSKDLRKQA-    612
```

Figure 10

```
AtNCED1    MVSL-LTMPMS----GGIKTWPQ---AQ-IDLGF-RPIKRQPKV-----IKCTVQIDVTELTKKRQLFTPRTTAT       60
AtNCED2    MDSVSSSSFLS----STFSLHHS---LLRRRSSSPTLLRINSAVV----EERSPITNPSDNNDRRNKPKTLHNRT      64
AtNCED3    MASFTATAAVSGRWLGGNHTQPPLSSSQSSDLSYCSSLPMASRVTRKLNVSSALHTPPALHFPKQSSNSPAIVVK      75
AtNCED4    MA--------------------------------EKLSDGS--------IIISVHPRPS----------------      19
AtNCED5    MQHSLRSDLLPTKTSPRSHLLPQPKNANISRRILINPFKIPTLPDLTSPVPSPVKLKPTYPNLNLLQKLAATMLD      75

AtNCED1    P---PQHNPLRLNIFQKAAAIAIDAAERALISHEQDSPLPKTADPRVQIAGNYSPVPESSVRRNL-TVEGIIPDCI    132
AtNCED2    NHTLVSSPPKLRPEMTLATALFTTVEDVINTFIDPPSRP-SVDPKHVLSDNFAPVLDELPPTDCEIIHGTLPLSL    138
AtNCED3    PKAKESNTKQVNLFQRAAAAALDAAEGFLVSHEKLHPLPKTADPSVQIAGNFAPVNEQPVRRNL-PVVGKLPDSI    149
AtNCED4    ------------KGF---SSKLLDLLERLWKLMHDASLPLHY-----LSGNFAPIRDETPPVKDLPVH-GFLPECL      75
AtNCED5    KIESSIVIPMEQNRPLPKPTDPAVQLSGNFAPVNECPVQNG---------------------LEVMGQIPSCL    127

AtNCED1    DGVYIRNGANPVFEPTAGHHLFDGDGMVHAVKIT-NGSASYACRFTKTERLVQEKRLGRPVFPKAIGELHGHS-G    205
AtNCED2    NGAYIRNGPNPDFLPRGPYHLFDGDGMLHAIKIH-NGKATLCSRAVKTYKYNMEKQTIGAPVMPNVFSGFNGVTAS    212
AtNCED3    KGVYVRNGANPLHEPVTGHHFFDGDGMVHAVKFE-HGSASYACRFTQINRPVQERQLGRPVFPKAIGELHGHT-G    222
AtNCED4    NGEFVRVGPNPKFDAVAGYHNFDGDGMFHGVRIK-DGKATYVSRIVKTSRLKQEEFFGAAKFMK-IGDLKGFF-G    147
AtNCED5    KGVYIRNGANPVFPPLAGHHLFDGDGMHAVSIGFDNQVSYSCRVTKINRLVQETALGRSVFPKPIGELHGHS-G    201

AtNCED1    IARLMEFYARGLCGLINNQNGVGVANAGLVYFNNRLLAMSEDDLPYLKFTQTGDLQTVGRYDFDGQLKSAMIAH    280
AtNCED2    VARGALTAARVLTGQYNPVNGIGLANESLAFFSNRFALGEBDLPYAVRLTESGDIFITGKRYDFDGKLAMSMTAH    287
AtNCED3    IARLMLFYARAAAGIVDPAHGIGVANAGLVYFNGRLLAWSEDDLPYLTPNGDLKTVGRFDFDGQLESTMIAH    297
AtNCED4    LLMVNIQQLRTKLKILDNTYGNGIANTALVYHGKLALQEMEKPVYIKVLEDGDLQTLGIIDYDKRLTHSFTAH    222
AtNCED5    LARLAEFTARAGIGLVDGTRGMGVANAGWFFNGRLLAMSEDLPYLQVKIDGCGDLEIIGRFGFHDQIDSSVIAH    276

AtNCED1    PKLDPVTKELHALSYDVVKKPYLKYFRFSPDGVKSPELEII-PLETFMIHDFAITENFVVIPDQQVVFKLGEM--    352
AtNCED2    RCIPPITGETFAFRYGPV-PFFEIYRFDSAGKKQRDVFEIFSMTSPSFLIHDFAITKRHAIFAEIQLGVRMNMLDL    361
AtNCED3    PKVDPESGELFALSYDVVSKPYLKYFRFSPDGTKSPDVEEL-QLDQPIMMHDFAITENFVVPDQQVVFKLPEM--    369
AtNCED4    PKVDPVTGEMFTFGYS-HTPPYLIYRVISKDGIMHDPVPIL-TISEPIMMHDFAITETYAIFMDLPMHFRPKEM--    293
AtNCED5    PKVEATTGDLHTLSYNVLKKPHLERYLKFNTCGKKTRDVEII-TLPEPTMILHDFAITENFVVIPDQQVWFKLSEM--    348

AtNCED1    ISGKSPV-VFDGEKVSRLGIMPKDATEASQLLMVNSPETFCFHLWNAMESPETEE---IV---VIGSCMSPADSI    420
AtNCED2    VLEGGSPVGTDNGKIPRLGVIPKYAGCDESEMKWFEVPGNIIHAINAWDEDDGNS----VV---LIAPNIMSIEHT    430
AtNCED3    IRGGSPV-VYDKNIVARFGELDKYAEDSSNDKWIDAPDCFCFHLWNAMEEPETDE---VV---VIGSCMTPPDSI    437
AtNCED4    VKEKKMIYSFDPTIKKARFGVLPRYAKDELMDIRMFELPNCFIHNANAWEEEDE---WLITCRLENPDLDMVSGK    365
AtNCED5    IRGGSPV-IYVKEKWARFGVLSKQDLTGSDINWVDMPDCFCFHLWNAMEERTEEGDPVIV---VIGSCMSPPDTI    419

AtNCED1    FNERDESLRSVLSEIRINLRTRKTTRRSLLV--NEDVNLEIGMV-NRNRLGRKTRFAFLALAYPWFKVSGFAKVD    492
AtNCED2    L-ERMDLVHALVEKVKIDLVTGIVRRHPISA-----RNLDFAVI-NPAFLGRCSRYVYAAIGDPMFKISGVVKLD    498
AtNCED3    FNESDENLKSVLSEIRLNLKTGESTRRPTISNEDQQVNLEAGMV-NRNMLGRKTKFAYLALAEPWFKVSGFAKVD    511
AtNCED4    VKEKLENFGNELYEMRFNMKTGSASQKKLSASAVDFPRINECYTGKKQRYVYGTILDSIAKVTGLIKFDLHAEAE    440
AtNCED5    FSEBGEPTRVELSEIRLMMRTKESNRKVIVT----GVNLEAGHI-NRSYVGRKSQFVYIATADPWFKCSGIAKVD    489

AtNCED1    LCTGEMKKYIYGGEKYG-G--EPFFLPGN--SGNGEENEDDGYLFCHV-HDEETKTSELQILNAVNLKLE--AIIK    560
AtNCED2    VSKGDRDDCTVARRMYGSGCYGGEPFFVARDPGNPEAEEDDGYVTYVHDEVTGESKFLVMDAKSPELEIVAAVR    573
AtNCED3    LTTGEVKKHLYGDNRYG-G--EPLFLPGE--GGEEDE----GYILCFVHDEKTWKSELQIVNAVSLEVE--AIVK    575
AtNCED4    TGKRMLEVGGNIKGIYDLG--EGRYGSEATYVPRETAEEDDGYIIFRVHDENTGKSLVTVIDAKTMSAEPVAVVE    513
AtNCED5    IQNGTVSEFNYGPSRFG-G--EPCFVPEG--EGEEDK----GYVMGFVRDEEKDESEFVWVDAIDMKQV--AAVR    553

AtNCED1    LPRRVPYGFHGIFVDSNELVDQL--    583
AtNCED2    LPRRVPYGFHGLPVKESDINKL---    595
AtNCED3    LPRRVPYGFHGIFICADDLAKQ-VV    599
AtNCED4    LPHRVPYGFHALFVTEEDLDEQTLI    538
AtNCED5    LPRRVPYGFHGIFVSENQLKEQ-VF    577
```

Figure 15
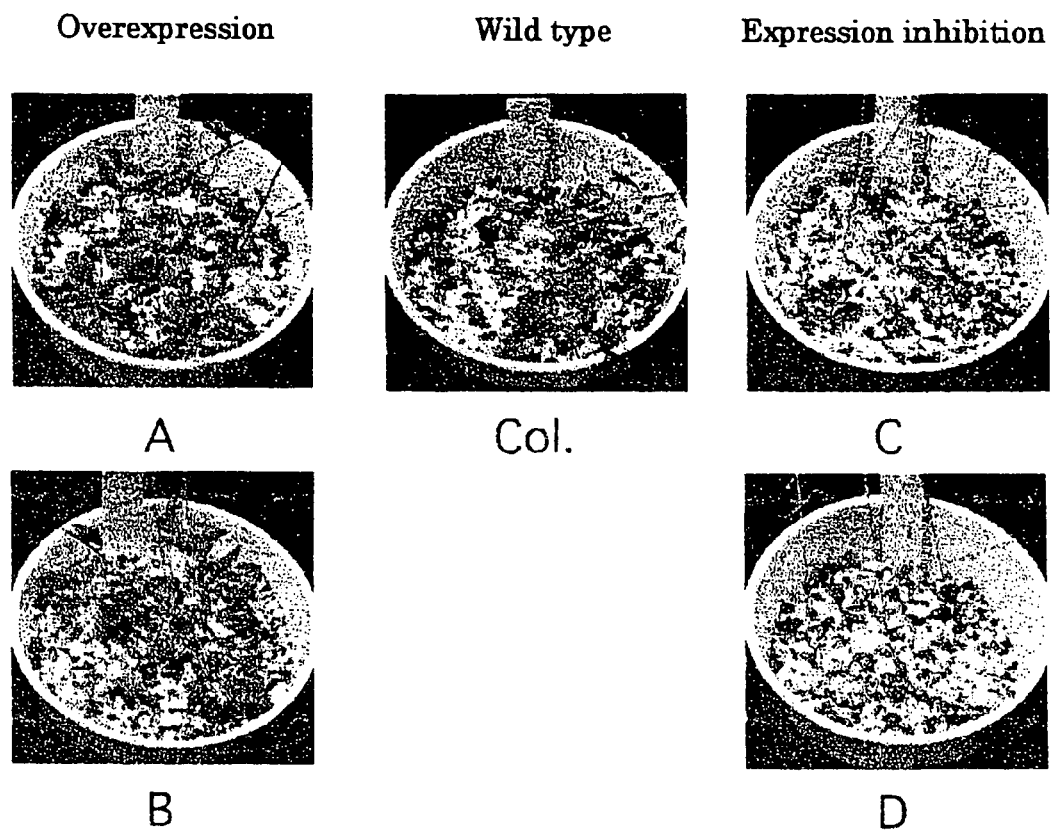
Overexpression — A, B
Wild type — Col.
Expression inhibition — C, D
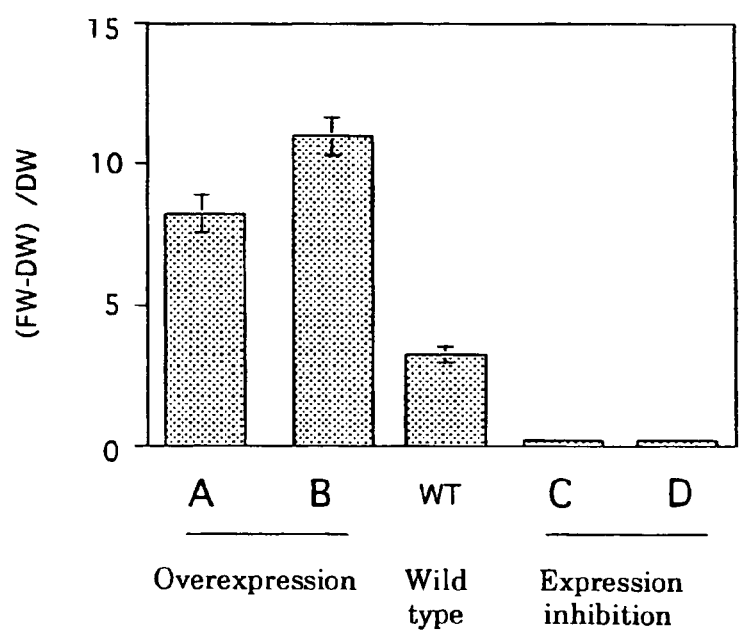
Water content of plants
14 days after tolerance evaluation
y-axis: (FW-DW)/DW
x-axis: A  B  (Overexpression)  WT (Wild type)  C  D (Expression inhibition)

```
                        SEQUENCE LISTING

<160> NUMBER OF SEQ ID NOS: 33

<210> SEQ ID NO 1
<211> LENGTH: 1752
<212> TYPE: DNA
<213> ORGANISM: Arabidopsis thaliana
<220> FEATURE:
<221> NAME/KEY: CDS
<222> LOCATION: (1)..(1749)

<400> SEQUENCE: 1 atg gtt tct ctt ctt aca atg ccg atg agt ggt ggt att aaa aca tgg      48
Met Val Ser Leu Leu Thr Met Pro Met Ser Gly Gly Ile Lys Thr Trp
 1               5                  10                  15 cct caa gcc caa att gat ttg ggt ttt agg ccc att aaa aga caa ccg      96
Pro Gln Ala Gln Ile Asp Leu Gly Phe Arg Pro Ile Lys Arg Gln Pro
             20                  25                  30 aag gtt att aaa tgc acg gtg cag atc gac gta acg gaa tta acc aaa     144
Lys Val Ile Lys Cys Thr Val Gln Ile Asp Val Thr Glu Leu Thr Lys
         35                  40                  45 aaa cgc caa tta ttt aca ccc aga acc acc gct act ccg ccg cag cat     192
Lys Arg Gln Leu Phe Thr Pro Arg Thr Thr Ala Thr Pro Pro Gln His
     50                  55                  60 aat cct ctc cgg cta aac atc ttc cag aaa gcg gcg gcg att gcg atc     240
Asn Pro Leu Arg Leu Asn Ile Phe Gln Lys Ala Ala Ala Ile Ala Ile
 65                  70                  75                  80 gac gcg gct gag cgt gca tta atc tca cac gag caa gat tct cca ctt     288
Asp Ala Ala Glu Arg Ala Leu Ile Ser His Glu Gln Asp Ser Pro Leu
                 85                  90                  95 ccc aaa acc gct gat cca cgt gtt cag att gcc ggg aat tat tcc ccg     336
Pro Lys Thr Ala Asp Pro Arg Val Gln Ile Ala Gly Asn Tyr Ser Pro
            100                 105                 110 gta ccg gaa tct tcc gtc cgg cga aac ctc acc gtc gaa gga aca atc     384
```

```
                Val Pro Glu Ser Ser Val Arg Arg Asn Leu Thr Val Glu Gly Thr Ile
                        115                 120                 125 cct gac tgc att gac ggt gtt tat atc cgt aac ggc gcg aat ccg atg           432
Pro Asp Cys Ile Asp Gly Val Tyr Ile Arg Asn Gly Ala Asn Pro Met
130                 135                 140 ttt gag cca aca gct ggg cac cat tta ttc gac gga gac gga atg gtt           480
Phe Glu Pro Thr Ala Gly His His Leu Phe Asp Gly Asp Gly Met Val
145                 150                 155                 160 cac gca gtt aaa ata acc aac ggt tca gct agc tac gca tgc cgg ttt           528
His Ala Val Lys Ile Thr Asn Gly Ser Ala Ser Tyr Ala Cys Arg Phe
                165                 170                 175 aca aaa acc gag aga ttg gtt cag gaa aaa cga ttg ggt cga cca gtt           576
Thr Lys Thr Glu Arg Leu Val Gln Glu Lys Arg Leu Gly Arg Pro Val
            180                 185                 190 ttc ccg aaa gca atc ggc gag ctt cac ggt cac tcg gga atc gca cgt           624
Phe Pro Lys Ala Ile Gly Glu Leu His Gly His Ser Gly Ile Ala Arg
        195                 200                 205 ttg atg ctg ttt tac gca cgt ggg ctt tgt ggt ctg atc aac aac caa           672
Leu Met Leu Phe Tyr Ala Arg Gly Leu Cys Gly Leu Ile Asn Asn Gln
    210                 215                 220 aac ggc gtc gga gta gca aac gcc ggt ttg gtt tac ttt aat aac cgg           720
Asn Gly Val Gly Val Ala Asn Ala Gly Leu Val Tyr Phe Asn Asn Arg
225                 230                 235                 240 ctt tta gct atg tca gaa gac gat tta ccg tac caa tta aaa att act           768
Leu Leu Ala Met Ser Glu Asp Asp Leu Pro Tyr Gln Leu Lys Ile Thr
                245                 250                 255 caa acc ggc gat ctc caa acc gtt gga cgt tac gat ttc gac ggt cag           816
Gln Thr Gly Asp Leu Gln Thr Val Gly Arg Tyr Asp Phe Asp Gly Gln
            260                 265                 270 tta aaa tcc gca atg ata gct cac ccg aaa ctg gac ccg gtt acg aag           864
Leu Lys Ser Ala Met Ile Ala His Pro Lys Leu Asp Pro Val Thr Lys
        275                 280                 285 gag ctt cac gcg tta agc tac gac gtc gtt aag aaa cct tac ctg aaa           912
Glu Leu His Ala Leu Ser Tyr Asp Val Val Lys Lys Pro Tyr Leu Lys
    290                 295                 300 tac ttc aga ttc tcg cca gac ggc gtt aaa tcg ccg gaa ttg gag atc           960
Tyr Phe Arg Phe Ser Pro Asp Gly Val Lys Ser Pro Glu Leu Glu Ile
305                 310                 315                 320 ccg ctc gaa act ccg acg atg att cac gat ttc gct ata acg gag aat          1008
Pro Leu Glu Thr Pro Thr Met Ile His Asp Phe Ala Ile Thr Glu Asn
                325                 330                 335 ttt gtg gtg att cct gat caa caa gtc gtg ttc aag ctc ggc gag atg          1056
Phe Val Val Ile Pro Asp Gln Gln Val Val Phe Lys Leu Gly Glu Met
            340                 345                 350 att tcc ggt aaa tct ccg gtt gtt ttc gac gga gaa aag gtt tcc cga          1104
Ile Ser Gly Lys Ser Pro Val Val Phe Asp Gly Glu Lys Val Ser Arg
        355                 360                 365 ttg ggg ata atg ccc aag gac gcg aca gaa gct tct cag ata atc tgg          1152
Leu Gly Ile Met Pro Lys Asp Ala Thr Glu Ala Ser Gln Ile Ile Trp
    370                 375                 380 gtg aac tct ccg gag acg ttc tgt ttt cat ctc tgg aat gca tgg gaa          1200
Val Asn Ser Pro Glu Thr Phe Cys Phe His Leu Trp Asn Ala Trp Glu
385                 390                 395                 400 tcg ccg gag acg gag gag att gtg gtg atc gga tcg tgt atg tcg ccg          1248
Ser Pro Glu Thr Glu Glu Ile Val Val Ile Gly Ser Cys Met Ser Pro
                405                 410                 415 gcg gat tca atc ttc aac gag aga gac gag agc ttg aga agc gtt ttg          1296
Ala Asp Ser Ile Phe Asn Glu Arg Asp Glu Ser Leu Arg Ser Val Leu
            420                 425                 430
```

```
tcg gag atc agg ata aac ctc aga aca cgt aaa acc acg cgt cgt tcg      1344
Ser Glu Ile Arg Ile Asn Leu Arg Thr Arg Lys Thr Thr Arg Arg Ser
            435                 440                 445 ttg ttg gtt aac gag gat gta aat tta gag att ggt atg gtt aac cgg      1392
Leu Leu Val Asn Glu Asp Val Asn Leu Glu Ile Gly Met Val Asn Arg
450                 455                 460 aac cgg tta gga aga aaa acc cgg ttc gcg ttt ttg gct att gct tat      1440
Asn Arg Leu Gly Arg Lys Thr Arg Phe Ala Phe Leu Ala Ile Ala Tyr
465                 470                 475                 480 cct tgg cca aaa gtt tcc ggt ttc gct aag gtc gat ctt tgc acc ggt      1488
Pro Trp Pro Lys Val Ser Gly Phe Ala Lys Val Asp Leu Cys Thr Gly
                485                 490                 495 gag atg aaa aaa tat att tac ggc ggt gag aaa tat ggc ggc gaa ccg      1536
Glu Met Lys Lys Tyr Ile Tyr Gly Gly Glu Lys Tyr Gly Gly Glu Pro
            500                 505                 510 ttt ttc ttg ccc ggc aac tcc ggt aac ggc gaa gaa aat gaa gat gac      1584
Phe Phe Leu Pro Gly Asn Ser Gly Asn Gly Glu Glu Asn Glu Asp Asp
            515                 520                 525 ggt tat ata ttt tgt cac gtt cat gac gaa gaa aca aag aca tca gag      1632
Gly Tyr Ile Phe Cys His Val His Asp Glu Glu Thr Lys Thr Ser Glu
530                 535                 540 ctt cag att att aac gct gtt aat tta aag ctt gaa gct acg att aaa      1680
Leu Gln Ile Ile Asn Ala Val Asn Leu Lys Leu Glu Ala Thr Ile Lys
545                 550                 555                 560 cta ccg tct aga gta ccg tat ggg ttt cat ggc aca ttt gtg gat tcg      1728
Leu Pro Ser Arg Val Pro Tyr Gly Phe His Gly Thr Phe Val Asp Ser
                565                 570                 575 aat gaa ctc gtt gat caa tta taa                                      1752
Asn Glu Leu Val Asp Gln Leu
            580
```

<210> SEQ ID NO 2
<211> LENGTH: 583
<212> TYPE: PRT
<213> ORGANISM: Arabidopsis thaliana

<400> SEQUENCE: 2

```
Met Val Ser Leu Leu Thr Met Pro Met Ser Gly Gly Ile Lys Thr Trp
1               5                   10                  15

Pro Gln Ala Gln Ile Asp Leu Gly Phe Arg Pro Ile Lys Arg Gln Pro
                20                  25                  30

Lys Val Ile Lys Cys Thr Val Gln Ile Asp Val Thr Glu Leu Thr Lys
            35                  40                  45

Lys Arg Gln Leu Phe Thr Pro Arg Thr Thr Ala Thr Pro Pro Gln His
        50                  55                  60

Asn Pro Leu Arg Leu Asn Ile Phe Gln Lys Ala Ala Ile Ala Ile
65                  70                  75                  80

Asp Ala Ala Glu Arg Ala Leu Ile Ser His Glu Gln Asp Ser Pro Leu
                85                  90                  95

Pro Lys Thr Ala Asp Pro Arg Val Gln Ile Ala Gly Asn Tyr Ser Pro
            100                 105                 110

Val Pro Glu Ser Ser Val Arg Arg Asn Leu Thr Val Glu Gly Thr Ile
        115                 120                 125

Pro Asp Cys Ile Asp Gly Val Tyr Ile Arg Asn Gly Ala Asn Pro Met
    130                 135                 140

Phe Glu Pro Thr Ala Gly His His Leu Phe Asp Gly Asp Gly Met Val
145                 150                 155                 160

His Ala Val Lys Ile Thr Asn Gly Ser Ala Ser Tyr Ala Cys Arg Phe
```

```
            165                 170                 175
Thr Lys Thr Glu Arg Leu Val Gln Glu Lys Arg Leu Gly Arg Pro Val
        180                 185                 190

Phe Pro Lys Ala Ile Gly Glu Leu His Gly His Ser Gly Ile Ala Arg
        195                 200                 205

Leu Met Leu Phe Tyr Ala Arg Gly Leu Cys Gly Leu Ile Asn Asn Gln
    210                 215                 220

Asn Gly Val Gly Val Ala Asn Ala Gly Leu Val Tyr Phe Asn Asn Arg
225                 230                 235                 240

Leu Leu Ala Met Ser Glu Asp Leu Pro Tyr Gln Leu Lys Ile Thr
                245                 250                 255

Gln Thr Gly Asp Leu Gln Thr Val Gly Arg Tyr Asp Phe Asp Gly Gln
            260                 265                 270

Leu Lys Ser Ala Met Ile Ala His Pro Lys Leu Asp Pro Val Thr Lys
        275                 280                 285

Glu Leu His Ala Leu Ser Tyr Asp Val Val Lys Pro Tyr Leu Lys
    290                 295                 300

Tyr Phe Arg Phe Ser Pro Asp Gly Val Lys Ser Pro Glu Leu Glu Ile
305                 310                 315                 320

Pro Leu Glu Thr Pro Thr Met Ile His Asp Phe Ala Ile Thr Glu Asn
                325                 330                 335

Phe Val Val Ile Pro Asp Gln Gln Val Val Phe Lys Leu Gly Glu Met
                340                 345                 350

Ile Ser Gly Lys Ser Pro Val Val Phe Asp Gly Glu Lys Val Ser Arg
            355                 360                 365

Leu Gly Ile Met Pro Lys Asp Ala Thr Glu Ala Ser Gln Ile Ile Trp
    370                 375                 380

Val Asn Ser Pro Glu Thr Phe Cys Phe His Leu Trp Asn Ala Trp Glu
385                 390                 395                 400

Ser Pro Glu Thr Glu Ile Val Val Ile Gly Ser Cys Met Ser Pro
                405                 410                 415

Ala Asp Ser Ile Phe Asn Glu Arg Asp Glu Ser Leu Arg Ser Val Leu
            420                 425                 430

Ser Glu Ile Arg Ile Asn Leu Arg Thr Arg Lys Thr Thr Arg Arg Ser
        435                 440                 445

Leu Leu Val Asn Glu Asp Val Asn Leu Glu Ile Gly Met Val Asn Arg
    450                 455                 460

Asn Arg Leu Gly Arg Lys Thr Arg Phe Ala Phe Leu Ala Ile Ala Tyr
465                 470                 475                 480

Pro Trp Pro Lys Val Ser Gly Phe Ala Lys Val Asp Leu Cys Thr Gly
                485                 490                 495

Glu Met Lys Lys Tyr Ile Tyr Gly Gly Glu Lys Tyr Gly Gly Glu Pro
            500                 505                 510

Phe Phe Leu Pro Gly Asn Ser Gly Asn Gly Glu Asn Glu Asp Asp
    515                 520                 525

Gly Tyr Ile Phe Cys His Val His Asp Glu Glu Thr Lys Thr Ser Glu
    530                 535                 540

Leu Gln Ile Ile Asn Ala Val Asn Leu Lys Leu Glu Ala Thr Ile Lys
545                 550                 555                 560

Leu Pro Ser Arg Val Pro Tyr Gly Phe His Gly Thr Phe Val Asp Ser
                565                 570                 575

Asn Glu Leu Val Asp Gln Leu
            580
```

```
<210> SEQ ID NO 3
<211> LENGTH: 1788
<212> TYPE: DNA
<213> ORGANISM: Arabidopsis thaliana
<220> FEATURE:
<221> NAME/KEY: CDS
<222> LOCATION: (1)..(1785)

<400> SEQUENCE: 3 atg gac tct gtt tct tct tct tcc ttc ctc tcc tcc aca ttc tct ctt        48
Met Asp Ser Val Ser Ser Ser Ser Phe Leu Ser Ser Thr Phe Ser Leu
1               5                   10                  15 cat cac tct ctt ctt cgc cgc cga tct tcc tct cct act ctc ctc cgt        96
His His Ser Leu Leu Arg Arg Arg Ser Ser Ser Pro Thr Leu Leu Arg
                20                  25                  30 atc aac tcc gcc gtc gtc gaa gaa cgt tct cca atc aca aac cca agc       144
Ile Asn Ser Ala Val Val Glu Glu Arg Ser Pro Ile Thr Asn Pro Ser
            35                  40                  45 gac aac aat gat cgt cgt aac aaa ccc aaa aca ctc cac aac cga acc       192
Asp Asn Asn Asp Arg Arg Asn Lys Pro Lys Thr Leu His Asn Arg Thr
        50                  55                  60 aat cac acc tta gtc tca tca cca ccg aaa ctc cga cca gaa atg act       240
Asn His Thr Leu Val Ser Ser Pro Pro Lys Leu Arg Pro Glu Met Thr
65                  70                  75                  80 ctc gca aca gct ctc ttc acc acc gtc gaa gat gta atc aac acg ttc       288
Leu Ala Thr Ala Leu Phe Thr Thr Val Glu Asp Val Ile Asn Thr Phe
                85                  90                  95 atc gat cca cct tca cgt cct tcc gtt gat cca aaa cat gtc ctc tct       336
Ile Asp Pro Pro Ser Arg Pro Ser Val Asp Pro Lys His Val Leu Ser
            100                 105                 110 gat aac ttc gct cct gtc ctc gac gag ctt cct cca aca gac tgt gaa       384
Asp Asn Phe Ala Pro Val Leu Asp Glu Leu Pro Pro Thr Asp Cys Glu
        115                 120                 125 atc atc cac ggc act ctt cca ctg tca ctt aac ggc gct tac atc cgt       432
Ile Ile His Gly Thr Leu Pro Leu Ser Leu Asn Gly Ala Tyr Ile Arg
    130                 135                 140 aac ggt cca aat cca cag ttt ctc cct cgt ggt cct tac cat ctc ttc       480
Asn Gly Pro Asn Pro Gln Phe Leu Pro Arg Gly Pro Tyr His Leu Phe
145                 150                 155                 160 gac ggc gac ggt atg ctt cac gcc ata aaa atc cac aac ggt aaa gcc       528
Asp Gly Asp Gly Met Leu His Ala Ile Lys Ile His Asn Gly Lys Ala
                165                 170                 175 act ctc tgt agc aga tac gtc aag act tat aaa tac aac gtc gag aaa       576
Thr Leu Cys Ser Arg Tyr Val Lys Thr Tyr Lys Tyr Asn Val Glu Lys
            180                 185                 190 caa acc gga gct ccg gtt atg cct aac gtg ttt tcc gga ttc aac ggt       624
Gln Thr Gly Ala Pro Val Met Pro Asn Val Phe Ser Gly Phe Asn Gly
        195                 200                 205 gta acg gcg tca gta gct cgt gga gct tta acg gca gct agg gtt tta       672
Val Thr Ala Ser Val Ala Arg Gly Ala Leu Thr Ala Ala Arg Val Leu
    210                 215                 220 acc gga cag tat aat ccg gtt aac ggc att ggt tta gct aat aca agt       720
Thr Gly Gln Tyr Asn Pro Val Asn Gly Ile Gly Leu Ala Asn Thr Ser
225                 230                 235                 240 cta gct ttc ttc agt aac cgt ctc ttt gct tta ggt gaa tct gat tta       768
Leu Ala Phe Phe Ser Asn Arg Leu Phe Ala Leu Gly Glu Ser Asp Leu
                245                 250                 255 ccc tac gcc gtc cga tta acc gaa tca gga gat att gaa acg atc gga       816
Pro Tyr Ala Val Arg Leu Thr Glu Ser Gly Asp Ile Glu Thr Ile Gly
            260                 265                 270
```

-continued

| | |
|---|---|
| cgg tac gat ttc gac ggg aaa tta gcg atg agt atg aca gct cat cct<br>Arg Tyr Asp Phe Asp Gly Lys Leu Ala Met Ser Met Thr Ala His Pro<br>275 280 285 | 864 |
| aaa acc gat cca ata acc gga gaa act ttc gct ttc cgg tac ggt ccg<br>Lys Thr Asp Pro Ile Thr Gly Glu Thr Phe Ala Phe Arg Tyr Gly Pro<br>290 295 300 | 912 |
| gtt cca ccg ttt tta aca tat ttc cgg ttt gat tcc gcc ggg aaa aaa<br>Val Pro Pro Phe Leu Thr Tyr Phe Arg Phe Asp Ser Ala Gly Lys Lys<br>305 310 315 320 | 960 |
| caa aga gac gtt ccg ata ttc tcg atg acg tct ccg tcg ttt ctc cat<br>Gln Arg Asp Val Pro Ile Phe Ser Met Thr Ser Pro Ser Phe Leu His<br>325 330 335 | 1008 |
| gac ttc gcg atc acg aaa cgt cac gcg att ttc gca gag att cag ctt<br>Asp Phe Ala Ile Thr Lys Arg His Ala Ile Phe Ala Glu Ile Gln Leu<br>340 345 350 | 1056 |
| ggc atg agg atg aac atg ttg gat ttg gtt ctc gaa ggt ggt tct ccg<br>Gly Met Arg Met Asn Met Leu Asp Leu Val Leu Glu Gly Gly Ser Pro<br>355 360 365 | 1104 |
| gtt ggt act gat aac gga aaa act cca agg ctt gga gtg att cct aag<br>Val Gly Thr Asp Asn Gly Lys Thr Pro Arg Leu Gly Val Ile Pro Lys<br>370 375 380 | 1152 |
| tac gcc gga gat gag tcg gag atg aaa tgg ttc gaa gtt cct gga ttc<br>Tyr Ala Gly Asp Glu Ser Glu Met Lys Trp Phe Glu Val Pro Gly Phe<br>385 390 395 400 | 1200 |
| aat atc att cac gct att aat gct tgg gat gaa gat gat gga aac agc<br>Asn Ile Ile His Ala Ile Asn Ala Trp Asp Glu Asp Asp Gly Asn Ser<br>405 410 415 | 1248 |
| gtc gtt ttg att gca ccg aat att atg tcg att gaa cat act tta gag<br>Val Val Leu Ile Ala Pro Asn Ile Met Ser Ile Glu His Thr Leu Glu<br>420 425 430 | 1296 |
| agg atg gat ctg gtt cat gct ttg gtg gag aag gtg aag atc gat ctc<br>Arg Met Asp Leu Val His Ala Leu Val Glu Lys Val Lys Ile Asp Leu<br>435 440 445 | 1344 |
| gtc acc ggg att gtg aga cgt cat ccg atc tca gcg agg aat ctc gat<br>Val Thr Gly Ile Val Arg Arg His Pro Ile Ser Ala Arg Asn Leu Asp<br>450 455 460 | 1392 |
| ttc gct gtg att aat ccg gcg ttt ctc ggg aga tgt agc agg tac gtt<br>Phe Ala Val Ile Asn Pro Ala Phe Leu Gly Arg Cys Ser Arg Tyr Val<br>465 470 475 480 | 1440 |
| tac gcg gcg att gga gat ccg atg ccg aag atc tcc ggt gtg gtg aag<br>Tyr Ala Ala Ile Gly Asp Pro Met Pro Lys Ile Ser Gly Val Val Lys<br>485 490 495 | 1488 |
| ctt gat gtg tct aaa gga gat cgg gat gat tgt acg gtg gcc cgt aga<br>Leu Asp Val Ser Lys Gly Asp Arg Asp Asp Cys Thr Val Ala Arg Arg<br>500 505 510 | 1536 |
| atg tac ggt tca ggt tgt tac ggc gga gaa ccg ttt ttc gta gct agg<br>Met Tyr Gly Ser Gly Cys Tyr Gly Gly Glu Pro Phe Phe Val Ala Arg<br>515 520 525 | 1584 |
| gat cct ggt aat ccg gag gcg gag gag gat gat ggt tat gtg gtg acg<br>Asp Pro Gly Asn Pro Glu Ala Glu Glu Asp Asp Gly Tyr Val Val Thr<br>530 535 540 | 1632 |
| tat gtt cac gat gaa gtg act gga gaa tcg aag ttt ctg gtg atg gac<br>Tyr Val His Asp Glu Val Thr Gly Glu Ser Lys Phe Leu Val Met Asp<br>545 550 555 560 | 1680 |
| gct aaa tcg ccg gag ctt gaa atc gtc gcc gcc gtg agg ttg ccg cga<br>Ala Lys Ser Pro Glu Leu Glu Ile Val Ala Ala Val Arg Leu Pro Arg<br>565 570 575 | 1728 |
| agg gtt ccg tac gga ttc cat ggg tta ttt gtc aag gaa agt gac ctt<br>Arg Val Pro Tyr Gly Phe His Gly Leu Phe Val Lys Glu Ser Asp Leu | 1776 |

```
                    580                 585                 590
aat aag ctt taa                                                             1788
Asn Lys Leu
     595

<210> SEQ ID NO 4
<211> LENGTH: 595
<212> TYPE: PRT
<213> ORGANISM: Arabidopsis thaliana

<400> SEQUENCE: 4

Met Asp Ser Val Ser Ser Ser Phe Leu Ser Ser Thr Phe Ser Leu
 1               5                  10                  15

His His Ser Leu Leu Arg Arg Arg Ser Ser Pro Thr Leu Leu Arg
                20                  25                  30

Ile Asn Ser Ala Val Val Glu Glu Arg Ser Pro Ile Thr Asn Pro Ser
                35                  40                  45

Asp Asn Asn Asp Arg Arg Asn Lys Pro Lys Thr Leu His Asn Arg Thr
     50                  55                  60

Asn His Thr Leu Val Ser Ser Pro Pro Lys Leu Arg Pro Glu Met Thr
 65                  70                  75                  80

Leu Ala Thr Ala Leu Phe Thr Thr Val Glu Asp Val Ile Asn Thr Phe
                85                  90                  95

Ile Asp Pro Pro Ser Arg Pro Ser Val Asp Pro Lys His Val Leu Ser
               100                 105                 110

Asp Asn Phe Ala Pro Val Leu Asp Glu Leu Pro Pro Thr Asp Cys Glu
               115                 120                 125

Ile Ile His Gly Thr Leu Pro Leu Ser Leu Asn Gly Ala Tyr Ile Arg
     130                 135                 140

Asn Gly Pro Asn Pro Gln Phe Leu Pro Arg Gly Pro Tyr His Leu Phe
145                 150                 155                 160

Asp Gly Asp Gly Met Leu His Ala Ile Lys Ile His Asn Gly Lys Ala
                165                 170                 175

Thr Leu Cys Ser Arg Tyr Val Lys Thr Tyr Lys Tyr Asn Val Glu Lys
                180                 185                 190

Gln Thr Gly Ala Pro Val Met Pro Asn Val Phe Ser Gly Phe Asn Gly
                195                 200                 205

Val Thr Ala Ser Val Ala Arg Gly Ala Leu Thr Ala Ala Arg Val Leu
     210                 215                 220

Thr Gly Gln Tyr Asn Pro Val Asn Gly Ile Gly Leu Ala Asn Thr Ser
225                 230                 235                 240

Leu Ala Phe Phe Ser Asn Arg Leu Phe Ala Leu Gly Glu Ser Asp Leu
                245                 250                 255

Pro Tyr Ala Val Arg Leu Thr Glu Ser Gly Asp Ile Glu Thr Ile Gly
                260                 265                 270

Arg Tyr Asp Phe Asp Gly Lys Leu Ala Met Ser Met Thr Ala His Pro
     275                 280                 285

Lys Thr Asp Pro Ile Thr Gly Glu Thr Phe Ala Phe Arg Tyr Gly Pro
     290                 295                 300

Val Pro Pro Phe Leu Thr Tyr Phe Arg Phe Asp Ser Ala Gly Lys Lys
305                 310                 315                 320

Gln Arg Asp Val Pro Ile Phe Ser Met Thr Ser Pro Ser Phe Leu His
                325                 330                 335

Asp Phe Ala Ile Thr Lys Arg His Ala Ile Phe Ala Glu Ile Gln Leu
                340                 345                 350
```

```
Gly Met Arg Met Asn Met Leu Asp Leu Val Leu Glu Gly Gly Ser Pro
            355                 360                 365
Val Gly Thr Asp Asn Gly Lys Thr Pro Arg Leu Gly Val Ile Pro Lys
        370                 375                 380
Tyr Ala Gly Asp Glu Ser Glu Met Lys Trp Phe Glu Val Pro Gly Phe
385                 390                 395                 400
Asn Ile Ile His Ala Ile Asn Ala Trp Asp Glu Asp Gly Asn Ser
                405                 410                 415
Val Val Leu Ile Ala Pro Asn Ile Met Ser Ile Glu His Thr Leu Glu
            420                 425                 430
Arg Met Asp Leu Val His Ala Leu Val Glu Lys Val Lys Ile Asp Leu
        435                 440                 445
Val Thr Gly Ile Val Arg Arg His Pro Ile Ser Ala Arg Asn Leu Asp
    450                 455                 460
Phe Ala Val Ile Asn Pro Ala Phe Leu Gly Arg Cys Ser Arg Tyr Val
465                 470                 475                 480
Tyr Ala Ala Ile Gly Asp Pro Met Pro Lys Ile Ser Gly Val Val Lys
                485                 490                 495
Leu Asp Val Ser Lys Gly Asp Arg Asp Asp Cys Thr Val Ala Arg Arg
            500                 505                 510
Met Tyr Gly Ser Gly Cys Tyr Gly Gly Glu Pro Phe Phe Val Ala Arg
        515                 520                 525
Asp Pro Gly Asn Pro Glu Ala Glu Glu Asp Gly Tyr Val Val Thr
    530                 535                 540
Tyr Val His Asp Glu Val Thr Gly Glu Ser Lys Phe Leu Val Met Asp
545                 550                 555                 560
Ala Lys Ser Pro Glu Leu Glu Ile Val Ala Ala Val Arg Leu Pro Arg
                565                 570                 575
Arg Val Pro Tyr Gly Phe His Gly Leu Phe Val Lys Glu Ser Asp Leu
            580                 585                 590
Asn Lys Leu
        595

<210> SEQ ID NO 5
<211> LENGTH: 1800
<212> TYPE: DNA
<213> ORGANISM: Arabidopsis thaliana
<220> FEATURE:
<221> NAME/KEY: CDS
<222> LOCATION: (1)..(1797)

<400> SEQUENCE: 5 atg gct tct ttc acg gca acg gct gcg gtt tct ggg aga tgg ctt ggt    48
Met Ala Ser Phe Thr Ala Thr Ala Ala Val Ser Gly Arg Trp Leu Gly
  1               5                  10                  15 ggc aat cat act cag ccg cca tta tcg tct tct caa agc tcc gac ttg    96
Gly Asn His Thr Gln Pro Pro Leu Ser Ser Ser Gln Ser Ser Asp Leu
             20                  25                  30 agt tat tgt agc tcc tta cct atg gcc agt cgt gtc aca cgt aag ctc   144
Ser Tyr Cys Ser Ser Leu Pro Met Ala Ser Arg Val Thr Arg Lys Leu
         35                  40                  45 aat gtt tca tct gcg ctt cac act cct cca gct ctt cat ttc cct aag   192
Asn Val Ser Ser Ala Leu His Thr Pro Pro Ala Leu His Phe Pro Lys
     50                  55                  60 caa tca tca aac tct ccc gcc att gtt gtt aag ccc aaa gcc aaa gaa   240
Gln Ser Ser Asn Ser Pro Ala Ile Val Val Lys Pro Lys Ala Lys Glu
 65                  70                  75                  80
```

| | | | | | | | | | | | | | | | | |
|---|---|---|---|---|---|---|---|---|---|---|---|---|---|---|---|---|
| tcc | aac | act | aaa | cag | atg | aat | ttg | ttc | cag | aga | gcg | gcg | gcg | gca | gcg | 288 |
| Ser | Asn | Thr | Lys | Gln | Met | Asn | Leu | Phe | Gln | Arg | Ala | Ala | Ala | Ala | Ala | |
| | | | | 85 | | | | | 90 | | | | | 95 | | |
| ttg | gac | gcg | gcg | gag | ggt | ttc | ctt | gtc | agc | cac | gag | aag | cta | cac | ccg | 336 |
| Leu | Asp | Ala | Ala | Glu | Gly | Phe | Leu | Val | Ser | His | Glu | Lys | Leu | His | Pro | |
| | | | 100 | | | | | 105 | | | | | 110 | | | |
| ctt | cct | aaa | acg | gct | gat | cct | agt | gtt | cag | atc | gcc | gga | aat | ttt | gct | 384 |
| Leu | Pro | Lys | Thr | Ala | Asp | Pro | Ser | Val | Gln | Ile | Ala | Gly | Asn | Phe | Ala | |
| | | | 115 | | | | | 120 | | | | | 125 | | | |
| ccg | gtg | aat | gaa | cag | ccc | gtc | cgg | cgt | aat | ctt | ccg | gtg | gtc | gga | aaa | 432 |
| Pro | Val | Asn | Glu | Gln | Pro | Val | Arg | Arg | Asn | Leu | Pro | Val | Val | Gly | Lys | |
| | 130 | | | | | 135 | | | | | 140 | | | | | |
| ctt | ccc | gat | tcc | atc | aaa | gga | gtg | tat | gtg | cgc | aac | gga | gct | aac | cca | 480 |
| Leu | Pro | Asp | Ser | Ile | Lys | Gly | Val | Tyr | Val | Arg | Asn | Gly | Ala | Asn | Pro | |
| 145 | | | | | 150 | | | | | 155 | | | | | 160 | |
| ctt | cac | gag | ccg | gtg | aca | ggt | cac | cac | ttc | ttc | gac | gga | gac | ggt | atg | 528 |
| Leu | His | Glu | Pro | Val | Thr | Gly | His | His | Phe | Phe | Asp | Gly | Asp | Gly | Met | |
| | | | | 165 | | | | | 170 | | | | | 175 | | |
| gtt | cac | gcc | gtc | aaa | ttc | gaa | cac | ggt | tca | gct | agc | tac | gct | tgc | cgg | 576 |
| Val | His | Ala | Val | Lys | Phe | Glu | His | Gly | Ser | Ala | Ser | Tyr | Ala | Cys | Arg | |
| | | | 180 | | | | | 185 | | | | | 190 | | | |
| ttt | act | cag | act | aac | cgg | ttt | gtt | cag | gaa | cgt | caa | ttg | ggt | cga | ccg | 624 |
| Phe | Thr | Gln | Thr | Asn | Arg | Phe | Val | Gln | Glu | Arg | Gln | Leu | Gly | Arg | Pro | |
| | | | 195 | | | | | 200 | | | | | 205 | | | |
| gtt | ttc | ccc | aaa | gcc | atc | ggt | gag | ctt | cac | ggc | cac | acc | ggt | att | gcc | 672 |
| Val | Phe | Pro | Lys | Ala | Ile | Gly | Glu | Leu | His | Gly | His | Thr | Gly | Ile | Ala | |
| | | 210 | | | | | 215 | | | | | 220 | | | | |
| cga | ctc | atg | cta | ttc | tac | gcc | aga | gct | gca | gcc | ggt | ata | gtc | gac | ccg | 720 |
| Arg | Leu | Met | Leu | Phe | Tyr | Ala | Arg | Ala | Ala | Ala | Gly | Ile | Val | Asp | Pro | |
| 225 | | | | | 230 | | | | | 235 | | | | | 240 | |
| gca | cac | gga | acc | ggt | gta | gct | aac | gcc | ggt | ttg | gtc | tat | ttc | aat | ggc | 768 |
| Ala | His | Gly | Thr | Gly | Val | Ala | Asn | Ala | Gly | Leu | Val | Tyr | Phe | Asn | Gly | |
| | | | 245 | | | | | 250 | | | | | 255 | | | |
| cgg | tta | ttg | gct | atg | tcg | gag | gat | gat | tta | cct | tac | caa | gtt | cag | atc | 816 |
| Arg | Leu | Leu | Ala | Met | Ser | Glu | Asp | Asp | Leu | Pro | Tyr | Gln | Val | Gln | Ile | |
| | | | 260 | | | | | 265 | | | | | 270 | | | |
| act | ccc | aat | gga | gat | tta | aaa | acc | gtt | ggt | cgg | ttc | gat | ttt | gat | gga | 864 |
| Thr | Pro | Asn | Gly | Asp | Leu | Lys | Thr | Val | Gly | Arg | Phe | Asp | Phe | Asp | Gly | |
| | | | 275 | | | | | 280 | | | | | 285 | | | |
| caa | tta | gaa | tcc | aca | atg | att | gcc | cac | ccg | aaa | gtc | gac | ccg | gaa | tcc | 912 |
| Gln | Leu | Glu | Ser | Thr | Met | Ile | Ala | His | Pro | Lys | Val | Asp | Pro | Glu | Ser | |
| | | 290 | | | | | 295 | | | | | 300 | | | | |
| ggt | gaa | ctc | ttc | gct | tta | agc | tac | gac | gtc | gtt | tca | aag | cct | tac | cta | 960 |
| Gly | Glu | Leu | Phe | Ala | Leu | Ser | Tyr | Asp | Val | Val | Ser | Lys | Pro | Tyr | Leu | |
| 305 | | | | | 310 | | | | | 315 | | | | | 320 | |
| aaa | tac | ttc | cga | ttc | tca | ccg | gac | gga | act | aaa | tca | ccg | gac | gtc | gag | 1008 |
| Lys | Tyr | Phe | Arg | Phe | Ser | Pro | Asp | Gly | Thr | Lys | Ser | Pro | Asp | Val | Glu | |
| | | | 325 | | | | | 330 | | | | | 335 | | | |
| att | cag | ctt | gat | cag | cca | acg | atg | atg | cac | gat | ttc | gcg | att | aca | gag | 1056 |
| Ile | Gln | Leu | Asp | Gln | Pro | Thr | Met | Met | His | Asp | Phe | Ala | Ile | Thr | Glu | |
| | | | 340 | | | | | 345 | | | | | 350 | | | |
| aac | ttc | gtc | gtc | gta | cct | gac | cag | caa | gtc | gtt | ttc | aag | ctg | ccg | gag | 1104 |
| Asn | Phe | Val | Val | Val | Pro | Asp | Gln | Gln | Val | Val | Phe | Lys | Leu | Pro | Glu | |
| | | | 355 | | | | | 360 | | | | | 365 | | | |
| atg | atc | cgc | ggt | ggg | tct | ccg | gtg | gtt | tac | gac | aag | aac | aag | gtc | gca | 1152 |
| Met | Ile | Arg | Gly | Gly | Ser | Pro | Val | Val | Tyr | Asp | Lys | Asn | Lys | Val | Ala | |
| | | 370 | | | | | 375 | | | | | 380 | | | | |
| aga | ttc | ggg | att | tta | gac | aaa | tac | gcc | gaa | gat | tca | tcg | aac | att | aag | 1200 |
| Arg | Phe | Gly | Ile | Leu | Asp | Lys | Tyr | Ala | Glu | Asp | Ser | Ser | Asn | Ile | Lys | |

```
                    385                 390                 395                 400 tgg att gat gct cca gat tgc ttc tgc ttc cat ctc tgg aac gct tgg       1248
Trp Ile Asp Ala Pro Asp Cys Phe Cys Phe His Leu Trp Asn Ala Trp
                405                 410                 415 gaa gag cca gaa aca gat gaa gtc gtc gtg ata ggg tcc tgt atg act       1296
Glu Glu Pro Glu Thr Asp Glu Val Val Val Ile Gly Ser Cys Met Thr
            420                 425                 430 cca cca gac tca att ttc aac gag tct gac gag aat ctc aag agt gtc       1344
Pro Pro Asp Ser Ile Phe Asn Glu Ser Asp Glu Asn Leu Lys Ser Val
        435                 440                 445 ctg tct gaa atc cgc ctg aat ctc aaa acc ggt gaa tca act cgc cgt       1392
Leu Ser Glu Ile Arg Leu Asn Leu Lys Thr Gly Glu Ser Thr Arg Arg
    450                 455                 460 ccg atc atc tcc aac gaa gat caa caa gtc aac ctc gaa gca ggg atg       1440
Pro Ile Ile Ser Asn Glu Asp Gln Gln Val Asn Leu Glu Ala Gly Met
465                 470                 475                 480 gtc aac aga aac atg ctc ggc cgt aaa acc aaa ttc gct tac ttg gct       1488
Val Asn Arg Asn Met Leu Gly Arg Lys Thr Lys Phe Ala Tyr Leu Ala
                485                 490                 495 tta gcc gag ccg tgg cct aaa gtc tca gga ttc gct aaa gtt gat ctc       1536
Leu Ala Glu Pro Trp Pro Lys Val Ser Gly Phe Ala Lys Val Asp Leu
            500                 505                 510 act act gga gaa gtt aag aaa cat ctt tac ggc gat aac cgt tac gga       1584
Thr Thr Gly Glu Val Lys Lys His Leu Tyr Gly Asp Asn Arg Tyr Gly
        515                 520                 525 gga gag cct ctg ttt ctc ccc gga gaa gga gga gag gaa gac gaa gga       1632
Gly Glu Pro Leu Phe Leu Pro Gly Glu Gly Gly Glu Glu Asp Glu Gly
    530                 535                 540 tac atc ctc tgt ttc gtt cac gac gag aag aca tgg aaa tcg gag tta       1680
Tyr Ile Leu Cys Phe Val His Asp Glu Lys Thr Trp Lys Ser Glu Leu
545                 550                 555                 560 cag ata gtt aac gcc gtt agc tta gag gtt gaa gca acg gtt aaa ctt       1728
Gln Ile Val Asn Ala Val Ser Leu Glu Val Glu Ala Thr Val Lys Leu
                565                 570                 575 ccg tca agg gtt ccg tac gga ttt cac ggt aca ttc atc gga gcc gat       1776
Pro Ser Arg Val Pro Tyr Gly Phe His Gly Thr Phe Ile Gly Ala Asp
            580                 585                 590 gat ttg gcg aag cag gtc gtg tga                                       1800
Asp Leu Ala Lys Gln Val Val
        595

<210> SEQ ID NO 6
<211> LENGTH: 599
<212> TYPE: PRT
<213> ORGANISM: Arabidopsis thaliana

<400> SEQUENCE: 6

Met Ala Ser Phe Thr Ala Thr Ala Ala Val Ser Gly Arg Trp Leu Gly
1               5                   10                  15

Gly Asn His Thr Gln Pro Pro Leu Ser Ser Gln Ser Ser Asp Leu
            20                  25                  30

Ser Tyr Cys Ser Ser Leu Pro Met Ala Ser Arg Val Thr Arg Lys Leu
        35                  40                  45

Asn Val Ser Ser Ala Leu His Thr Pro Pro Ala Leu His Phe Pro Lys
    50                  55                  60

Gln Ser Ser Asn Ser Pro Ala Ile Val Val Lys Pro Lys Ala Lys Glu
65                  70                  75                  80

Ser Asn Thr Lys Gln Met Asn Leu Phe Gln Arg Ala Ala Ala Ala Ala
                85                  90                  95
```

```
Leu Asp Ala Ala Glu Gly Phe Leu Val Ser His Glu Lys Leu His Pro
                100                 105                 110

Leu Pro Lys Thr Ala Asp Pro Ser Val Gln Ile Ala Gly Asn Phe Ala
            115                 120                 125

Pro Val Asn Glu Gln Pro Val Arg Arg Asn Leu Pro Val Val Gly Lys
130                 135                 140

Leu Pro Asp Ser Ile Lys Gly Val Tyr Val Arg Asn Gly Ala Asn Pro
145                 150                 155                 160

Leu His Glu Pro Val Thr Gly His His Phe Asp Gly Asp Gly Met
                165                 170                 175

Val His Ala Val Lys Phe Glu His Gly Ser Ala Ser Tyr Ala Cys Arg
            180                 185                 190

Phe Thr Gln Thr Asn Arg Phe Val Gln Glu Arg Gln Leu Gly Arg Pro
            195                 200                 205

Val Phe Pro Lys Ala Ile Gly Glu Leu His Gly His Thr Gly Ile Ala
210                 215                 220

Arg Leu Met Leu Phe Tyr Ala Arg Ala Ala Gly Ile Val Asp Pro
225                 230                 235                 240

Ala His Gly Thr Gly Val Ala Asn Ala Gly Leu Val Tyr Phe Asn Gly
                245                 250                 255

Arg Leu Leu Ala Met Ser Glu Asp Asp Leu Pro Tyr Gln Val Gln Ile
            260                 265                 270

Thr Pro Asn Gly Asp Leu Lys Thr Val Gly Arg Phe Asp Phe Asp Gly
            275                 280                 285

Gln Leu Glu Ser Thr Met Ile Ala His Pro Lys Val Asp Pro Glu Ser
        290                 295                 300

Gly Glu Leu Phe Ala Leu Ser Tyr Asp Val Val Ser Lys Pro Tyr Leu
305                 310                 315                 320

Lys Tyr Phe Arg Phe Ser Pro Asp Gly Thr Lys Ser Pro Asp Val Glu
                325                 330                 335

Ile Gln Leu Asp Gln Pro Thr Met Met His Asp Phe Ala Ile Thr Glu
            340                 345                 350

Asn Phe Val Val Val Pro Asp Gln Gln Val Val Phe Lys Leu Pro Glu
        355                 360                 365

Met Ile Arg Gly Gly Ser Pro Val Val Tyr Asp Lys Asn Lys Val Ala
370                 375                 380

Arg Phe Gly Ile Leu Asp Lys Tyr Ala Glu Asp Ser Ser Asn Ile Lys
385                 390                 395                 400

Trp Ile Asp Ala Pro Asp Cys Phe Cys Phe His Leu Trp Asn Ala Trp
                405                 410                 415

Glu Glu Pro Glu Thr Asp Glu Val Val Val Ile Gly Ser Cys Met Thr
            420                 425                 430

Pro Pro Asp Ser Ile Phe Asn Glu Ser Asp Glu Asn Leu Lys Ser Val
            435                 440                 445

Leu Ser Glu Ile Arg Leu Asn Leu Lys Thr Gly Glu Ser Thr Arg Arg
450                 455                 460

Pro Ile Ile Ser Asn Glu Asp Gln Gln Val Asn Leu Glu Ala Gly Met
465                 470                 475                 480

Val Asn Arg Asn Met Leu Gly Arg Lys Thr Lys Phe Ala Tyr Leu Ala
                485                 490                 495

Leu Ala Glu Pro Trp Pro Lys Val Ser Gly Phe Ala Lys Val Asp Leu
            500                 505                 510
```

```
Thr Thr Gly Glu Val Lys Lys His Leu Tyr Gly Asp Asn Arg Tyr Gly
        515                 520                 525

Gly Glu Pro Leu Phe Leu Pro Gly Glu Gly Glu Glu Asp Glu Gly
        530                 535                 540

Tyr Ile Leu Cys Phe Val His Asp Glu Lys Thr Trp Lys Ser Glu Leu
545                 550                 555                 560

Gln Ile Val Asn Ala Val Ser Leu Glu Val Glu Ala Thr Val Lys Leu
                565                 570                 575

Pro Ser Arg Val Pro Tyr Gly Phe His Gly Thr Phe Ile Gly Ala Asp
                580                 585                 590

Asp Leu Ala Lys Gln Val Val
        595

<210> SEQ ID NO 7
<211> LENGTH: 1617
<212> TYPE: DNA
<213> ORGANISM: Arabidopsis thaliana
<220> FEATURE:
<221> NAME/KEY: CDS
<222> LOCATION: (1)..(1614)

<400> SEQUENCE: 7
```

| | | | | | | | | | | | | | | | | |
|---|---|---|---|---|---|---|---|---|---|---|---|---|---|---|---|---|
| atg | gcg | gag | aaa | ctc | agt | gat | ggc | agc | agc | atc | atc | tca | gtc | cat | cct | 48 |
| Met | Ala | Glu | Lys | Leu | Ser | Asp | Gly | Ser | Ser | Ile | Ile | Ser | Val | His | Pro | |
| 1 | | | | 5 | | | | | 10 | | | | | 15 | | |
| aga | ccc | tcc | aag | ggt | ttc | tcc | tcg | aag | ctt | ctc | gat | ctt | ctc | gag | aga | 96 |
| Arg | Pro | Ser | Lys | Gly | Phe | Ser | Ser | Lys | Leu | Leu | Asp | Leu | Leu | Glu | Arg | |
| | | | 20 | | | | | 25 | | | | | 30 | | | |
| ctt | gtt | gtc | aag | ctc | atg | cac | gat | gct | tct | ctc | cct | ctc | cac | tac | ctc | 144 |
| Leu | Val | Val | Lys | Leu | Met | His | Asp | Ala | Ser | Leu | Pro | Leu | His | Tyr | Leu | |
| | | 35 | | | | | 40 | | | | | 45 | | | | |
| tca | ggc | aac | ttc | gct | ccc | atc | cgt | gat | gaa | act | cct | ccc | gtc | aag | gat | 192 |
| Ser | Gly | Asn | Phe | Ala | Pro | Ile | Arg | Asp | Glu | Thr | Pro | Pro | Val | Lys | Asp | |
| | 50 | | | | | 55 | | | | | 60 | | | | | |
| ctc | ccc | gtc | cat | gga | ttt | ctt | ccc | gaa | tgc | ttg | aat | ggt | gaa | ttt | gtg | 240 |
| Leu | Pro | Val | His | Gly | Phe | Leu | Pro | Glu | Cys | Leu | Asn | Gly | Glu | Phe | Val | |
| 65 | | | | 70 | | | | | 75 | | | | | 80 | | |
| agg | gtt | ggt | cca | aac | ccc | aag | ttt | gat | gct | gtc | gct | gga | tat | cac | tgg | 288 |
| Arg | Val | Gly | Pro | Asn | Pro | Lys | Phe | Asp | Ala | Val | Ala | Gly | Tyr | His | Trp | |
| | | | 85 | | | | | 90 | | | | | 95 | | | |
| ttt | gat | gga | gat | ggg | atg | att | cat | ggg | gta | cgc | atc | aaa | gat | ggg | aaa | 336 |
| Phe | Asp | Gly | Asp | Gly | Met | Ile | His | Gly | Val | Arg | Ile | Lys | Asp | Gly | Lys | |
| | | | 100 | | | | | 105 | | | | | 110 | | | |
| gct | act | tat | gtt | tct | cga | tat | gtt | aag | aca | tca | cgt | ctt | aag | cag | gaa | 384 |
| Ala | Thr | Tyr | Val | Ser | Arg | Tyr | Val | Lys | Thr | Ser | Arg | Leu | Lys | Gln | Glu | |
| | | 115 | | | | | 120 | | | | | 125 | | | | |
| gag | ttc | ttc | gga | gct | gcc | aaa | ttc | atg | aag | att | ggt | gac | ctt | aag | ggg | 432 |
| Glu | Phe | Phe | Gly | Ala | Ala | Lys | Phe | Met | Lys | Ile | Gly | Asp | Leu | Lys | Gly | |
| | 130 | | | | | 135 | | | | | 140 | | | | | |
| ttt | ttc | gga | ttg | cta | atg | gtc | aat | gtc | caa | cag | ctg | aga | acg | aag | ctc | 480 |
| Phe | Phe | Gly | Leu | Leu | Met | Val | Asn | Val | Gln | Gln | Leu | Arg | Thr | Lys | Leu | |
| 145 | | | | 150 | | | | | 155 | | | | | 160 | | |
| aaa | ata | ttg | gac | aac | act | tat | gga | aat | gga | act | gcc | aat | aca | gca | ctc | 528 |
| Lys | Ile | Leu | Asp | Asn | Thr | Tyr | Gly | Asn | Gly | Thr | Ala | Asn | Thr | Ala | Leu | |
| | | | 165 | | | | | 170 | | | | | 175 | | | |
| gta | tat | cac | cat | gga | aaa | ctt | cta | gca | tta | cag | gag | gca | gat | aag | ccg | 576 |
| Val | Tyr | His | His | Gly | Lys | Leu | Leu | Ala | Leu | Gln | Glu | Ala | Asp | Lys | Pro | |
| | | | 180 | | | | | 185 | | | | | 190 | | | |
| tac | gtc | atc | aaa | gtt | ttg | gaa | gat | gga | gac | ctg | caa | act | ctt | ggt | ata | 624 |
| Tyr | Val | Ile | Lys | Val | Leu | Glu | Asp | Gly | Asp | Leu | Gln | Thr | Leu | Gly | Ile | |

-continued

|   |   |   | 195 |   |   |   |   | 200 |   |   |   |   | 205 |   |   |      |
|---|---|---|---|---|---|---|---|---|---|---|---|---|---|---|---|---|
| ata | gat | tat | gac | aag | aga | ttg | acc | cac | tcc | ttc | act | gct | cac | cca | aaa | 672 |
| Ile | Asp | Tyr | Asp | Lys | Arg | Leu | Thr | His | Ser | Phe | Thr | Ala | His | Pro | Lys |     |
|     | 210 |     |     |     | 215 |     |     |     |     | 220 |     |     |     |     |     |     |

| gtt | gac | ccg | gtt | acg | ggt | gaa | atg | ttt | aca | ttc | ggc | tat | tcg | cat | acg | 720 |
| Val | Asp | Pro | Val | Thr | Gly | Glu | Met | Phe | Thr | Phe | Gly | Tyr | Ser | His | Thr |     |
| 225 |     |     |     |     | 230 |     |     |     |     | 235 |     |     |     |     | 240 |     |

| cca | cct | tat | ctc | aca | tac | aga | gtt | atc | tcg | aaa | gat | ggc | att | atg | cat | 768 |
| Pro | Pro | Tyr | Leu | Thr | Tyr | Arg | Val | Ile | Ser | Lys | Asp | Gly | Ile | Met | His |     |
|     |     |     |     | 245 |     |     |     |     | 250 |     |     |     |     | 255 |     |     |

| gac | cca | gtc | cca | att | act | ata | tca | gag | cct | atc | atg | atg | cat | gat | ttt | 816 |
| Asp | Pro | Val | Pro | Ile | Thr | Ile | Ser | Glu | Pro | Ile | Met | Met | His | Asp | Phe |     |
|     |     |     | 260 |     |     |     |     | 265 |     |     |     |     | 270 |     |     |     |

| gct | att | act | gag | act | tat | gca | atc | ttc | atg | gat | ctt | cct | atg | cac | ttc | 864 |
| Ala | Ile | Thr | Glu | Thr | Tyr | Ala | Ile | Phe | Met | Asp | Leu | Pro | Met | His | Phe |     |
|     |     | 275 |     |     |     |     | 280 |     |     |     |     | 285 |     |     |     |     |

| agg | cca | aag | gaa | atg | gtg | aaa | gag | aag | aaa | atg | ata | tac | tca | ttt | gat | 912 |
| Arg | Pro | Lys | Glu | Met | Val | Lys | Glu | Lys | Lys | Met | Ile | Tyr | Ser | Phe | Asp |     |
| 290 |     |     |     |     | 295 |     |     |     |     | 300 |     |     |     |     |     |     |

| ccc | aca | aaa | aag | gct | cgt | ttt | ggt | gtt | ctt | cca | cgc | tat | gcc | aag | gat | 960 |
| Pro | Thr | Lys | Lys | Ala | Arg | Phe | Gly | Val | Leu | Pro | Arg | Tyr | Ala | Lys | Asp |     |
| 305 |     |     |     |     | 310 |     |     |     |     | 315 |     |     |     |     | 320 |     |

| gaa | ctt | atg | att | aga | tgg | ttt | gag | ctt | ccc | aac | tgc | ttt | att | ttc | cac | 1008 |
| Glu | Leu | Met | Ile | Arg | Trp | Phe | Glu | Leu | Pro | Asn | Cys | Phe | Ile | Phe | His |      |
|     |     |     |     | 325 |     |     |     |     | 330 |     |     |     |     | 335 |     |      |

| aac | gcc | aat | gct | tgg | gaa | gaa | gag | gat | gaa | gtc | gtc | ctc | atc | act | tgt | 1056 |
| Asn | Ala | Asn | Ala | Trp | Glu | Glu | Glu | Asp | Glu | Val | Val | Leu | Ile | Thr | Cys |      |
|     |     |     | 340 |     |     |     |     | 345 |     |     |     |     | 350 |     |     |      |

| cgt | ctt | gag | aat | cca | gat | ctt | gac | atg | gtc | agt | ggg | aaa | gtg | aaa | gaa | 1104 |
| Arg | Leu | Glu | Asn | Pro | Asp | Leu | Asp | Met | Val | Ser | Gly | Lys | Val | Lys | Glu |      |
|     |     | 355 |     |     |     |     | 360 |     |     |     |     | 365 |     |     |     |      |

| aaa | ctc | gaa | aat | ttt | ggc | aac | gaa | ctg | tac | gaa | atg | aga | ttc | aac | atg | 1152 |
| Lys | Leu | Glu | Asn | Phe | Gly | Asn | Glu | Leu | Tyr | Glu | Met | Arg | Phe | Asn | Met |      |
| 370 |     |     |     |     | 375 |     |     |     |     | 380 |     |     |     |     |     |      |

| aaa | acg | ggc | tca | gct | tct | caa | aaa | aaa | cta | tcc | gca | tct | gcg | gtt | gat | 1200 |
| Lys | Thr | Gly | Ser | Ala | Ser | Gln | Lys | Lys | Leu | Ser | Ala | Ser | Ala | Val | Asp |      |
| 385 |     |     |     |     | 390 |     |     |     |     | 395 |     |     |     |     | 400 |      |

| ttc | ccc | aga | atc | aat | gag | tgc | tac | acc | gga | aag | aaa | cag | aga | tac | gta | 1248 |
| Phe | Pro | Arg | Ile | Asn | Glu | Cys | Tyr | Thr | Gly | Lys | Lys | Gln | Arg | Tyr | Val |      |
|     |     |     |     | 405 |     |     |     |     | 410 |     |     |     |     | 415 |     |      |

| tat | gga | aca | att | ctg | gac | agt | atc | gca | aag | gtt | acc | gga | atc | atc | aag | 1296 |
| Tyr | Gly | Thr | Ile | Leu | Asp | Ser | Ile | Ala | Lys | Val | Thr | Gly | Ile | Ile | Lys |      |
|     |     |     | 420 |     |     |     |     | 425 |     |     |     |     | 430 |     |     |      |

| ttt | gat | ctg | cat | gca | gaa | gct | gag | aca | ggg | aaa | aga | atg | ctg | gaa | gta | 1344 |
| Phe | Asp | Leu | His | Ala | Glu | Ala | Glu | Thr | Gly | Lys | Arg | Met | Leu | Glu | Val |      |
|     |     | 435 |     |     |     |     | 440 |     |     |     |     | 445 |     |     |     |      |

| gga | ggt | aat | atc | aaa | gga | ata | tat | gac | ctg | gga | gaa | ggc | aga | tat | ggt | 1392 |
| Gly | Gly | Asn | Ile | Lys | Gly | Ile | Tyr | Asp | Leu | Gly | Glu | Gly | Arg | Tyr | Gly |      |
|     | 450 |     |     |     |     | 455 |     |     |     |     | 460 |     |     |     |     |      |

| tca | gag | gct | atc | tat | gtt | ccg | cgt | gag | aca | gca | gaa | gaa | gac | gac | ggt | 1440 |
| Ser | Glu | Ala | Ile | Tyr | Val | Pro | Arg | Glu | Thr | Ala | Glu | Glu | Asp | Asp | Gly |      |
| 465 |     |     |     |     | 470 |     |     |     |     | 475 |     |     |     |     | 480 |      |

| tac | ttg | ata | ttc | ttt | gtt | cat | gat | gaa | aac | aca | ggg | aaa | tca | tgc | gtg | 1488 |
| Tyr | Leu | Ile | Phe | Phe | Val | His | Asp | Glu | Asn | Thr | Gly | Lys | Ser | Cys | Val |      |
|     |     |     |     | 485 |     |     |     |     | 490 |     |     |     |     | 495 |     |      |

| act | gtg | ata | gac | gca | aaa | aca | atg | tcg | gct | gaa | ccg | gtg | gca | gtg | gtg | 1536 |
| Thr | Val | Ile | Asp | Ala | Lys | Thr | Met | Ser | Ala | Glu | Pro | Val | Ala | Val | Val |      |
|     |     |     | 500 |     |     |     |     | 505 |     |     |     |     | 510 |     |     |      |

| gag | ctg | ccg | cac | agg | gtc | cca | tat | ggc | ttc | cat | gcc | ttg | ttt | gtt | aca | 1584 |

-continued

```
Glu Leu Pro His Arg Val Pro Tyr Gly Phe His Ala Leu Phe Val Thr
            515                 520                 525 gag gaa caa ctc cag gaa caa act ctt ata taa                         1617
Glu Glu Gln Leu Gln Glu Gln Thr Leu Ile
        530                 535

<210> SEQ ID NO 8
<211> LENGTH: 538
<212> TYPE: PRT
<213> ORGANISM: Arabidopsis thaliana

<400> SEQUENCE: 8

Met Ala Glu Lys Leu Ser Asp Gly Ser Ser Ile Ile Ser Val His Pro
  1               5                  10                  15

Arg Pro Ser Lys Gly Phe Ser Ser Lys Leu Leu Asp Leu Leu Glu Arg
             20                  25                  30

Leu Val Val Lys Leu Met His Asp Ala Ser Leu Pro Leu His Tyr Leu
         35                  40                  45

Ser Gly Asn Phe Ala Pro Ile Arg Asp Glu Thr Pro Pro Val Lys Asp
     50                  55                  60

Leu Pro Val His Gly Phe Leu Pro Glu Cys Leu Asn Gly Glu Phe Val
 65                  70                  75                  80

Arg Val Gly Pro Asn Pro Lys Phe Asp Ala Val Ala Gly Tyr His Trp
                 85                  90                  95

Phe Asp Gly Asp Gly Met Ile His Gly Val Arg Ile Lys Asp Gly Lys
            100                 105                 110

Ala Thr Tyr Val Ser Arg Tyr Val Lys Thr Ser Arg Leu Lys Gln Glu
        115                 120                 125

Glu Phe Phe Gly Ala Ala Lys Phe Met Lys Ile Gly Asp Leu Lys Gly
    130                 135                 140

Phe Phe Gly Leu Leu Met Val Asn Val Gln Gln Leu Arg Thr Lys Leu
145                 150                 155                 160

Lys Ile Leu Asp Asn Thr Tyr Gly Asn Gly Thr Ala Asn Thr Ala Leu
                165                 170                 175

Val Tyr His His Gly Lys Leu Leu Ala Leu Gln Glu Ala Asp Lys Pro
            180                 185                 190

Tyr Val Ile Lys Val Leu Glu Asp Gly Asp Leu Gln Thr Leu Gly Ile
        195                 200                 205

Ile Asp Tyr Asp Lys Arg Leu Thr His Ser Phe Thr Ala His Pro Lys
    210                 215                 220

Val Asp Pro Val Thr Gly Glu Met Phe Thr Phe Gly Tyr Ser His Thr
225                 230                 235                 240

Pro Pro Tyr Leu Thr Tyr Arg Val Ile Ser Lys Asp Gly Ile Met His
                245                 250                 255

Asp Pro Val Pro Ile Thr Ile Ser Glu Pro Ile Met Met His Asp Phe
            260                 265                 270

Ala Ile Thr Glu Thr Tyr Ala Ile Phe Met Asp Leu Pro Met His Phe
        275                 280                 285

Arg Pro Lys Glu Met Val Lys Glu Lys Met Ile Tyr Ser Phe Asp Pro
    290                 295                 300

Pro Thr Lys Lys Ala Arg Phe Gly Val Leu Pro Arg Tyr Ala Lys Asp
305                 310                 315                 320

Glu Leu Met Ile Arg Trp Phe Glu Leu Pro Asn Cys Phe Ile Phe His
                325                 330                 335

Asn Ala Asn Ala Trp Glu Glu Glu Asp Glu Val Val Leu Ile Thr Cys
```

-continued

```
                340                 345                 350
Arg Leu Glu Asn Pro Asp Leu Asp Met Val Ser Gly Lys Val Lys Glu
                355                 360                 365
Lys Leu Glu Asn Phe Gly Asn Glu Leu Tyr Glu Met Arg Phe Asn Met
            370                 375                 380
Lys Thr Gly Ser Ala Ser Gln Lys Lys Leu Ser Ala Ser Ala Val Asp
385                 390                 395                 400
Phe Pro Arg Ile Asn Glu Cys Tyr Thr Gly Lys Lys Gln Arg Tyr Val
                405                 410                 415
Tyr Gly Thr Ile Leu Asp Ser Ile Ala Lys Val Thr Gly Ile Ile Lys
            420                 425                 430
Phe Asp Leu His Ala Glu Ala Glu Thr Gly Lys Arg Met Leu Glu Val
            435                 440                 445
Gly Gly Asn Ile Lys Gly Ile Tyr Asp Leu Gly Glu Gly Arg Tyr Gly
            450                 455                 460
Ser Glu Ala Ile Tyr Val Pro Arg Glu Thr Ala Glu Asp Asp Gly
465                 470                 475                 480
Tyr Leu Ile Phe Phe Val His Asp Glu Asn Thr Gly Lys Ser Cys Val
                485                 490                 495
Thr Val Ile Asp Ala Lys Thr Met Ser Ala Glu Pro Val Ala Val Val
            500                 505                 510
Glu Leu Pro His Arg Val Pro Tyr Gly Phe His Ala Leu Phe Val Thr
            515                 520                 525
Glu Glu Gln Leu Gln Glu Gln Thr Leu Ile
            530                 535

<210> SEQ ID NO 9
<211> LENGTH: 1734
<212> TYPE: DNA
<213> ORGANISM: Arabidopsis thaliana
<220> FEATURE:
<221> NAME/KEY: CDS
<222> LOCATION: (1)..(1731)

<400> SEQUENCE: 9 atg caa cac tct ctt cgt tct gat ctt ctt ccg acg aag act tct cct      48
Met Gln His Ser Leu Arg Ser Asp Leu Leu Pro Thr Lys Thr Ser Pro
1               5                   10                  15 cgt tct cat tta ctt cca caa ccc aaa aat gca aat att tct cga cga      96
Arg Ser His Leu Leu Pro Gln Pro Lys Asn Ala Asn Ile Ser Arg Arg
                20                  25                  30 att ctc att aac cct ttc aag ata ccg aca ctt cct gat ctc act tct     144
Ile Leu Ile Asn Pro Phe Lys Ile Pro Thr Leu Pro Asp Leu Thr Ser
            35                  40                  45 ccg gtt ccg tca ccg gtt aag ctc aaa cca acg tat cca aac tta aac     192
Pro Val Pro Ser Pro Val Lys Leu Lys Pro Thr Tyr Pro Asn Leu Asn
        50                  55                  60 ctt ctt cag aag cta gcg gct acg atg ctc gac aag att gag tcc tct     240
Leu Leu Gln Lys Leu Ala Ala Thr Met Leu Asp Lys Ile Glu Ser Ser
65                  70                  75                  80 atc gtt att cct atg gag cag aat cgc ccg ctt cct aaa ccg acc gac     288
Ile Val Ile Pro Met Glu Gln Asn Arg Pro Leu Pro Lys Pro Thr Asp
                85                  90                  95 ccg gcg gtt caa tta tca ggt aac ttc gct ccg gtt aat gaa tgt ccg     336
Pro Ala Val Gln Leu Ser Gly Asn Phe Ala Pro Val Asn Glu Cys Pro
                100                 105                 110 gtt cag aac ggt tta gaa gtg gtt ggt cag att cct tct tgt cta aaa     384
Val Gln Asn Gly Leu Glu Val Val Gly Gln Ile Pro Ser Cys Leu Lys
```

```
            115                 120                 125
gga gtt tac atc cgt aac ggt gca aac cct atg ttt ccg ccg tta gcc       432
Gly Val Tyr Ile Arg Asn Gly Ala Asn Pro Met Phe Pro Pro Leu Ala
    130                 135                 140 gga cat cat tta ttt gac ggt gac gga atg att cac gcc gtt agt atc       480
Gly His His Leu Phe Asp Gly Asp Gly Met Ile His Ala Val Ser Ile
145                 150                 155                 160 ggt ttt gat aac cag gtt agt tac agc tgc cgg tac act aaa aca aac       528
Gly Phe Asp Asn Gln Val Ser Tyr Ser Cys Arg Tyr Thr Lys Thr Asn
                165                 170                 175 cgg ctt gtt caa gaa acc gcg ctt gga cga tcg gtt ttc cct aaa cca       576
Arg Leu Val Gln Glu Thr Ala Leu Gly Arg Ser Val Phe Pro Lys Pro
            180                 185                 190 atc ggc gag ctt cac ggc cat tcc ggt cta gct cga ctc gct ctc ttc       624
Ile Gly Glu Leu His Gly His Ser Gly Leu Ala Arg Leu Ala Leu Phe
        195                 200                 205 acg gct cga gct ggg atc ggt cta gtg gac ggg aca cgt ggc atg ggc       672
Thr Ala Arg Ala Gly Ile Gly Leu Val Asp Gly Thr Arg Gly Met Gly
    210                 215                 220 gta gct aac gcc ggt gtg gtt ttc ttt aac ggc agg tta tta gcc atg       720
Val Ala Asn Ala Gly Val Val Phe Phe Asn Gly Arg Leu Leu Ala Met
225                 230                 235                 240 tca gaa gat gat ctt cct tac caa gtg aag atc gac ggt caa gga gat       768
Ser Glu Asp Asp Leu Pro Tyr Gln Val Lys Ile Asp Gly Gln Gly Asp
                245                 250                 255 ctt gag acg atc gga cgg ttc gga ttc gat gac cag att gac tct tca       816
Leu Glu Thr Ile Gly Arg Phe Gly Phe Asp Asp Gln Ile Asp Ser Ser
            260                 265                 270 gtg ata gcg cat cct aag gtg gac gcg acc aca gga gat ctc cat aca       864
Val Ile Ala His Pro Lys Val Asp Ala Thr Thr Gly Asp Leu His Thr
        275                 280                 285 ctg agc tac aac gtt ttg aag aaa cct cat ctc agg tat ctt aaa ttc       912
Leu Ser Tyr Asn Val Leu Lys Lys Pro His Leu Arg Tyr Leu Lys Phe
    290                 295                 300 aac acg tgc ggg aaa aag aca cgt gac gtg gag atc acg ctc cct gaa       960
Asn Thr Cys Gly Lys Lys Thr Arg Asp Val Glu Ile Thr Leu Pro Glu
305                 310                 315                 320 cca acg atg att cat gat ttc gcg ata acc gag aat ttt gtc gtt ata      1008
Pro Thr Met Ile His Asp Phe Ala Ile Thr Glu Asn Phe Val Val Ile
                325                 330                 335 ccg gat cag caa atg gta ttc aaa tta tcc gaa atg att cgg ggc ggg      1056
Pro Asp Gln Gln Met Val Phe Lys Leu Ser Glu Met Ile Arg Gly Gly
            340                 345                 350 tca ccc gtt atc tac gtt aaa gaa aaa atg gcg aga ttt gga gtt ttg      1104
Ser Pro Val Ile Tyr Val Lys Glu Lys Met Ala Arg Phe Gly Val Leu
        355                 360                 365 tca aag cag gat ctg acc ggg tcg gat ata aat tgg gtt gat gta ccg      1152
Ser Lys Gln Asp Leu Thr Gly Ser Asp Ile Asn Trp Val Asp Val Pro
    370                 375                 380 gat tgt ttc tgt ttc cat cta tgg aat gcg tgg gaa gag aga acc gaa      1200
Asp Cys Phe Cys Phe His Leu Trp Asn Ala Trp Glu Glu Arg Thr Glu
385                 390                 395                 400 gag gga gac cca gtt atc gtc gta atc ggg tca tgt atg agc cca ccc      1248
Glu Gly Asp Pro Val Ile Val Val Ile Gly Ser Cys Met Ser Pro Pro
                405                 410                 415 gac acg atc ttt agt gaa tca gga gaa cca acc cgg gtt gaa tta agt      1296
Asp Thr Ile Phe Ser Glu Ser Gly Glu Pro Thr Arg Val Glu Leu Ser
            420                 425                 430 gag atc cgg tta aac atg cgt aca aaa gaa tcg aac cgt aag gtt atc      1344
```

```
Glu Ile Arg Leu Asn Met Arg Thr Lys Glu Ser Asn Arg Lys Val Ile
        435                 440                 445 gta acc gga gtg aat tta gaa gcg ggt cac ata aac cgt agt tac gtg    1392
Val Thr Gly Val Asn Leu Glu Ala Gly His Ile Asn Arg Ser Tyr Val
450                 455                 460 ggc cgg aaa agc cag ttc gtt tac ata gcc ata gcc gat cct tgg ccc    1440
Gly Arg Lys Ser Gln Phe Val Tyr Ile Ala Ile Ala Asp Pro Trp Pro
465                 470                 475                 480 aaa tgc agt ggc att gcg aag gta gat ata caa aac ggc acc gtt tca    1488
Lys Cys Ser Gly Ile Ala Lys Val Asp Ile Gln Asn Gly Thr Val Ser
                485                 490                 495 gag ttt aat tac gga ccg agc cgg ttc ggt gga gaa ccg tgc ttt gta    1536
Glu Phe Asn Tyr Gly Pro Ser Arg Phe Gly Gly Glu Pro Cys Phe Val
            500                 505                 510 ccg gag gga gaa gga gaa gaa gac aaa ggt tat gta atg ggg ttt gtg    1584
Pro Glu Gly Glu Gly Glu Glu Asp Lys Gly Tyr Val Met Gly Phe Val
        515                 520                 525 aga gac gaa gag aaa gac gag tcg gag ttt gtg gtg gtc gac gcg acg    1632
Arg Asp Glu Glu Lys Asp Glu Ser Glu Phe Val Val Val Asp Ala Thr
530                 535                 540 gat atg aag caa gtc gcg gcg gtg cgc ttg ccg gag agg gta cct tat    1680
Asp Met Lys Gln Val Ala Ala Val Arg Leu Pro Glu Arg Val Pro Tyr
545                 550                 555                 560 ggt ttc cat gga acg ttc gtg agc gag aat cag ttg aag gaa caa gtt    1728
Gly Phe His Gly Thr Phe Val Ser Glu Asn Gln Leu Lys Glu Gln Val
                565                 570                 575 ttc tga                                                             1734
Phe

<210> SEQ ID NO 10
<211> LENGTH: 577
<212> TYPE: PRT
<213> ORGANISM: Arabidopsis thaliana

<400> SEQUENCE: 10

Met Gln His Ser Leu Arg Ser Asp Leu Leu Pro Thr Lys Thr Ser Pro
1               5                   10                  15

Arg Ser His Leu Leu Pro Gln Pro Lys Asn Ala Asn Ile Ser Arg Arg
            20                  25                  30

Ile Leu Ile Asn Pro Phe Lys Ile Pro Thr Leu Pro Asp Leu Thr Ser
        35                  40                  45

Pro Val Pro Ser Pro Val Lys Leu Lys Pro Thr Tyr Pro Asn Leu Asn
    50                  55                  60

Leu Leu Gln Lys Leu Ala Ala Thr Met Leu Asp Lys Ile Glu Ser Ser
65                  70                  75                  80

Ile Val Ile Pro Met Glu Gln Asn Arg Pro Leu Pro Lys Pro Thr Asp
                85                  90                  95

Pro Ala Val Gln Leu Ser Gly Asn Phe Ala Pro Val Asn Glu Cys Pro
            100                 105                 110

Val Gln Asn Gly Leu Glu Val Val Gly Gln Ile Pro Ser Cys Leu Lys
        115                 120                 125

Gly Val Tyr Ile Arg Asn Gly Ala Asn Pro Met Phe Pro Pro Leu Ala
    130                 135                 140

Gly His His Leu Phe Asp Gly Asp Gly Met Ile His Ala Val Ser Ile
145                 150                 155                 160

Gly Phe Asp Asn Gln Val Ser Tyr Ser Cys Arg Tyr Thr Lys Thr Asn
                165                 170                 175
```

```
Arg Leu Val Gln Glu Thr Ala Leu Gly Arg Ser Val Phe Pro Lys Pro
            180                 185                 190

Ile Gly Glu Leu His Gly His Ser Gly Leu Ala Arg Leu Ala Leu Phe
        195                 200                 205

Thr Ala Arg Ala Gly Ile Gly Leu Val Asp Gly Thr Arg Gly Met Gly
    210                 215                 220

Val Ala Asn Ala Gly Val Val Phe Phe Asn Gly Arg Leu Leu Ala Met
225                 230                 235                 240

Ser Glu Asp Asp Leu Pro Tyr Gln Val Lys Ile Asp Gly Gln Gly Asp
                245                 250                 255

Leu Glu Thr Ile Gly Arg Phe Gly Phe Asp Asp Gln Ile Asp Ser Ser
            260                 265                 270

Val Ile Ala His Pro Lys Val Asp Ala Thr Thr Gly Asp Leu His Thr
        275                 280                 285

Leu Ser Tyr Asn Val Leu Lys Lys Pro His Leu Arg Tyr Leu Lys Phe
    290                 295                 300

Asn Thr Cys Gly Lys Lys Thr Arg Asp Val Glu Ile Thr Leu Pro Glu
305                 310                 315                 320

Pro Thr Met Ile His Asp Phe Ala Ile Thr Glu Asn Phe Val Val Ile
                325                 330                 335

Pro Asp Gln Gln Met Val Phe Lys Leu Ser Glu Met Ile Arg Gly Gly
            340                 345                 350

Ser Pro Val Ile Tyr Val Lys Glu Lys Met Ala Arg Phe Gly Val Leu
        355                 360                 365

Ser Lys Gln Asp Leu Thr Gly Ser Asp Ile Asn Trp Val Asp Val Pro
    370                 375                 380

Asp Cys Phe Cys Phe His Leu Trp Asn Ala Trp Glu Glu Arg Thr Glu
385                 390                 395                 400

Glu Gly Asp Pro Val Ile Val Ile Gly Ser Cys Met Ser Pro Pro
                405                 410                 415

Asp Thr Ile Phe Ser Glu Ser Gly Glu Pro Thr Arg Val Glu Leu Ser
            420                 425                 430

Glu Ile Arg Leu Asn Met Arg Thr Lys Glu Ser Asn Arg Lys Val Ile
        435                 440                 445

Val Thr Gly Val Asn Leu Glu Ala Gly His Ile Asn Arg Ser Tyr Val
    450                 455                 460

Gly Arg Lys Ser Gln Phe Val Tyr Ile Ala Ile Ala Asp Pro Trp Pro
465                 470                 475                 480

Lys Cys Ser Gly Ile Ala Lys Val Asp Ile Gln Asn Gly Thr Val Ser
                485                 490                 495

Glu Phe Asn Tyr Gly Pro Ser Arg Phe Gly Gly Glu Pro Cys Phe Val
            500                 505                 510

Pro Glu Gly Glu Gly Glu Glu Asp Lys Gly Tyr Val Met Gly Phe Val
        515                 520                 525

Arg Asp Glu Glu Lys Asp Glu Ser Glu Phe Val Val Asp Ala Thr
    530                 535                 540

Asp Met Lys Gln Val Ala Ala Val Arg Leu Pro Glu Arg Val Pro Tyr
545                 550                 555                 560

Gly Phe His Gly Thr Phe Val Ser Glu Asn Gln Leu Lys Glu Gln Val
                565                 570                 575

Phe

<210> SEQ ID NO 11
```

```
<211> LENGTH: 1839
<212> TYPE: DNA
<213> ORGANISM: Vigna unguiculata
<220> FEATURE:
<221> NAME/KEY: CDS
<222> LOCATION: (1)..(1836)

<400> SEQUENCE: 11 atg cct tca tca gct tca aac act tgg ttt aac gcc aca ctc cca tct        48
Met Pro Ser Ser Ala Ser Asn Thr Trp Phe Asn Ala Thr Leu Pro Ser
 1               5                  10                  15 ccc ccc ttc aaa gac cta cct tcc aca tct tct ccc aca aac tta ctt        96
Pro Pro Phe Lys Asp Leu Pro Ser Thr Ser Ser Pro Thr Asn Leu Leu
            20                  25                  30 cct tta agg aaa aca tcc tct tcc aac acc atc aca tgt tcc ctt caa       144
Pro Leu Arg Lys Thr Ser Ser Ser Asn Thr Ile Thr Cys Ser Leu Gln
        35                  40                  45 aca ctc cac ttc ccc aaa cag tac caa cca aca tcc aca tcc aca tcc       192
Thr Leu His Phe Pro Lys Gln Tyr Gln Pro Thr Ser Thr Ser Thr Ser
    50                  55                  60 aca gcc acc acc aca aca ccc acc cca atc aaa act acc acc atc acc       240
Thr Ala Thr Thr Thr Thr Pro Thr Pro Ile Lys Thr Thr Thr Ile Thr
65                  70                  75                  80 acc acc aca ccg ccc agg gaa acc aac cct ctc tct gac acc aac caa       288
Thr Thr Thr Pro Pro Arg Glu Thr Asn Pro Leu Ser Asp Thr Asn Gln
                85                  90                  95 cca tta cct caa aaa tgg aac ttt ctc cag aaa gcc gct gcc acg gcc       336
Pro Leu Pro Gln Lys Trp Asn Phe Leu Gln Lys Ala Ala Ala Thr Ala
            100                 105                 110 ttg gac ctg gtc gaa acg gcg ctc gtc tcg cac gag cgc aaa cac ccg       384
Leu Asp Leu Val Glu Thr Ala Leu Val Ser His Glu Arg Lys His Pro
        115                 120                 125 ctc ccc aaa acg gcg gac ccg agg gtc caa atc gcc ggg aac ttc gcg       432
Leu Pro Lys Thr Ala Asp Pro Arg Val Gln Ile Ala Gly Asn Phe Ala
    130                 135                 140 ccg gtg ccg gag cat gcc gcg gat caa gga ctc ccg gtg gtc gga aaa       480
Pro Val Pro Glu His Ala Ala Asp Gln Gly Leu Pro Val Val Gly Lys
145                 150                 155                 160 atc ccc aaa tgc att gac ggc gtg tac gtg cgc aac ggt gcc aat ccg       528
Ile Pro Lys Cys Ile Asp Gly Val Tyr Val Arg Asn Gly Ala Asn Pro
                165                 170                 175 ctc tac gag cct gtg gcc ggg cac cac ttc ttc gac ggc gac ggc atg       576
Leu Tyr Glu Pro Val Ala Gly His His Phe Phe Asp Gly Asp Gly Met
            180                 185                 190 gtc cac gcc gtg aag ttc acg aac ggc gcc gcc agc tac gcc tgc cgc       624
Val His Ala Val Lys Phe Thr Asn Gly Ala Ala Ser Tyr Ala Cys Arg
        195                 200                 205 ttc acc gag acg cag cgt ctc tcg cag gag aaa tct cta ggc cgc ccg       672
Phe Thr Glu Thr Gln Arg Leu Ser Gln Glu Lys Ser Leu Gly Arg Pro
    210                 215                 220 gtg ttc ccg aag gcc atc ggg gag ctc cac ggc cac tcc ggc atc gcg       720
Val Phe Pro Lys Ala Ile Gly Glu Leu His Gly His Ser Gly Ile Ala
225                 230                 235                 240 cgg ctc ctc ctc ttc tac gcg cgc ggt ctc ttc ggg ctc gtt gat ggg       768
Arg Leu Leu Leu Phe Tyr Ala Arg Gly Leu Phe Gly Leu Val Asp Gly
                245                 250                 255 tcc cag ggc atg ggc gtg gcg aac gcc ggt ctc gtc tac ttc aac aac       816
Ser Gln Gly Met Gly Val Ala Asn Ala Gly Leu Val Tyr Phe Asn Asn
            260                 265                 270 cac ctc ttg gcc atg tcc gaa gac gat tta ccc tac cac gtg aga atc       864
His Leu Leu Ala Met Ser Glu Asp Asp Leu Pro Tyr His Val Arg Ile
```

```
                       275                 280                 285
acc cct aac ggc gac tta acc acc gtt ggc cgt tac gac ttc aac ggg       912
Thr Pro Asn Gly Asp Leu Thr Thr Val Gly Arg Tyr Asp Phe Asn Gly
    290                 295                 300 cag ctc aac tca aca atg atc gcc cac ccg aaa ctg gac ccc gtc gac       960
Gln Leu Asn Ser Thr Met Ile Ala His Pro Lys Leu Asp Pro Val Asp
305                 310                 315                 320 ggc gac ctc cac gcg ctc agc tac gac gtc att cag aag cct tac ctc      1008
Gly Asp Leu His Ala Leu Ser Tyr Asp Val Ile Gln Lys Pro Tyr Leu
                325                 330                 335 aag tac ttc cgt ttc tcc ccc gac ggc gtc aag tcc ccc gac gtg gaa      1056
Lys Tyr Phe Arg Phe Ser Pro Asp Gly Val Lys Ser Pro Asp Val Glu
            340                 345                 350 atc ccc ctg aag gag ccc acc atg atg cac gat ttc gcc ata acg gag      1104
Ile Pro Leu Lys Glu Pro Thr Met Met His Asp Phe Ala Ile Thr Glu
        355                 360                 365 aat ttc gtc gtc gtc ccc gac cag cag gtg gtc ttc aaa cta acg gag      1152
Asn Phe Val Val Val Pro Asp Gln Gln Val Val Phe Lys Leu Thr Glu
    370                 375                 380 atg atc acc ggc ggg tcc ccc gtg gtc tac gac aag aac aaa acc tca      1200
Met Ile Thr Gly Gly Ser Pro Val Val Tyr Asp Lys Asn Lys Thr Ser
385                 390                 395                 400 cgg ttt ggg att ctg cac aag aat gcg aag gac gcg aat gcg atg cgg      1248
Arg Phe Gly Ile Leu His Lys Asn Ala Lys Asp Ala Asn Ala Met Arg
                405                 410                 415 tgg atc gac gcg ccg gat tgt ttc tgc ttc cac ctc tgg aac gcg tgg      1296
Trp Ile Asp Ala Pro Asp Cys Phe Cys Phe His Leu Trp Asn Ala Trp
            420                 425                 430 gag gag ccc gaa acc gag gag gtt gtg gtg att ggg tcc tgc atg acc      1344
Glu Glu Pro Glu Thr Glu Glu Val Val Val Ile Gly Ser Cys Met Thr
        435                 440                 445 cct gcg gac tcc att ttc aac gaa tgc gag gag agt ttg aag agc gtg      1392
Pro Ala Asp Ser Ile Phe Asn Glu Cys Glu Glu Ser Leu Lys Ser Val
    450                 455                 460 ctg tca gag ata agg ctg aac ttg agg acc ggc aag tcc act cgg cgc      1440
Leu Ser Glu Ile Arg Leu Asn Leu Arg Thr Gly Lys Ser Thr Arg Arg
465                 470                 475                 480 ccc att atc tcc gac gcc gaa caa gtg aac ctg gaa gcc ggc atg gtg      1488
Pro Ile Ile Ser Asp Ala Glu Gln Val Asn Leu Glu Ala Gly Met Val
                485                 490                 495 aac aga aac aag ctc gga agg aag acc cag ttc gcg tat ctg gct ctg      1536
Asn Arg Asn Lys Leu Gly Arg Lys Thr Gln Phe Ala Tyr Leu Ala Leu
            500                 505                 510 gcg gag ccc tgg ccc aaa gtc tcg ggc ttt gcg aaa gtt gat ttg ctg      1584
Ala Glu Pro Trp Pro Lys Val Ser Gly Phe Ala Lys Val Asp Leu Leu
        515                 520                 525 agt ggg gaa gtg aag aag tac atg tat gga gaa gag aag ttc ggt ggg      1632
Ser Gly Glu Val Lys Lys Tyr Met Tyr Gly Glu Glu Lys Phe Gly Gly
    530                 535                 540 gag cct ctg ttt ctt ccc aac ggc caa aaa gaa gac gat ggg tat att      1680
Glu Pro Leu Phe Leu Pro Asn Gly Gln Lys Glu Asp Asp Gly Tyr Ile
545                 550                 555                 560 ctg gca ttc gtg cac gac gag aaa gaa tgg aaa tcc gag ctg cag att      1728
Leu Ala Phe Val His Asp Glu Lys Glu Trp Lys Ser Glu Leu Gln Ile
                565                 570                 575 gtg aat gcc caa aat tta aag ctc gaa gct tcc atc aaa ctc ccc tct      1776
Val Asn Ala Gln Asn Leu Lys Leu Glu Ala Ser Ile Lys Leu Pro Ser
            580                 585                 590 cgt gtt ccc tac ggt ttt cat gga act ttc att cat tcc aag gat ttg      1824
```

```
Arg Val Pro Tyr Gly Phe His Gly Thr Phe Ile His Ser Lys Asp Leu
        595                 600                 605 agg aaa caa gct tga                                                    1839
Arg Lys Gln Ala
    610

<210> SEQ ID NO 12
<211> LENGTH: 612
<212> TYPE: PRT
<213> ORGANISM: Vigna unguiculata

<400> SEQUENCE: 12

Met Pro Ser Ser Ala Ser Asn Thr Trp Phe Asn Ala Thr Leu Pro Ser
  1               5                  10                  15

Pro Pro Phe Lys Asp Leu Pro Ser Thr Ser Ser Pro Thr Asn Leu Leu
             20                  25                  30

Pro Leu Arg Lys Thr Ser Ser Asn Thr Ile Thr Cys Ser Leu Gln
         35                  40                  45

Thr Leu His Phe Pro Lys Gln Tyr Gln Pro Thr Ser Thr Ser Thr Ser
     50                  55                  60

Thr Ala Thr Thr Thr Pro Thr Pro Ile Lys Thr Thr Thr Ile Thr
 65                  70                  75                  80

Thr Thr Thr Pro Pro Arg Glu Thr Asn Pro Leu Ser Asp Thr Asn Gln
                 85                  90                  95

Pro Leu Pro Gln Lys Trp Asn Phe Leu Gln Lys Ala Ala Ala Thr Ala
            100                 105                 110

Leu Asp Leu Val Glu Thr Ala Leu Val Ser His Glu Arg Lys His Pro
        115                 120                 125

Leu Pro Lys Thr Ala Asp Pro Arg Val Gln Ile Ala Gly Asn Phe Ala
    130                 135                 140

Pro Val Pro Glu His Ala Ala Asp Gln Gly Leu Pro Val Val Gly Lys
145                 150                 155                 160

Ile Pro Lys Cys Ile Asp Gly Val Tyr Val Arg Asn Gly Ala Asn Pro
                165                 170                 175

Leu Tyr Glu Pro Val Ala Gly His His Phe Phe Asp Gly Asp Gly Met
            180                 185                 190

Val His Ala Val Lys Phe Thr Asn Gly Ala Ala Ser Tyr Ala Cys Arg
        195                 200                 205

Phe Thr Glu Thr Gln Arg Leu Ser Gln Glu Lys Ser Leu Gly Arg Pro
    210                 215                 220

Val Phe Pro Lys Ala Ile Gly Glu Leu His Gly His Ser Gly Ile Ala
225                 230                 235                 240

Arg Leu Leu Leu Phe Tyr Ala Arg Gly Leu Phe Gly Leu Val Asp Gly
                245                 250                 255

Ser Gln Gly Met Gly Val Ala Asn Ala Gly Leu Val Tyr Phe Asn Asn
            260                 265                 270

His Leu Leu Ala Met Ser Glu Asp Asp Leu Pro Tyr His Val Arg Ile
        275                 280                 285

Thr Pro Asn Gly Asp Leu Thr Val Gly Arg Tyr Asp Phe Asn Gly
    290                 295                 300

Gln Leu Asn Ser Thr Met Ile Ala His Pro Lys Leu Asp Pro Val Asp
305                 310                 315                 320

Gly Asp Leu His Ala Leu Ser Tyr Asp Val Ile Gln Lys Pro Tyr Leu
                325                 330                 335

Lys Tyr Phe Arg Phe Ser Pro Asp Gly Val Lys Ser Pro Asp Val Glu
```

```
                    340                 345                 350
Ile Pro Leu Lys Glu Pro Thr Met Met His Asp Phe Ala Ile Thr Glu
            355                 360                 365

Asn Phe Val Val Pro Asp Gln Gln Val Val Phe Lys Leu Thr Glu
        370                 375                 380

Met Ile Thr Gly Gly Ser Pro Val Val Tyr Asp Lys Asn Lys Thr Ser
385                 390                 395                 400

Arg Phe Gly Ile Leu His Lys Asn Ala Lys Asp Ala Asn Ala Met Arg
                405                 410                 415

Trp Ile Asp Ala Pro Asp Cys Phe Cys Phe His Leu Trp Asn Ala Trp
            420                 425                 430

Glu Glu Pro Glu Thr Glu Val Val Val Ile Gly Ser Cys Met Thr
        435                 440                 445

Pro Ala Asp Ser Ile Phe Asn Glu Cys Glu Glu Ser Leu Lys Ser Val
    450                 455                 460

Leu Ser Glu Ile Arg Leu Asn Leu Arg Thr Gly Lys Ser Thr Arg Arg
465                 470                 475                 480

Pro Ile Ile Ser Asp Ala Glu Gln Val Asn Leu Glu Ala Gly Met Val
                485                 490                 495

Asn Arg Asn Lys Leu Gly Arg Lys Thr Gln Phe Ala Tyr Leu Ala Leu
            500                 505                 510

Ala Glu Pro Trp Pro Lys Val Ser Gly Phe Ala Lys Val Asp Leu Leu
        515                 520                 525

Ser Gly Glu Val Lys Lys Tyr Met Tyr Gly Glu Lys Phe Gly Gly
    530                 535                 540

Glu Pro Leu Phe Leu Pro Asn Gly Gln Lys Glu Asp Asp Gly Tyr Ile
545                 550                 555                 560

Leu Ala Phe Val His Asp Glu Lys Glu Trp Lys Ser Glu Leu Gln Ile
                565                 570                 575

Val Asn Ala Gln Asn Leu Lys Leu Glu Ala Ser Ile Lys Leu Pro Ser
            580                 585                 590

Arg Val Pro Tyr Gly Phe His Gly Thr Phe Ile His Ser Lys Asp Leu
        595                 600                 605

Arg Lys Gln Ala
    610

<210> SEQ ID NO 13
<211> LENGTH: 1815
<212> TYPE: DNA
<213> ORGANISM: Zea mays
<220> FEATURE:
<221> NAME/KEY: CDS
<222> LOCATION: (1)..(1812)

<400> SEQUENCE: 13 atg cag ggt ctc gcc ccg ccc acc tct gtt tcc ata cac cgg cac ctg     48
Met Gln Gly Leu Ala Pro Pro Thr Ser Val Ser Ile His Arg His Leu
  1               5                  10                  15 ccg gcc cgg tcc agg gcc cgg gcc tcc aat tcc gtc agg ttc tcg ccg     96
Pro Ala Arg Ser Arg Ala Arg Ala Ser Asn Ser Val Arg Phe Ser Pro
             20                  25                  30 cgc gcc gtc agc tcc gtg ccg ccc gcc gag tgc ctc cag gcg ccg ttc    144
Arg Ala Val Ser Ser Val Pro Pro Ala Glu Cys Leu Gln Ala Pro Phe
         35                  40                  45 cac aag ccc gtc gcc gac ctg cct gcg ccg tcc agg aag ccc gcc gcc    192
His Lys Pro Val Ala Asp Leu Pro Ala Pro Ser Arg Lys Pro Ala Ala
     50                  55                  60
```

-continued

| | |
|---|---|
| att gcc gtc cca ggg cac gcc gcg gcg ccg agg aaa gcg gag ggc ggc<br>Ile Ala Val Pro Gly His Ala Ala Ala Pro Arg Lys Ala Glu Gly Gly<br>65                           70                          75                        80 | 240 |
| aag aag cag ctc aac ttg ttc cag cgc gcc gcg gcc gcg ctc gac<br>Lys Lys Gln Leu Asn Leu Phe Gln Arg Ala Ala Ala Ala Leu Asp<br>                       85                         90                        95 | 288 |
| gcg ttc gag gaa ggg ttc gtg gcc aac gtc ctc gag cgg ccc cac ggg<br>Ala Phe Glu Glu Gly Phe Val Ala Asn Val Leu Glu Arg Pro His Gly<br>                 100                       105                    110 | 336 |
| ctg ccc agc acg gcc gac ccg gcc gtg cag atc gcc ggc aac ttc gcg<br>Leu Pro Ser Thr Ala Asp Pro Ala Val Gln Ile Ala Gly Asn Phe Ala<br>         115                       120                       125 | 384 |
| ccc gtc ggg gag agg ccg ccc gtg cac gag ctc ccc gtc tcc ggc cgc<br>Pro Val Gly Glu Arg Pro Pro Val His Glu Leu Pro Val Ser Gly Arg<br>130                          135                       140 | 432 |
| atc ccg ccc ttc atc gac ggg gtc tac gcg cgc aac ggc gcc aac ccc<br>Ile Pro Pro Phe Ile Asp Gly Val Tyr Ala Arg Asn Gly Ala Asn Pro<br>145                       150                       155                160 | 480 |
| tgc ttc gac ccc gtc gcg ggg cac cac ctc ttc gac ggc gac ggc atg<br>Cys Phe Asp Pro Val Ala Gly His His Leu Phe Asp Gly Asp Gly Met<br>                 165                      170                    175 | 528 |
| gtg cac gcg ctg cgg ata cgc aac ggc gcc gcc gag tcc tac gcc tgc<br>Val His Ala Leu Arg Ile Arg Asn Gly Ala Ala Glu Ser Tyr Ala Cys<br>         180                       185                       190 | 576 |
| cgc ttc acg gag acc gcg cgc ctg cgc cag gag cgc gcg atc ggc cgc<br>Arg Phe Thr Glu Thr Ala Arg Leu Arg Gln Glu Arg Ala Ile Gly Arg<br>                       195                       200                    205 | 624 |
| ccc gtc ttc ccc aag gcc att ggc gag ctg cac ggg cac tcc ggg atc<br>Pro Val Phe Pro Lys Ala Ile Gly Glu Leu His Gly His Ser Gly Ile<br>210                          215                       220 | 672 |
| gcg cgc ctc gcc ctg ttc tac gcg cgc gcc gcg tgc ggc ctc gtg gac<br>Ala Arg Leu Ala Leu Phe Tyr Ala Arg Ala Ala Cys Gly Leu Val Asp<br>225                          230                       235                240 | 720 |
| ccc tcg gcc ggc acc ggc gtg gcc aac gcc ggc ctc gtc tac ttc aac<br>Pro Ser Ala Gly Thr Gly Val Ala Asn Ala Gly Leu Val Tyr Phe Asn<br>                       245                       250                    255 | 768 |
| ggc cgc ctg ctc gcc atg tcc gag gac gac ctc ccc tac cac gtc cgc<br>Gly Arg Leu Leu Ala Met Ser Glu Asp Asp Leu Pro Tyr His Val Arg<br>                 260                       265                    270 | 816 |
| gtg gcg gac gac ggc gac ctc gag acc gtc ggc cgc tac gac ttc gac<br>Val Ala Asp Asp Gly Asp Leu Glu Thr Val Gly Arg Tyr Asp Phe Asp<br>         275                       280                       285 | 864 |
| ggg cag ctc ggc tgc gcc atg atc gcg cac ccc aag ctg gac ccg gcc<br>Gly Gln Leu Gly Cys Ala Met Ile Ala His Pro Lys Leu Asp Pro Ala<br>290                          295                       300 | 912 |
| acc ggg gag ctc cac gcg ctc agc tac gac gtc atc aag agg ccg tac<br>Thr Gly Glu Leu His Ala Leu Ser Tyr Asp Val Ile Lys Arg Pro Tyr<br>305                          310                       315                320 | 960 |
| ctc aag tac ttc tac ttc agg ccc gac ggc acc aag tcc gac gac gtg<br>Leu Lys Tyr Phe Tyr Phe Arg Pro Asp Gly Thr Lys Ser Asp Asp Val<br>                       325                       330                    335 | 1008 |
| gag atc ccg ctg gag cag ccc acg atg atc cac gac ttc gcc atc acc<br>Glu Ile Pro Leu Glu Gln Pro Thr Met Ile His Asp Phe Ala Ile Thr<br>         340                       345                       350 | 1056 |
| gag aac ttc gtg gtt gtg ccc gac cac cag gtg gtg ttc aag ctc cag<br>Glu Asn Phe Val Val Val Pro Asp His Gln Val Val Phe Lys Leu Gln<br>                 355                       360                    365 | 1104 |
| gag atg ctg cgc ggc ggg tcg ccc gtg gtg ctg gac aag gag aag acg<br>Glu Met Leu Arg Gly Gly Ser Pro Val Val Leu Asp Lys Glu Lys Thr | 1152 |

```
                370                 375                 380
tcg cgg ttc ggc gtg ctc ccc aag cac gcc gcg gac gcg tcg gag atg      1200
Ser Arg Phe Gly Val Leu Pro Lys His Ala Ala Asp Ala Ser Glu Met
385                 390                 395                 400 gcg tgg gtg gac gtg ccg gac tgc ttc tgc ttc cac ctg tgg aac gcg      1248
Ala Trp Val Asp Val Pro Asp Cys Phe Cys Phe His Leu Trp Asn Ala
                405                 410                 415 tgg gag gac gag gcg acg ggc gag gtg gtg gtg atc ggc tcc tgc atg      1296
Trp Glu Asp Glu Ala Thr Gly Glu Val Val Val Ile Gly Ser Cys Met
            420                 425                 430 acc ccc gcc gac tcc atc ttc aac gag tcc gac gag cgc ctg gag agc      1344
Thr Pro Ala Asp Ser Ile Phe Asn Glu Ser Asp Glu Arg Leu Glu Ser
        435                 440                 445 gtg ctg acc gag atc cgc ctg gac gcg cgc acg ggc cgg tcc acg cgc      1392
Val Leu Thr Glu Ile Arg Leu Asp Ala Arg Thr Gly Arg Ser Thr Arg
    450                 455                 460 cgc gcc gtc ctg ccg ccg tcg cag cag gag aac ctg gag gtg ggc atg      1440
Arg Ala Val Leu Pro Pro Ser Gln Gln Glu Asn Leu Glu Val Gly Met
465                 470                 475                 480 gtg aac cgc aac ctg ctg ggc cgc gag agc cgg tac gcg tac ctc gcg      1488
Val Asn Arg Asn Leu Leu Gly Arg Glu Ser Arg Tyr Ala Tyr Leu Ala
                485                 490                 495 gtg gcg gag ccg tgg ccc aag gag tcg ggc ttc gcc aag gag gac ctg      1536
Val Ala Glu Pro Trp Pro Lys Glu Ser Gly Phe Ala Lys Glu Asp Leu
            500                 505                 510 tcc acg ggc gag ctc acc aag ttc gag tac ggc gag ggc cgg ttc ggc      1584
Ser Thr Gly Glu Leu Thr Lys Phe Glu Tyr Gly Glu Gly Arg Phe Gly
        515                 520                 525 ggc gag ccc tgc ttc gtt ccc atg gac ccg gcc gcg gcc cac ccg cgc      1632
Gly Glu Pro Cys Phe Val Pro Met Asp Pro Ala Ala Ala His Pro Arg
    530                 535                 540 ggc gag gac gac ggg tac gtg ctc acc ttc gtc cac gac gag cgc gcc      1680
Gly Glu Asp Asp Gly Tyr Val Leu Thr Phe Val His Asp Glu Arg Ala
545                 550                 555                 560 ggc acg tcg gag cta ctt gtg gtc aat gcc gcc gac atc cgg ctg gag      1728
Gly Thr Ser Glu Leu Leu Val Val Asn Ala Ala Asp Ile Arg Leu Glu
                565                 570                 575 gcc acg gtt cag ctg ccg tcc cgc gtg ccc ttc ggc ttc cac ggc acc      1776
Ala Thr Val Gln Leu Pro Ser Arg Val Pro Phe Gly Phe His Gly Thr
            580                 585                 590 ttc atc acg ggc cag gag ctc gag gcc cag gcg gcc tga                  1815
Phe Ile Thr Gly Gln Glu Leu Glu Ala Gln Ala Ala
        595                 600

<210> SEQ ID NO 14
<211> LENGTH: 604
<212> TYPE: PRT
<213> ORGANISM: Zea mays

<400> SEQUENCE: 14

Met Gln Gly Leu Ala Pro Pro Thr Ser Val Ser Ile His Arg His Leu
 1               5                  10                  15

Pro Ala Arg Ser Arg Ala Arg Ala Ser Asn Ser Val Arg Phe Ser Pro
            20                  25                  30

Arg Ala Val Ser Ser Val Pro Pro Ala Glu Cys Leu Gln Ala Pro Phe
        35                  40                  45

His Lys Pro Val Ala Asp Leu Pro Ala Pro Ser Arg Lys Pro Ala Ala
    50                  55                  60

Ile Ala Val Pro Gly His Ala Ala Ala Pro Arg Lys Ala Glu Gly Gly
```

-continued

```
                65                  70                  75                  80
Lys Lys Gln Leu Asn Leu Phe Gln Arg Ala Ala Ala Ala Leu Asp
                    85                  90                  95
Ala Phe Glu Glu Gly Phe Val Ala Asn Val Leu Glu Arg Pro His Gly
                100                 105                 110
Leu Pro Ser Thr Ala Asp Pro Ala Val Gln Ile Ala Gly Asn Phe Ala
                115                 120                 125
Pro Val Gly Glu Arg Pro Val His Glu Leu Pro Val Ser Gly Arg
            130                 135                 140
Ile Pro Pro Phe Ile Asp Gly Val Tyr Ala Arg Asn Gly Ala Asn Pro
145                 150                 155                 160
Cys Phe Asp Pro Val Ala Gly His His Leu Phe Asp Gly Asp Gly Met
                165                 170                 175
Val His Ala Leu Arg Ile Arg Asn Gly Ala Ala Glu Ser Tyr Ala Cys
                180                 185                 190
Arg Phe Thr Glu Thr Ala Arg Leu Arg Gln Glu Arg Ala Ile Gly Arg
                195                 200                 205
Pro Val Phe Pro Lys Ala Ile Gly Glu Leu His Gly His Ser Gly Ile
            210                 215                 220
Ala Arg Leu Ala Leu Phe Tyr Ala Arg Ala Ala Cys Gly Leu Val Asp
225                 230                 235                 240
Pro Ser Ala Gly Thr Gly Val Ala Asn Ala Gly Leu Val Tyr Phe Asn
                245                 250                 255
Gly Arg Leu Leu Ala Met Ser Glu Asp Asp Leu Pro Tyr His Val Arg
            260                 265                 270
Val Ala Asp Asp Gly Asp Leu Glu Thr Val Gly Arg Tyr Asp Phe Asp
            275                 280                 285
Gly Gln Leu Gly Cys Ala Met Ile Ala His Pro Lys Leu Asp Pro Ala
            290                 295                 300
Thr Gly Glu Leu His Ala Leu Ser Tyr Asp Val Ile Lys Arg Pro Tyr
305                 310                 315                 320
Leu Lys Tyr Phe Tyr Phe Arg Pro Asp Gly Thr Lys Ser Asp Asp Val
                325                 330                 335
Glu Ile Pro Leu Glu Gln Pro Thr Met Ile His Asp Phe Ala Ile Thr
                340                 345                 350
Glu Asn Phe Val Val Pro Asp His Gln Val Val Phe Lys Leu Gln
                355                 360                 365
Glu Met Leu Arg Gly Gly Ser Pro Val Val Leu Asp Lys Glu Lys Thr
            370                 375                 380
Ser Arg Phe Gly Val Leu Pro Lys His Ala Ala Asp Ala Ser Glu Met
385                 390                 395                 400
Ala Trp Val Asp Val Pro Asp Cys Phe Cys Phe His Leu Trp Asn Ala
                405                 410                 415
Trp Glu Asp Glu Ala Thr Gly Glu Val Val Ile Gly Ser Cys Met
            420                 425                 430
Thr Pro Ala Asp Ser Ile Phe Asn Glu Ser Asp Glu Arg Leu Glu Ser
                435                 440                 445
Val Leu Thr Glu Ile Arg Leu Asp Ala Arg Thr Gly Arg Ser Thr Arg
            450                 455                 460
Arg Ala Val Leu Pro Pro Ser Gln Gln Glu Asn Leu Glu Val Gly Met
465                 470                 475                 480
Val Asn Arg Asn Leu Leu Gly Arg Glu Ser Arg Tyr Ala Tyr Leu Ala
                485                 490                 495
```

```
Val Ala Glu Pro Trp Pro Lys Glu Ser Gly Phe Ala Lys Glu Asp Leu
            500                 505                 510

Ser Thr Gly Glu Leu Thr Lys Phe Glu Tyr Gly Glu Gly Arg Phe Gly
            515                 520                 525

Gly Glu Pro Cys Phe Val Pro Met Asp Pro Ala Ala Ala His Pro Arg
            530                 535                 540

Gly Glu Asp Asp Gly Tyr Val Leu Thr Phe Val His Asp Glu Arg Ala
545                 550                 555                 560

Gly Thr Ser Glu Leu Leu Val Val Asn Ala Ala Asp Ile Arg Leu Glu
            565                 570                 575

Ala Thr Val Gln Leu Pro Ser Arg Val Pro Phe Gly Phe His Gly Thr
            580                 585                 590

Phe Ile Thr Gly Gln Glu Leu Glu Ala Gln Ala Ala
            595                 600

<210> SEQ ID NO 15
<211> LENGTH: 1818
<212> TYPE: DNA
<213> ORGANISM: Lycopersicon esculentum
<220> FEATURE:
<221> NAME/KEY: CDS
<222> LOCATION: (1)..(1815)

<400> SEQUENCE: 15 atg gca act act act tca cat gcc aca aat aca tgg att aag act aag        48
Met Ala Thr Thr Thr Ser His Ala Thr Asn Thr Trp Ile Lys Thr Lys
  1               5                  10                  15 ttg tca atg cca tca tca aag gag ttt ggt ttt gca tca aac tct att        96
Leu Ser Met Pro Ser Ser Lys Glu Phe Gly Phe Ala Ser Asn Ser Ile
                 20                  25                  30 tct cta ctc aaa aat caa cat aat agg caa agt ctc aac att aat tcc       144
Ser Leu Leu Lys Asn Gln His Asn Arg Gln Ser Leu Asn Ile Asn Ser
             35                  40                  45 tct ctt caa gct cca cct ata ctt cat ttt cct aaa caa tct tca aat       192
Ser Leu Gln Ala Pro Pro Ile Leu His Phe Pro Lys Gln Ser Ser Asn
         50                  55                  60 tat caa aca cca aag aat aat aca att tca cac cca aaa caa gaa aac       240
Tyr Gln Thr Pro Lys Asn Asn Thr Ile Ser His Pro Lys Gln Glu Asn
 65                  70                  75                  80 aac aac tcc tct tct tct tca act tcc aag tgg aat tta gtg cag aaa       288
Asn Asn Ser Ser Ser Ser Ser Thr Ser Lys Trp Asn Leu Val Gln Lys
                 85                  90                  95 gca gca gca atg gct tta gat gct gta gaa agt gct tta act aaa cat       336
Ala Ala Ala Met Ala Leu Asp Ala Val Glu Ser Ala Leu Thr Lys His
                100                 105                 110 gaa ctt gaa cac cct ttg ccg aaa aca gcc gac cca cga gtc cag att       384
Glu Leu Glu His Pro Leu Pro Lys Thr Ala Asp Pro Arg Val Gln Ile
            115                 120                 125 tct ggg aat ttt gct ccg gta ccg gaa aat cca gtc tgt caa tct ctt       432
Ser Gly Asn Phe Ala Pro Val Pro Glu Asn Pro Val Cys Gln Ser Leu
        130                 135                 140 ccg gtc acc gga aaa ata ccc aaa tgt gtt caa ggc gtt tac gtt cga       480
Pro Val Thr Gly Lys Ile Pro Lys Cys Val Gln Gly Val Tyr Val Arg
145                 150                 155                 160 aac gga gct aac cct ctt ttt gaa cca acc gcc gga cac cat ttc ttc       528
Asn Gly Ala Asn Pro Leu Phe Glu Pro Thr Ala Gly His His Phe Phe
                165                 170                 175 gac ggc gac ggt atg gtt cac gcc gtt caa ttc aaa aat ggg tcg gct       576
Asp Gly Asp Gly Met Val His Ala Val Gln Phe Lys Asn Gly Ser Ala
```

```
                     180                 185                 190
agt tac gct tgc cgt ttc act gaa aca gag agg ctt gtt caa gaa aaa         624
Ser Tyr Ala Cys Arg Phe Thr Glu Thr Glu Arg Leu Val Gln Glu Lys
        195                 200                 205 gct ttg ggt cgc cct gtt ttc cct aaa gcc att ggt gaa tta cat ggt         672
Ala Leu Gly Arg Pro Val Phe Pro Lys Ala Ile Gly Glu Leu His Gly
210                 215                 220 cac tct gga att gca agg ctt atg ctg ttt tac gct cgt ggg ctc ttc         720
His Ser Gly Ile Ala Arg Leu Met Leu Phe Tyr Ala Arg Gly Leu Phe
225                 230                 235                 240 gga ctt gtt gat cac agt aaa gga act ggt gtt gca aac gcc ggt tta         768
Gly Leu Val Asp His Ser Lys Gly Thr Gly Val Ala Asn Ala Gly Leu
            245                 250                 255 gtc tat ttc aat aac cga tta ctt gct atg tct gaa gat gat ttg cct         816
Val Tyr Phe Asn Asn Arg Leu Leu Ala Met Ser Glu Asp Asp Leu Pro
                260                 265                 270 tac cat gta aag gta aca ccc acc ggc gat ctt aaa aca gag ggt cga         864
Tyr His Val Lys Val Thr Pro Thr Gly Asp Leu Lys Thr Glu Gly Arg
            275                 280                 285 ttc gat ttc gac ggc cag cta aaa tcc acc atg ata gct cac cca aag         912
Phe Asp Phe Asp Gly Gln Leu Lys Ser Thr Met Ile Ala His Pro Lys
290                 295                 300 ctc gac cca gtt tcc ggt gag cta ttt gct ctt agc tac gat gtg att         960
Leu Asp Pro Val Ser Gly Glu Leu Phe Ala Leu Ser Tyr Asp Val Ile
305                 310                 315                 320 cag aag cca tac ctc aag tac ttc aga ttt tca aaa aat ggg gaa aaa        1008
Gln Lys Pro Tyr Leu Lys Tyr Phe Arg Phe Ser Lys Asn Gly Glu Lys
            325                 330                 335 tca aat gat gtt gaa att cca gtt gaa gac cca aca atg atg cat gat        1056
Ser Asn Asp Val Glu Ile Pro Val Glu Asp Pro Thr Met Met His Asp
                340                 345                 350 ttc gca att act gag aac ttc gtc gtc att cct gat caa caa gtc gtt        1104
Phe Ala Ile Thr Glu Asn Phe Val Val Ile Pro Asp Gln Gln Val Val
            355                 360                 365 ttc aag atg tct gaa atg atc cgt gga ggt tca ccg gtg gtt tac gac        1152
Phe Lys Met Ser Glu Met Ile Arg Gly Gly Ser Pro Val Val Tyr Asp
370                 375                 380 aag aac aaa gtt tcc cga ttt ggt att ctg gat aag tac gcg aaa gat        1200
Lys Asn Lys Val Ser Arg Phe Gly Ile Leu Asp Lys Tyr Ala Lys Asp
385                 390                 395                 400 ggg tct gat ttg aaa tgg gtt gaa gta cct gat tgt ttc tgt ttc cac        1248
Gly Ser Asp Leu Lys Trp Val Glu Val Pro Asp Cys Phe Cys Phe His
            405                 410                 415 ctc tgg aat gct tgg gaa gaa gca gaa aca gat gaa atc gtt gta att        1296
Leu Trp Asn Ala Trp Glu Glu Ala Glu Thr Asp Glu Ile Val Val Ile
                420                 425                 430 ggt tca tgt atg aca cca cca gac tcc att ttc aat gaa tgt gat gaa        1344
Gly Ser Cys Met Thr Pro Pro Asp Ser Ile Phe Asn Glu Cys Asp Glu
            435                 440                 445 ggg cta aag agt gtt tta tcc gaa atc cgt ctc aat ttg aaa aca ggg        1392
Gly Leu Lys Ser Val Leu Ser Glu Ile Arg Leu Asn Leu Lys Thr Gly
450                 455                 460 aaa tca aca aga aaa tcc ata atc gaa aac ccg gat gaa caa gtg aat        1440
Lys Ser Thr Arg Lys Ser Ile Ile Glu Asn Pro Asp Glu Gln Val Asn
465                 470                 475                 480 tta gaa gct gga atg gtg aac cga aac aaa ctc gga agg aaa aca gag        1488
Leu Glu Ala Gly Met Val Asn Arg Asn Lys Leu Gly Arg Lys Thr Glu
            485                 490                 495 tat gct tat ttg gct atc gct gaa cca tgg cca aaa gtt tct ggt ttt        1536
```

```
Tyr Ala Tyr Leu Ala Ile Ala Glu Pro Trp Pro Lys Val Ser Gly Phe
            500                 505                 510 gca aaa gta aac ctg ttc acc ggt gaa gtt gag aaa ttc att tat ggt      1584
Ala Lys Val Asn Leu Phe Thr Gly Glu Val Glu Lys Phe Ile Tyr Gly
        515                 520                 525 gac aac aaa tat ggt ggg gaa cct ctt ttt tta cca aga gac ccc aac      1632
Asp Asn Lys Tyr Gly Gly Glu Pro Leu Phe Leu Pro Arg Asp Pro Asn
    530                 535                 540 agc aag gaa gaa gac gat ggt tat att tta gct ttc gtt cac gat gag      1680
Ser Lys Glu Glu Asp Asp Gly Tyr Ile Leu Ala Phe Val His Asp Glu
545                 550                 555                 560 aaa gaa tgg aaa tca gaa ctg caa att gtt aac gca atg agt ttg aag      1728
Lys Glu Trp Lys Ser Glu Leu Gln Ile Val Asn Ala Met Ser Leu Lys
                565                 570                 575 ttg gag gca act gtg aag ctt cca tca aga gtt cct tat gga ttt cat      1776
Leu Glu Ala Thr Val Lys Leu Pro Ser Arg Val Pro Tyr Gly Phe His
            580                 585                 590 gga aca ttc ata aac gcc aat gat ttg gca aat cag gca tga              1818
Gly Thr Phe Ile Asn Ala Asn Asp Leu Ala Asn Gln Ala
        595                 600                 605

<210> SEQ ID NO 16
<211> LENGTH: 605
<212> TYPE: PRT
<213> ORGANISM: Lycopersicon esculentum

<400> SEQUENCE: 16

Met Ala Thr Thr Thr Ser His Ala Thr Asn Thr Trp Ile Lys Thr Lys
1               5                   10                  15

Leu Ser Met Pro Ser Ser Lys Glu Phe Gly Phe Ala Ser Asn Ser Ile
            20                  25                  30

Ser Leu Leu Lys Asn Gln His Asn Arg Gln Ser Leu Asn Ile Asn Ser
        35                  40                  45

Ser Leu Gln Ala Pro Pro Ile Leu His Phe Pro Lys Gln Ser Ser Asn
    50                  55                  60

Tyr Gln Thr Pro Lys Asn Asn Thr Ile Ser His Pro Lys Gln Glu Asn
65                  70                  75                  80

Asn Asn Ser Ser Ser Ser Thr Ser Lys Trp Asn Leu Val Gln Lys
                85                  90                  95

Ala Ala Ala Met Ala Leu Asp Ala Val Glu Ser Ala Leu Thr Lys His
            100                 105                 110

Glu Leu Glu His Pro Leu Pro Lys Thr Ala Asp Pro Arg Val Gln Ile
        115                 120                 125

Ser Gly Asn Phe Ala Pro Val Pro Glu Asn Pro Val Cys Gln Ser Leu
    130                 135                 140

Pro Val Thr Gly Lys Ile Pro Lys Cys Val Gln Gly Val Tyr Val Arg
145                 150                 155                 160

Asn Gly Ala Asn Pro Leu Phe Glu Pro Thr Ala Gly His His Phe
                165                 170                 175

Asp Gly Asp Gly Met Val His Ala Val Gln Phe Lys Asn Gly Ser Ala
            180                 185                 190

Ser Tyr Ala Cys Arg Phe Thr Glu Thr Glu Arg Leu Val Gln Glu Lys
        195                 200                 205

Ala Leu Gly Arg Pro Val Phe Pro Lys Ala Ile Gly Glu Leu His Gly
    210                 215                 220

His Ser Gly Ile Ala Arg Leu Met Leu Phe Tyr Ala Arg Gly Leu Phe
225                 230                 235                 240
```

Gly Leu Val Asp His Ser Lys Gly Thr Gly Val Ala Asn Ala Gly Leu
            245                 250                 255

Val Tyr Phe Asn Asn Arg Leu Leu Ala Met Ser Glu Asp Asp Leu Pro
        260                 265                 270

Tyr His Val Lys Val Thr Pro Thr Gly Asp Leu Lys Thr Glu Gly Arg
    275                 280                 285

Phe Asp Phe Asp Gly Gln Leu Lys Ser Thr Met Ile Ala His Pro Lys
290                 295                 300

Leu Asp Pro Val Ser Gly Glu Leu Phe Ala Leu Ser Tyr Asp Val Ile
305                 310                 315                 320

Gln Lys Pro Tyr Leu Lys Tyr Phe Arg Phe Ser Lys Asn Gly Glu Lys
                325                 330                 335

Ser Asn Asp Val Glu Ile Pro Val Glu Asp Pro Thr Met Met His Asp
            340                 345                 350

Phe Ala Ile Thr Glu Asn Phe Val Val Ile Pro Asp Gln Gln Val Val
        355                 360                 365

Phe Lys Met Ser Glu Met Ile Arg Gly Gly Ser Pro Val Val Tyr Asp
    370                 375                 380

Lys Asn Lys Val Ser Arg Phe Gly Ile Leu Asp Lys Tyr Ala Lys Asp
385                 390                 395                 400

Gly Ser Asp Leu Lys Trp Val Glu Val Pro Asp Cys Phe Cys Phe His
                405                 410                 415

Leu Trp Asn Ala Trp Glu Glu Ala Glu Thr Asp Glu Ile Val Val Ile
            420                 425                 430

Gly Ser Cys Met Thr Pro Pro Asp Ser Ile Phe Asn Glu Cys Asp Glu
        435                 440                 445

Gly Leu Lys Ser Val Leu Ser Glu Ile Arg Leu Asn Leu Lys Thr Gly
    450                 455                 460

Lys Ser Thr Arg Lys Ser Ile Ile Glu Asn Pro Asp Glu Gln Val Asn
465                 470                 475                 480

Leu Glu Ala Gly Met Val Asn Arg Asn Lys Leu Gly Arg Lys Thr Glu
                485                 490                 495

Tyr Ala Tyr Leu Ala Ile Ala Glu Pro Trp Pro Lys Val Ser Gly Phe
            500                 505                 510

Ala Lys Val Asn Leu Phe Thr Gly Glu Val Lys Phe Ile Tyr Gly
        515                 520                 525

Asp Asn Lys Tyr Gly Gly Glu Pro Leu Phe Leu Pro Arg Asp Pro Asn
    530                 535                 540

Ser Lys Glu Glu Asp Asp Gly Tyr Ile Leu Ala Phe Val His Asp Glu
545                 550                 555                 560

Lys Glu Trp Lys Ser Glu Leu Gln Ile Val Asn Ala Met Ser Leu Lys
                565                 570                 575

Leu Glu Ala Thr Val Lys Leu Pro Ser Arg Val Pro Tyr Gly Phe His
            580                 585                 590

Gly Thr Phe Ile Asn Ala Asn Asp Leu Ala Asn Gln Ala
        595                 600                 605

<210> SEQ ID NO 17
<211> LENGTH: 1617
<212> TYPE: DNA
<213> ORGANISM: Arabidopsis thaliana
<220> FEATURE:
<221> NAME/KEY: CDS
<222> LOCATION: (1)..(1614)

<400> SEQUENCE: 17

```
atg gcg gag aaa ctc agt gat ggc agc atc atc atc tca gtc cat cct      48
Met Ala Glu Lys Leu Ser Asp Gly Ser Ile Ile Ile Ser Val His Pro
 1               5                  10                  15 aga ccc tcc aag ggt ttc tcc tcg aag ctt ctc gat ctt ctc gag aga      96
Arg Pro Ser Lys Gly Phe Ser Ser Lys Leu Leu Asp Leu Leu Glu Arg
            20                  25                  30 ctt gtc gtc aag ctc atg cac gat gct tct ctc cct ctc cac tac ctc     144
Leu Val Val Lys Leu Met His Asp Ala Ser Leu Pro Leu His Tyr Leu
         35                  40                  45 tca ggc aac ttc gct ccc atc cgt gat gaa act cct ccc gtc aag gat     192
Ser Gly Asn Phe Ala Pro Ile Arg Asp Glu Thr Pro Pro Val Lys Asp
     50                  55                  60 ctc ccc gtc cat gga ttt ctt ccc gaa tgc ttg aat ggt gaa ttt gtg     240
Leu Pro Val His Gly Phe Leu Pro Glu Cys Leu Asn Gly Glu Phe Val
 65                  70                  75                  80 agg gtt ggt cca aac ccc aag ttt gat gct gtc gct gga tat cac tgg     288
Arg Val Gly Pro Asn Pro Lys Phe Asp Ala Val Ala Gly Tyr His Trp
                 85                  90                  95 ttt gat gga gat ggg atg att cat ggg gta cgc atc aaa gat ggg aaa     336
Phe Asp Gly Asp Gly Met Ile His Gly Val Arg Ile Lys Asp Gly Lys
            100                 105                 110 gct act tat gtt tct cga tat gtt aag aca tca cgt ctt aag cag gaa     384
Ala Thr Tyr Val Ser Arg Tyr Val Lys Thr Ser Arg Leu Lys Gln Glu
        115                 120                 125 gag ttc ttc gga gct gcc aaa ttc atg aag att ggt gac ctt aag ggg     432
Glu Phe Phe Gly Ala Ala Lys Phe Met Lys Ile Gly Asp Leu Lys Gly
    130                 135                 140 ttt ttc gga ttg cta atg gtc aat atc caa cag ctg aga acg aag ctc     480
Phe Phe Gly Leu Leu Met Val Asn Ile Gln Gln Leu Arg Thr Lys Leu
145                 150                 155                 160 aaa ata ttg gac aac act tat gga aat gga act gcc aat aca gca ctc     528
Lys Ile Leu Asp Asn Thr Tyr Gly Asn Gly Thr Ala Asn Thr Ala Leu
                165                 170                 175 gta tat cac cat gga aaa ctt cta gca tta cag gag gca gat aag ccg     576
Val Tyr His His Gly Lys Leu Leu Ala Leu Gln Glu Ala Asp Lys Pro
            180                 185                 190 tac gtc atc aaa gtt ttg gaa gat gga gac ctg caa act ctt ggt ata     624
Tyr Val Ile Lys Val Leu Glu Asp Gly Asp Leu Gln Thr Leu Gly Ile
        195                 200                 205 ata gat tat gac aag aga ttg acc cac tcc ttc act gct cac cca aaa     672
Ile Asp Tyr Asp Lys Arg Leu Thr His Ser Phe Thr Ala His Pro Lys
    210                 215                 220 gtt gac ccg gtt acg ggt gaa atg ttt aca ttc ggc tat tcg cat acg     720
Val Asp Pro Val Thr Gly Glu Met Phe Thr Phe Gly Tyr Ser His Thr
225                 230                 235                 240 cca cct tat ctc aca tac aga gtt atc tcg aaa gat ggc att atg cat     768
Pro Pro Tyr Leu Thr Tyr Arg Val Ile Ser Lys Asp Gly Ile Met His
                245                 250                 255 gac cca gtc cca att act ata tca gag cct atc atg atg cat gat ttt     816
Asp Pro Val Pro Ile Thr Ile Ser Glu Pro Ile Met Met His Asp Phe
            260                 265                 270 gct att act gag act tat gca atc ttc atg gat ctt cct atg cac ttc     864
Ala Ile Thr Glu Thr Tyr Ala Ile Phe Met Asp Leu Pro Met His Phe
        275                 280                 285 agg cca aag gaa atg gtg aaa gag aag aaa atg ata tac tca ttt gat     912
Arg Pro Lys Glu Met Val Lys Glu Lys Lys Met Ile Tyr Ser Phe Asp
    290                 295                 300
```

```
ccc aca aaa aag gct cgt ttt ggt gtt ctt ccg cgc tat gcc aag gat      960
Pro Thr Lys Lys Ala Arg Phe Gly Val Leu Pro Arg Tyr Ala Lys Asp
305                 310                 315                 320 gaa ctt atg att aga tgg ttt gag ctt ccc aac tgc ttt att ttc cac     1008
Glu Leu Met Ile Arg Trp Phe Glu Leu Pro Asn Cys Phe Ile Phe His
                325                 330                 335 aac gcc aat gct tgg gaa gaa gag gat gaa gtc gtc ctc atc act tgt     1056
Asn Ala Asn Ala Trp Glu Glu Glu Asp Glu Val Val Leu Ile Thr Cys
            340                 345                 350 cgt ctt gag aat cca gat ctt gac atg gtc agt ggg aaa gtg aaa gaa     1104
Arg Leu Glu Asn Pro Asp Leu Asp Met Val Ser Gly Lys Val Lys Glu
        355                 360                 365 aaa ctc gaa aat ttt ggc aac gaa ctg tac gaa atg aga ttc aac atg     1152
Lys Leu Glu Asn Phe Gly Asn Glu Leu Tyr Glu Met Arg Phe Asn Met
    370                 375                 380 aaa acg ggc tca gct tct caa aaa aaa cta tcc gca tct gcg gtt gat     1200
Lys Thr Gly Ser Ala Ser Gln Lys Lys Leu Ser Ala Ser Ala Val Asp
385                 390                 395                 400 ttc ccc aga atc aat gag tgc tac acc gga aag aaa cag aga tac gta     1248
Phe Pro Arg Ile Asn Glu Cys Tyr Thr Gly Lys Lys Gln Arg Tyr Val
                405                 410                 415 tat gga aca att ctg gac agt atc gca aag gtt acc gga atc atc aag     1296
Tyr Gly Thr Ile Leu Asp Ser Ile Ala Lys Val Thr Gly Ile Ile Lys
            420                 425                 430 ttt gat ctg cat gca gaa gct gag aca ggg aaa aga atg ctg gaa gta     1344
Phe Asp Leu His Ala Glu Ala Glu Thr Gly Lys Arg Met Leu Glu Val
        435                 440                 445 gga ggt aat atc aaa gga ata tat gac ctg gga gaa ggc aga tat ggt     1392
Gly Gly Asn Ile Lys Gly Ile Tyr Asp Leu Gly Glu Gly Arg Tyr Gly
    450                 455                 460 tca gag gct atc tat gtt ccg cgt gag aca gca gaa gaa gac gac ggt     1440
Ser Glu Ala Ile Tyr Val Pro Arg Glu Thr Ala Glu Glu Asp Asp Gly
465                 470                 475                 480 tac ttg ata ttc ttt gtt cat gat gaa aac aca ggg aaa tca tgc gtg     1488
Tyr Leu Ile Phe Phe Val His Asp Glu Asn Thr Gly Lys Ser Cys Val
                485                 490                 495 act gtg ata gac gca aaa aca atg tcg gct gaa ccg gtg gca gtg gtg     1536
Thr Val Ile Asp Ala Lys Thr Met Ser Ala Glu Pro Val Ala Val Val
            500                 505                 510 gag ctg ccg cac agg gtc cca tat ggc ttc cat gcc ttg ttt gtt aca     1584
Glu Leu Pro His Arg Val Pro Tyr Gly Phe His Ala Leu Phe Val Thr
        515                 520                 525 gag gaa caa ctc cag gaa caa act ctt ata taa                         1617
Glu Glu Gln Leu Gln Glu Gln Thr Leu Ile
    530                 535

<210> SEQ ID NO 18
<211> LENGTH: 538
<212> TYPE: PRT
<213> ORGANISM: Arabidopsis thaliana

<400> SEQUENCE: 18

Met Ala Glu Lys Leu Ser Asp Gly Ser Ile Ile Ser Val His Pro
1               5                   10                  15

Arg Pro Ser Lys Gly Phe Ser Ser Lys Leu Leu Asp Leu Leu Glu Arg
                20                  25                  30

Leu Val Val Lys Leu Met His Asp Ala Ser Leu Pro Leu His Tyr Leu
            35                  40                  45

Ser Gly Asn Phe Ala Pro Ile Arg Asp Glu Thr Pro Pro Val Lys Asp
        50                  55                  60
```

-continued

```
Leu Pro Val His Gly Phe Leu Pro Glu Cys Leu Asn Gly Glu Phe Val
 65                  70                  75                  80

Arg Val Gly Pro Asn Pro Lys Phe Asp Ala Val Ala Gly Tyr His Trp
                 85                  90                  95

Phe Asp Gly Asp Gly Met Ile His Gly Val Arg Ile Lys Asp Gly Lys
            100                 105                 110

Ala Thr Tyr Val Ser Arg Tyr Val Lys Thr Ser Arg Leu Lys Gln Glu
        115                 120                 125

Glu Phe Phe Gly Ala Ala Lys Phe Met Lys Ile Gly Asp Leu Lys Gly
    130                 135                 140

Phe Phe Gly Leu Leu Met Val Asn Ile Gln Gln Leu Arg Thr Lys Leu
145                 150                 155                 160

Lys Ile Leu Asp Asn Thr Tyr Gly Asn Gly Thr Ala Asn Thr Ala Leu
                165                 170                 175

Val Tyr His His Gly Lys Leu Leu Ala Leu Gln Glu Ala Asp Lys Pro
            180                 185                 190

Tyr Val Ile Lys Val Leu Glu Asp Gly Asp Leu Gln Thr Leu Gly Ile
        195                 200                 205

Ile Asp Tyr Asp Lys Arg Leu Thr His Ser Phe Thr Ala His Pro Lys
    210                 215                 220

Val Asp Pro Val Thr Gly Glu Met Phe Thr Phe Gly Tyr Ser His Thr
225                 230                 235                 240

Pro Pro Tyr Leu Thr Tyr Arg Val Ile Ser Lys Asp Gly Ile Met His
                245                 250                 255

Asp Pro Val Pro Ile Thr Ile Ser Glu Pro Ile Met Met His Asp Phe
            260                 265                 270

Ala Ile Thr Glu Thr Tyr Ala Ile Phe Met Asp Leu Pro Met His Phe
        275                 280                 285

Arg Pro Lys Glu Met Val Lys Glu Lys Met Ile Tyr Ser Phe Asp
    290                 295                 300

Pro Thr Lys Lys Ala Arg Phe Gly Val Leu Pro Arg Tyr Ala Lys Asp
305                 310                 315                 320

Glu Leu Met Ile Arg Trp Phe Glu Leu Pro Asn Cys Phe Ile Phe His
                325                 330                 335

Asn Ala Asn Ala Trp Glu Glu Asp Glu Val Val Leu Ile Thr Cys
            340                 345                 350

Arg Leu Glu Asn Pro Asp Leu Asp Met Val Ser Gly Lys Val Lys Glu
        355                 360                 365

Lys Leu Glu Asn Phe Gly Asn Glu Leu Tyr Glu Met Arg Phe Asn Met
    370                 375                 380

Lys Thr Gly Ser Ala Ser Gln Lys Lys Leu Ser Ala Ser Ala Val Asp
385                 390                 395                 400

Phe Pro Arg Ile Asn Glu Cys Tyr Thr Gly Lys Lys Gln Arg Tyr Val
                405                 410                 415

Tyr Gly Thr Ile Leu Asp Ser Ile Ala Lys Val Thr Gly Ile Ile Lys
            420                 425                 430

Phe Asp Leu His Ala Glu Ala Glu Thr Gly Lys Arg Met Leu Glu Val
        435                 440                 445

Gly Gly Asn Ile Lys Gly Ile Tyr Asp Leu Gly Glu Gly Arg Tyr Gly
    450                 455                 460

Ser Glu Ala Ile Tyr Val Pro Arg Glu Thr Ala Glu Glu Asp Asp Gly
465                 470                 475                 480
```

```
Tyr Leu Ile Phe Phe Val His Asp Glu Asn Thr Gly Lys Ser Cys Val
            485                 490                 495

Thr Val Ile Asp Ala Lys Thr Met Ser Ala Glu Pro Val Ala Val Val
        500                 505                 510

Glu Leu Pro His Arg Val Pro Tyr Gly Phe His Ala Leu Phe Val Thr
    515                 520                 525

Glu Glu Gln Leu Gln Glu Gln Thr Leu Ile
    530                 535

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 19
attgaattca tgccttcagc ttcaaac                                      27

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 20
attggatccc aaaagctaca cgctggtccc c                                 31

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 21
atatatctag aatgccttca tcagcttcaa acacttgg                          38

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 22
atataggatc cctccggcac cggcgcgaag ttcccg                            36

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 23
cccgggatcc ctcaagcctc tctataccg                                    29

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Primer
```

```
<400> SEQUENCE: 24
cccgggatcc tttatacgga ttctgaggga g                                    31

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 25
attgaattca tggactctgt ttcttcttct tcc                                  33

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 26
attgaattct taaagcttat taaggtcact ttcc                                 34

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 27
aagaattcat ggcggagaaa ctcagtgatg gcagc                                35

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 28
aaaagaattc ggcttatata agagtttgtt cctgg                                35

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 29
cgggatccat gcaacactct cttcgttctg atcttcttc                            39

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 30
cgggatcctc agaaaacttg ttccttcaac tgattctcgc                           40

<210> SEQ ID NO 31
```

-continued

```
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 31
attgaattca tggcttcttt cacggcaacg gc                                    32

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 32
gttttcccag tcacgac                                                     17

<210> SEQ ID NO 33
<211> LENGTH: 538
<212> TYPE: PRT
<213> ORGANISM: Arabidopsis thaliana

<400> SEQUENCE: 33
```

Met Ala Glu Lys Leu Ser Asp Gly Ser Ile Ile Ile Ser Val His Pro
1               5                   10                  15

Arg Pro Ser Lys Gly Phe Ser Ser Lys Leu Leu Asp Leu Leu Glu Arg
            20                  25                  30

Leu Val Val Lys Leu Met His Asp Ala Ser Leu Pro Leu His Tyr Leu
        35                  40                  45

Ser Gly Asn Phe Ala Pro Ile Arg Asp Glu Thr Pro Pro Val Lys Asp
    50                  55                  60

Leu Pro Val His Gly Phe Leu Pro Glu Cys Leu Asn Gly Glu Phe Val
65                  70                  75                  80

Arg Val Gly Pro Asn Pro Lys Phe Asp Ala Val Ala Gly Tyr His Trp
                85                  90                  95

Phe Asp Gly Asp Gly Met Ile His Gly Val Arg Ile Lys Asp Gly Lys
            100                 105                 110

Ala Thr Tyr Val Ser Arg Tyr Val Lys Thr Ser Arg Leu Lys Gln Glu
        115                 120                 125

Glu Phe Phe Gly Ala Ala Lys Phe Met Lys Ile Gly Asp Leu Lys Gly
    130                 135                 140

Phe Phe Gly Leu Leu Met Val Asn Val Gln Gln Leu Arg Thr Lys Leu
145                 150                 155                 160

Lys Ile Leu Asp Asn Thr Tyr Gly Asn Gly Thr Ala Asn Thr Ala Leu
                165                 170                 175

Val Tyr His His Gly Lys Leu Leu Ala Leu Gln Glu Ala Asp Lys Pro
            180                 185                 190

Tyr Val Ile Lys Val Leu Glu Asp Gly Asp Leu Gln Thr Leu Gly Ile
        195                 200                 205

Ile Asp Tyr Asp Lys Arg Leu Thr His Ser Phe Thr Ala His Pro Lys
    210                 215                 220

Val Asp Pro Val Thr Gly Glu Met Phe Thr Phe Gly Tyr Ser His Thr
225                 230                 235                 240

Pro Pro Tyr Leu Thr Tyr Arg Val Ile Ser Lys Asp Gly Ile Met His
                245                 250                 255

Asp Pro Val Pro Ile Thr Ile Ser Glu Pro Ile Met Met His Asp Phe

-continued

```
                260                 265                 270
Ala Ile Thr Glu Thr Tyr Ala Ile Phe Met Asp Leu Pro Met His Phe
            275                 280                 285
Arg Pro Lys Glu Met Val Lys Glu Lys Lys Met Ile Tyr Ser Phe Asp
        290                 295                 300
Pro Thr Lys Lys Ala Arg Phe Gly Val Leu Pro Arg Tyr Ala Lys Asp
305                 310                 315                 320
Glu Leu Met Ile Arg Trp Phe Glu Leu Pro Asn Cys Phe Ile Phe His
                325                 330                 335
Asn Ala Asn Ala Trp Glu Glu Glu Asp Glu Val Val Leu Ile Thr Cys
            340                 345                 350
Arg Leu Glu Asn Pro Asp Leu Asp Met Val Ser Gly Lys Val Lys Glu
        355                 360                 365
Lys Leu Glu Asn Phe Gly Asn Glu Leu Tyr Glu Met Arg Phe Asn Met
        370                 375                 380
Lys Thr Gly Ser Ala Ser Gln Lys Lys Leu Ser Ala Ser Ala Val Asp
385                 390                 395                 400
Phe Pro Arg Ile Asn Glu Cys Tyr Thr Gly Lys Lys Gln Arg Tyr Val
                405                 410                 415
Tyr Gly Thr Ile Leu Asp Ser Ile Ala Lys Val Thr Gly Ile Ile Lys
            420                 425                 430
Phe Asp Leu His Ala Glu Ala Glu Thr Gly Lys Arg Met Leu Glu Val
        435                 440                 445
Gly Gly Asn Ile Lys Gly Ile Tyr Asp Leu Gly Glu Gly Arg Tyr Gly
    450                 455                 460
Ser Glu Ala Ile Tyr Val Pro Arg Glu Thr Ala Glu Glu Asp Asp Gly
465                 470                 475                 480
Tyr Leu Ile Phe Phe Val His Asp Glu Asn Thr Gly Lys Ser Cys Val
                485                 490                 495
Thr Val Ile Asp Ala Lys Thr Met Ser Ala Glu Pro Val Ala Val Val
            500                 505                 510
Glu Leu Pro His Arg Val Pro Tyr Gly Phe His Ala Leu Phe Val Thr
        515                 520                 525
Glu Glu Gln Leu Gln Glu Gln Thr Leu Ile
    530                 535
```

TRANSGENIC PLANTS CARRYING NEOXANTHIN CLEAVAGE ENZYME GENE

This application is a division of application Ser. No. 09/758,269, filed Jan. 12, 2001, now U.S. Pat. No. 7,049,487.

FIELD OF THE INVENTION

The present invention relates to a DNA for improving or reducing stress tolerance in a plant, and a transgenic plant of the DNA.

BACKGROUND OF THE INVENTION

Plants must adapt themselves to various stresses, for example, drought, salt in the soil, and low temperature because they can not move freely. Among these stresses, drought is thought to effect plant growth the most severely. In order to survive in drought condition, some plants have acquired a physiologically and/or morphologically specific trait in the evolutional process while many other plants also confer a mechanism to response to the drought stress and defend themselves. These responses to a shortage of water and adaptation to drought environment in plants are caused by various physiological changes including the alternation of gene expression at drought (Shinozaki, K and Yamaguchi-Shinozaki, K., Plant Physiol., 115: 327-334, 1997; Shinozaki, K. and Yamaguchi-Shinozaki, K., "Molecular responses to drought stress." In Shinozaki and Yamaguchi-Shinozaki (eds), "Molecular responses to cold, drought, heat and salt stress in higher plants," R. G. LANDES company, Austin, Tex., USA, pp. 11-28, 1999). For example, in *Arabidopsis* (*Arabidopsis thaliana*), it is known that a drought signal is transmitted through an abscisic acid (ABA) dependent pathway and ABA independent pathway to control the gene expression involved in drought tolerance. These gene products are thought to have a function in controlling, for example, accumulation of osmoprotectants such as sucrose and proline, half life of proteins, stress signal transduction pathway, and transcription (Bray, E. A., Trends in Plant Science, 2: 48-54, 1997; Bohnert, H. J. et al., Plant Cell, 7: 1099-1111, 1995; Ingram, J. and Bartels, D., Annu. Rev. Plant Physiol. Plant Mol. Biol., 47: 377-403, 1996; Shinozaki, K. and Yamaguchi-Shinozaki, K., Plant Physiol., 115: 327-334, 1997; Shinozaki, K. and Yamaguchi-Shinozaki, K., "Molecular responses to drought stress." In Shinozaki and Yamaguchi-Shinozaki (eds), "Molecular responses to cold, drought, heat and salt stress in higher plants," R. G. LANDES company, Austin, Tex., USA, pp. 11-28, 1999).

C40 pathway has been proposed as a biosynthetic pathway of ABA in higher plants. The C40 pathway, also called a carotenoid pathway, is a synthetic pathway through epoxydation of zeaxanthin, synthesizing violaxanthin, neoxanthin, xanthoxin, ABA aldehyde, and then ABA (Zeevaart, J. A. D. and Creelman R. A., Ann. Rev. Plant Physiol. Plant Mol. Biol., 39: 439-473, 1988). This biosynthetic pathway has been proposed from physiological studies and analyses of ABA biosynthetic variants. For example, variant aba2 isolated from tobacco (*Nicotiana tabacum*) has a mutation in a gene (aba2) of zeaxanthin epoxidase enzyme which catalyzes the epoxidation of zeaxanthin (Marin E. et al., EMBO J., 15: 2331-2342, 1996). Variant vp14 isolated from maize has a mutation in a gene (VP14) of neoxanthin cleavage enzyme which catalyzes the conversion from a neoxanthin to xanthoxin (Tan, B. C. et al., Proc. Natl. Acad. Sci. USA, 94: 12235-12240, 1997). From *Arabidopsis* plants, variant aba3 having a mutation in an enzyme which catalyzes a reaction from xanthoxin to ABA aldehyde, and variant aba4 involved in the reaction for oxidizing ABA aldehyde to produce ABA have been isolated (Schwartz, S. H. et al., Plant Physiol., 114: 161-166, 1997; Leon-Kloosterziel, K. M. et al., Plant J., 10: 655-661, 1996).

A maize having a mutation in a neoxanthin cleavage enzyme gene (VP14) is known to show a trait of easily loosing water and easily wilting. It has not been known yet, however, whether stress tolerance in plants can be improved or not using the neoxanthin cleavage enzyme gene.

SUMMARY OF THE INVENTION

An objective of the present invention is to provide a DNA encoding a neoxanthin cleavage enzyme used for improving stress tolerance in a plant, a method for increasing stress tolerance in a plant by introducing the DNA into the plant, and a transgenic plant into which a neoxanthin cleavage enzyme gene is introduced. Another objective of the present invention is to provide a DNA used for reducing stress tolerance in a plant, a method for decreasing stress tolerance in a plant by introducing the DNA into the plant, and a transgenic plant into which the DNA is introduced. The improvement of stress tolerance in plants is useful, for example, in plant breeding.

The present inventors have isolated a cDNA clone (CPRD65) corresponding to a gene involved in a response against drought treatment, by the differential screening of a cDNA library prepared from a cowpea plant (*Vigna unguiculata*) which showed extensive drought tolerance after dehydration treatment for 10 hours. The CPRD65 cDNA was expected to encode a neoxanthin cleavage enzyme proposed to be involved in biosynthesis of abscisic acid (ABA). Drought stress given to an 8-day-old cowpea plant strongly induced the accumulation of ABA and the expression of the CPRD65, indicating the potential of the profound involvement of CPRD65 gene, especially in the response to drought stress. Determination of an enzyme activity using GST-CPRD65 fusion protein confirmed that the CPRD65 comprises an activity of cleaving 9-cis-neoxanthin to produce xanthoxin. These results indicate that the CPRD65 gene encodes a neoxanthin cleavage enzyme and its product plays a key role in endogenous ABA biosynthesis under drought stress.

Moreover, the present inventors have isolated a novel gene (AtNCED3) by screening a neoxanthin cleavage enzyme gene from an *Arabidopsis* plant-derived cDNA library using a cDNA of the CPRD65 gene isolated from cowpea plants as a probe. In addition, four types of sequences (AtNCED1, 2, 4, and 5) derived from an *Arabidopsis* plant comprising high homology with these genes were identified. Expression of these genes in *Escherichia coli* (*E. coli*) and assay of a neoxanthin cleavage activity revealed that AtNCED1, 3, and 5 comprise a neoxanthin cleavage enzyme activity same as the CPRD65.

The present inventors first produced a transgenic plant of *Arabidopsis* using AtNCED3, a neoxanthin cleavage enzyme gene. The AtNCED3 gene was ligated downstream of 35S promoter in a vector for introducing a gene into plant cells (pBE2113N) in the directions of sense (an overexpression type) or antisense (an expression inhibition type) and introduced the vector into *Arabidopsis* by the vacuum infiltration method. Evaluation of drought tolerance of the prepared transgenic plants revealed that stress tolerance in the overexpressed plants was significantly increased compared with that in their parent lines. In contrast, in the expression-inhibited lines into which the antisense was introduced, stress tolerance was reduced (FIGS. 15 and 16). In such a manner, the present inventors found that actually the transgenic plant into which the neoxanthin cleavage enzyme gene is introduced significantly increased stress tolerance and stress tolerance can be significantly reduced by decreasing the expression of the gene to complete the present invention.

Specifically, this invention relates to a DNA encoding a neoxanthin cleavage enzyme used for improving stress tolerance in a plant, a method for increasing stress tolerance in a plant by introducing the DNA into the plant, and a transgenic plant into which a neoxanthin cleavage enzyme gene is introduced, as well as a DNA used for reducing stress tolerance in a plant, a method for decreasing stress tolerance in a plant by introducing the DNA into the plant, and a transgenic plant into which the DNA is introduced, and more specifically, the present invention provides:

(1) an isolated DNA encoding a protein having a neoxanthin cleavage activity for improving stress tolerance in a plant, (2) an isolated DNA for reducing stress tolerance in a plant, wherein the DNA is selected from the group consisting of:

(a) a DNA encoding an antisense RNA complementary to a transcript of a gene encoding a protein having a neoxanthin cleavage activity;

(b) a DNA encoding an RNA comprising a ribozyme activity which cleaves a transcript of a gene encoding a protein having a neoxanthin cleavage activity; and (c) a DNA encoding an RNA which inhibits the expression of a gene encoding a protein having a neoxanthin cleavage in a plant cell by the cosuppression effect, (3) the DNA of (1) or (2), wherein the protein having a neoxanthin cleavage activity is selected from the group consisting of:

(a) a protein comprising an amino acid sequence of SEQ ID NOs: 2 (AtNCED1), 6 (AtNCED3), 10 (AtNCED5), 12 (CPRD65), 14 (VP14), or 16 (LeNCED1), (b) a protein comprising an amino acid sequence in which one or more amino acids in SEQ ID NOs: 2 (AtNCED1), 6 (AtNCED3), 10 (AtNCED5), 12 (CPRD65), 14 (VP14), or 16 (LeNCED1) are replaced, deleted, added, and/or inserted, and (c) a protein encoded by a DNA which hybridizes with a DNA comprising a nucleotide sequence of SEQ ID NOs: 1 (AtNCED1), 5 (AtNCED3), 9 (AtNCED5), 11 (CPRD65), 13 (VP14), or 15 (LeNCED1) under the stringent condition, (4) the DNA of any one of (1) to (3), wherein the protein having a neoxanthin cleavage activity is derived from *Arabidopsis* plants, (5) a transformant plant cell carrying the DNA of any one of (1) to (4), (6) a transgenic plant comprising the transformant plant cell of (5), (7) a transgenic plant which is offspring or a clone of the transgenic plant of (6), (8) the transgenic plant of (6) or (7), wherein the expression of a gene encoding a protein having a neoxanthin cleavage activity is increased or decreased compared with its wild type, (9) the transgenic plant of any one of (6) to (8), wherein the amount of abscisic acid is increased or decreased compared with its wild type,

(10) the transgenic plant of any one of (6) to (9), wherein stress tolerance is increased or decreased compared with its wild type,

(11) a propagation material for the transgenic plant of any one of (6) to (10),

(12) a vector comprising the DNA of any one of (1) to (4),

(13) a method for producing the transgenic plant of any one of (6) to (10), comprising the steps of introducing the DNA of any one of (1) to (4) into a plant cell and regenerating a plant from the plant cell,

(14) a method for increasing or decreasing stress tolerance in a plant, comprising expressing the DNA of any one of (1) to (4) in a plant cell, In the present invention, "stress tolerance" means tolerance against environmental stresses, for example, drought stress tolerance, salt stress tolerance, low temperature stress tolerance, air pollution tolerance, tolerance to low oxygen condition, pathogen tolerance, drug tolerance such as those to agrochemicals, etc. Exogenous treatment with ABA has known to improve tolerance against these stresses in many plants (refer to Takahashi, N. and Masuda, Y. (eds), "Plant Hormone Handbook (The Last)," Baifukan, Japan, pp. 78-160; and references cited therein).

BRIEF DESCRIPTION OF THE DRAWINGS

FIG. 1 shows Northern blot analysis of the expression of the CPRD65 genes upon dehydration or rehydration. Total RNA was prepared from 8-day-old cowpea plants that had been dehydrated for 0, 1, 2, 4, 6, 8, 10, and 12 hours or rehydrated for 0, 1, 2, 5, 10, and 24 hours after dehydration for 10 hours. Each lane was loaded with 10 µg of total RNA. The RNA was fractionated on a 1% agarose gel, blotted onto a nylon membrane, and probed with [$^{32}$P]-labeled cDNA inserts of the CPRD65 clones.

FIG. 2 shows comparison of the deduced amino acid sequences of the CPRD65, VP14 (neoxanthin cleavage enzyme from *Zea mays*, Schwartz, S. H. et al., Science, 276: 1872-1874, 1997), and LeNCED1 protein (neoxanthin cleavage enzyme from *Lycopersicon esculentum*, Burbidge, A. et al., J. Exp. Bot., 47: 2111-2112, 1997; Burbidge, A. et al., Plant J., 17: 427-431, 1999). Dashes indicate gaps that were introduced to optimize the alignment. Enclosed boxes indicate identical amino acids. Shadowed regions indicate similar amino acids.

FIG. 4(A) shows Northern blot analysis of the induction of the CPRD65 gene by high salinity (NaCl), high temperature (heat), low temperature (cold), and the application of abscisic acid (ABA). Total RNA was isolated from the cowpea plants at the indicated hours after the treatment. Each lane was loaded with 10 µg of total RNA. The number above each lane indicates the duration (hours) of the treatment.

FIG. 4(B) shows Northern blot analysis of the CPRD65 gene without or with 10 hour-dehydration treatment. Each lane was loaded with 10 µg of total RNA isolated from leaves (L), stems (S), and roots (R) of cowpea 2246 cultivar. The RNA was fractionated on a 1% agarose gel, blotted onto a nylon membrane, and probed with [$^{32}$P]-labeled cDNA inserts of the CPRD65.

FIG. 5 shows HPLC profiles of carotenoid metabolites of GST (A) or the GST-CPRD65 recombinant protein (B). The reaction mixture contained cis-neoxanthin as a substrate. cN; cis-neoxanthin, C25; C25-product.

FIG. 9 shows comparison of the deduced amino acid sequences of AtNCED3 and CPRD65. Dashes indicate gaps that were introduced to optimize the alignment. Enclosed boxes indicate identical amino acids. Shadowed regions indicate similar amino acids.

FIG. 10 shows alignments of amino acid sequences of AtNCED1, 2, 3, 4, and 5. Dashes indicate gaps that were introduced to optimize the alignment. Enclosed boxes indicate identical amino acids. Shadowed regions indicate similar amino acids.

FIG. 15 shows the result of testing drought tolerance in neoxanthin cleavage enzyme transgenic plants, indicating the plants and relative water content in the leaves 14 days after the termination of the irrigation.

DETAILED DESCRIPTION OF THE INVENTION

Figure 3:
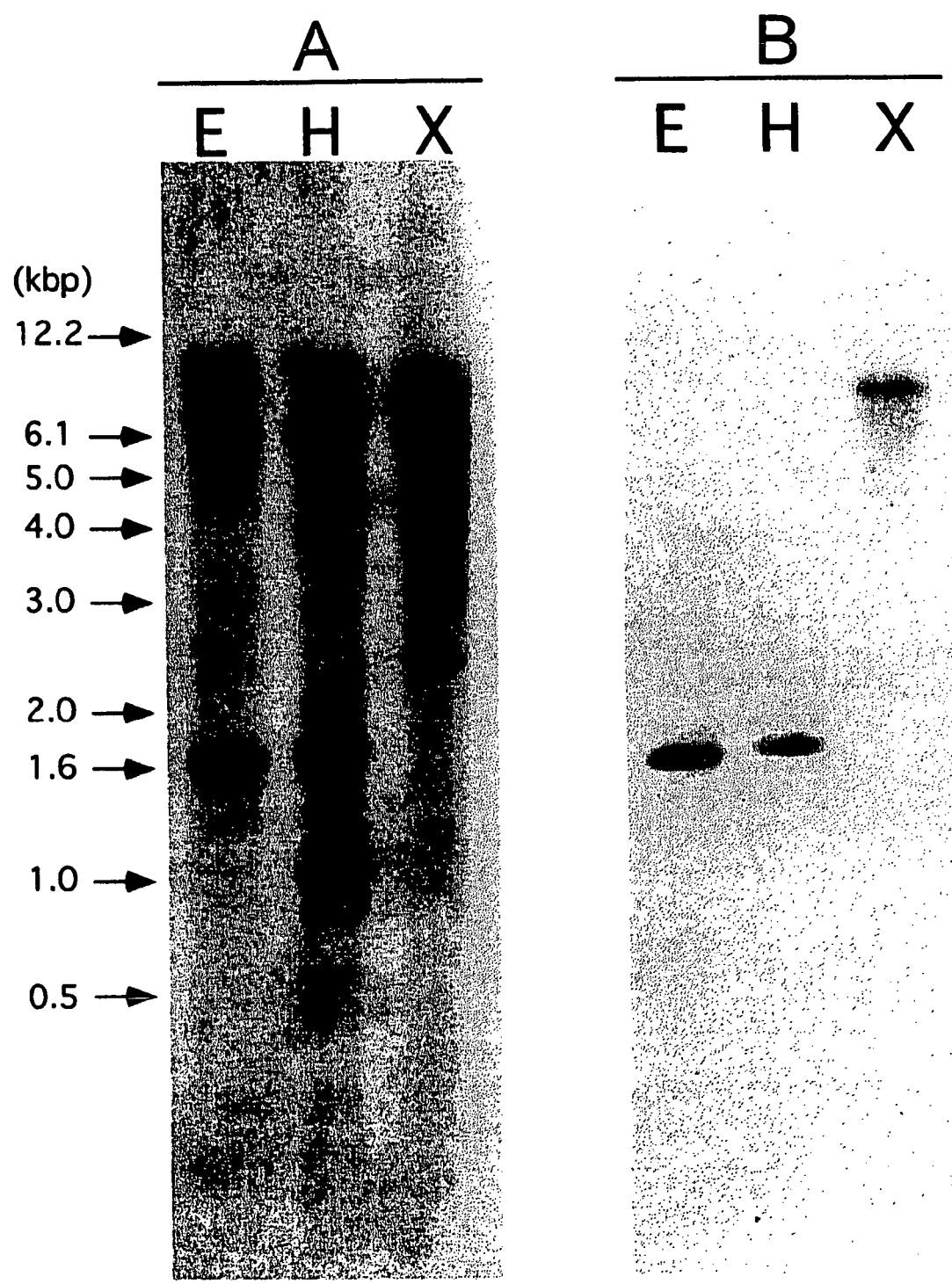
FIG. 3 shows Southern blot analysis of genomic DNA from cowpea 2246 cultivar. Genomic DNA (10 µg per lane) was digested with EcoRI (E), HindIII (H), and XbaI (X), fractionated on a 1% agarose gel, and transferred to a nylon membrane. The filter was allowed to hybridize with a [$^{32}$P]-labeled fragment of the CPRD65 cDNA. "A" and "B" represent different stringency in hybridization conditions (refer to Examples). The size marker of DNA fragments is indicated in kbp.

The present invention relates to an isolated DNA encoding a protein having a neoxanthin cleavage activity used for improving stress tolerance. A neoxanthin cleavage enzyme has been known as an enzyme involved in the ABA biosynthesis, however, has not been confirmed whether introduction of the DNA encoding this enzyme into a plant actually leads to ABA accumulation and improvement of tolerance against stresses without a grave effect to plant's growth.

Exogenous treatment with ABA causes, for example, growth inhibition in many plants. In a seed, it is known that ABA also causes growth inhibition (germination inhibition) (Takahashi, N. and Masuda, Y. (eds), "Plant Hormone Handbook (The Last)," Baifukan, Japan, pp. 78-160; and references cited therein). Increase in ABA level brings about various damages to plants. There has been no report whether excessive production of ABA by an exogenous gene leads to acquirement of stress tolerance or not. The conventional experimental procedures for exogenous treatment with ABA require the treatment at high concentration, which strongly inhibits the growth and has prevented accurate evaluation of tolerance. Furthermore, experiments of exogenous treatments have not identified that an appropriate level of ABA ensures normal growth and acquirement of tolerance. By obtaining ABA biosynthesis gene and creating a transgenic plant using this gene, the present inventors have first confirmed that stress tolerance in a plant can be improved.

An "isolated DNA" is a DNA the structure of which is not identical to that of any naturally occurring DNA or to that of any fragment of a naturally occurring genomic DNA spanning more than three separate genes. The term therefore includes, for example, (a) a DNA which has the sequence of part of a naturally occurring genomic DNA molecule in the genome of the organism in which it naturally occurs; (b) a DNA incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are DNA molecules present in mixtures of different (i) DNA molecules, (ii) transfected cells, or (iii) cell clones; e.g., as these occur in a DNA library such as a cDNA or genomic DNA library.

As an isolated DNA used for increasing stress tolerance, any genes can be used as long as it encodes a protein having a neoxanthin cleavage activity. For example, VP14 of maize (*Zea mays*) (Schwartz, S. H. et al., Science, 276: 1872-1874, 1997; Tan, B. V. et al., Proc. Natl. Acad. Sci. USA, 94: 12235-12240, 1997) (cDNA: SEQ ID NO: 13, protein: SEQ ID NO: 14), LeNCED1 of tomato (*Lycopersicon esculentum*) (Burbidge, A. et al., J. Exp. Bot., 47: 2111-2112, 1997; Burbidge, A. et al., Plant J., 17: 427-431, 1999) (cDNA: SEQ ID NO: 15, protein: SEQ ID NO: 16), and such have been isolated as neoxanthin cleavage enzyme genes. These genes are useful for improving stress tolerance and can be used for the present invention. In addition, DNAs encoding AtNCED1 (SEQ ID NO: 2), AtNCED3 (SEQ ID NO: 6), AtNCED5 (SEQ ID NO: 10), and CPRD65 (SEQ ID NO: 12) (SEQ ID NOs: 1, 5, 9, and 11, respectively) can be conveniently used. Moreover, a DNA encoding a neoxanthin cleavage enzyme of SEQ ID NO: 18 (cDNA: SEQ ID NO: 17, protein: SEQ ID NO: 18) (Neill, S. J. et al., J. Exp. Bot., 49: 1893-1894, 1998, Ac. No. AJ005813) can also be used in this invention. A DNA encoding a protein having a neoxanthin cleavage activity can also be used as a reagent for increasing stress tolerance (stress tolerance increasing agent). The present invention also provides uses of a DNA encoding a protein having a neoxanthin cleavage activity for increasing stress tolerance.

A DNA encoding a protein having a neoxanthin cleavage activity in the present invention includes a genomic DNA, a cDNA, and a chemosynthetic DNA. A genomic DNA and a cDNA can be prepared by common methods for one skilled in the art. A genomic DNA can be prepared, for example, by extracting a genomic DNA from a plant according to conventional methods, in which a genomic library is prepared (in which, as a vector, for example, a plasmid, a phage, a cosmid, and a BAC can be used), and colony hybridization or plaque hybridization is conducted using a probe based on the DNA of the present invention (for example, SEQ ID NOs: 1, 5, 9, 11, 13, 15, etc.). Alternatively, a genomic DNA can also be prepared by conducting PCR with primers specific to the DNA of the present invention (for example, SEQ ID NOs: 1, 5, 9, 11, 13, 15, etc.). A cDNA can be prepared by synthesizing a cDNA based on a mRNA extracted from a plant, inserting the cDNA into a vector, such as λ phage to prepare and develop a cDNA library, and conducting colony hybridization or plaque hybridization in the same manner as above, or performing PCR. A DNA of the present invention includes not only DNA sequences of SEQ ID NOs: 1, 5, 9, 11, 13, and 15, but a DNA comprising nucleotide sequences based on an optional degeneracy of codons encoding amino acids of each protein.

A DNA of the present invention also includes, for example, a DNA encoding a protein that comprises an amino acid sequence in which one or more amino acids are replaced, deleted, added, and/or inserted in SEQ ID NOs: 2, 6, 10, 12, 14, or 16, and has a neoxanthin cleavage activity. Thus, the DNA of the invention includes a mutant, a derivative, an allele, a variant, and a homolog of SEQ ID NOs: 1, 5, 9, 11, 13, or 15, a gene derived from a natural plant.

A modified protein encoded by the DNA of the invention comprises an amino acid sequence at least 70% (e.g., 80%, 90%, 95%, or 99%) identical to SEQ ID NOs: 2, 6, 10, 12, 14, or 16. As used herein, "percent identity" of two amino acid sequences or of two nucleic acids is determined using the algorithm of Karlin and Altschul (Proc. Natl. Acad. Sci. USA 87: 2264-2268, 1990) modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. BLAST protein searches are performed with the XBLAST program, score=50, wordlength=3. Where gaps exist between two sequences, Gapped BLAST is utilized as described in Altsuchl et al. (Nucleic Acids Res. 25: 3389-3402, 1997). When utilizing BLAST and Gapped BLAST programs, the default parameters of the respective programs (e.g, XBLAST and NBLAST) are used. See http://www.ncbi.nlm.nih.gov.

The modified protein in which one or more amino acids are replaced in SEQ ID NOs: 2, 6, 10, 12, 14, or 16 is preferably obtained by at least one conservative amino acid substitution. A "conservative amino acid substitution" is a replacement of one amino acid residue belonging to one of the following groups having a chemically similar side chain with another amino acid in the same group. Groups of amino acid residues having similar side chains have been defined in the art. These groups include amino acids with basic side chains (e.g., lysine, arginie, histidine), acidic side chains (e.g., aspartic acid, glutamic acid), uncharged polar side chains (e.g., glycine, aspargine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

An example of a method for preparing such a DNA encoding a protein having a modifiend amino acid sequence, well-known to one skilled in the art, is in vitro mutagenesis utilizing PCR (Izawa, T., "in vitro mutagenesis by PCR" in Shimamoto, K. and Sasaki, T. (supervisors), Cell Technology, Supplement, Plant Cell technology Series VII, Protocols for PCR Experiments in Plants, New Edition, pp. 151-158, Shujunsha, Japan). Modification of amino acids in a protein, is ordinarily within 200 amino acids, preferably within 100 amino acids, more preferably within 50 amino acids, and further more preferably within 10 amino acids in the case of artificial modification. Modification of an amino acid sequence of a protein due to modification of the encoding nucleotide sequence can occur in nature. A DNA encoding a protein having an amino acids sequence in which one or more amino acids are replaced, deleted, added, and/or inserted in an amino acid sequence encoding a wild-type neoxanthin cleavage enzyme is even included in the DNA of the present invention as long as it encodes a protein having a neoxanthin cleavage activity. The DNA of the present invention also includes a degenerate variant in which a mutation in a nucleotide sequence does not result in a mutation of amino acids in a protein.

Whether a given DNA encodes a neoxanthin cleavage enzyme or not can be determined by expressing the DNA in *E. coli* to prepare a recombinant protein and detecting the cleavage using a cis-neoxanthin as a substrate, according to Example 5 below.

Based on a DNA encoding a known neoxanthin cleavage enzyme, a novel neoxanthin cleavage enzyme gene can be isolated. Examples of methods well-known by one skilled in the art for this purpose are methods using hybridization technique (Maniatis, T et al., 1982, Molecular Cloning: A Laboratory Manual, Cold Spring Harbor, N.Y., Cold Spring Harbor Laboratory Press) and polymerase chain reaction (PCR) techniques (Nakayama, H., Cell Technology, Supplement, Biological Experiment Illustrated, Vol. 3, New Edition, Shujunsha, 1998). Specifically, one skilled in the art can routinely isolate a DNA encoding a neoxanthin cleavage enzyme gene from any plant by using a nucleotide sequence of a known neoxanthin cleavage enzyme gene (for example, SEQ ID NOs: 1, 5, 9, 11, 13, 15, etc.) or its partial sequence as a probe, as well as an oligonucleotide specifically hybridized with these sequences as a primer. A DNA encoding a neoxanthin cleavage enzyme, capable of being isolated by such hybridization technique or PCR technique is also included in a DNA used for improving stress tolerance in the present invention.

Hybridization can be performed under stringent condition by following, for example, the method described in reference (Sambrook, J., et al., "Molecular Cloning: A Laboratory Manual" 2nd ed, Cold Spring Harbor Laboratory Press, Cold Spring Harbor, N.Y., 1989) using a [$^{32}$P]-labeled DNA prepared by using a random prime method as a probe. A DNA is blotted to a nylon membrane and hybridized with a [$^{32}$P]-labeled fragment, for example, in a hybridization solution containing 30%, preferably 50% formamide, 6×SSC, 5× Denhardt's solution, and 100 µg/ml denatured salmon sperm DNA, at 37° C., preferably at 42° C. Under a stringent condition, washing is, for example, in 1×SSC, 1% SDS (room temperature), for 15 min twice, preferably (more stringent) in 0.5×SSC, 0.5% SDS (37° C.), for 15 min twice, and more preferably (further stringent) 0.1×SSC, 0.1% SDS (60° C.) for 15 min twice, and subjected to autoradiography. By "hybridizes under stringent conditions" is meant specific and non-covalent equilibrium binding by base-pairing to an immobilized reference nucleic acid under the above conditions.

In order to prepare a transgenic plant with improved stress tolerance using these DNAs, the DNA is inserted into an appropriate vector, and introduced the vector into a plant cell, and a transgenic plant is regenerated from the transformant plant cell.

As a vector used for transformation of a plant cell, any vector capable of expressing an inserted gene in the cell can be used. For example, a vector comprising a promoter for constantly expressing a gene in a plant cell (for example, 35S promoter of cauliflower mosaic virus) and a vector with a promoter inducibly activated by an exogenous stimulus can be used. Alternatively, by using a promoter specific to a plant tissue to induce the expression of an objective gene, stress tolerance can be provided specifically to a tissue highly sensitive to the stress. For example, an objective gene can be expressed specifically to a tissue by using a promoter of a gene specifically expressing in seeds, such as that of β-phaseolin gene of kidney beans (Bustos et al., EMBO J., 10: 1469-1479, 1991) and that of glycinin gene of soybean (Lelievre et al., Plant Physiol., 98: 387-391, 1992), a promoter of a gene expressing specifically in leaves, such as that of RbcS gene of pea (Lam and Chua, Science, 248: 471-474, 1990) and that of Cab1 gene of wheat (Gotorn et al., Plant J., 3: 509-518, 1993), and a promoter of a gene expressing specifically to roots, such as that of TobRB7 gene of tobacco (Yamamoto et al., Plant Cell, 3: 371-382, 1991), etc. Alternatively, a vector comprising a promoter inducibly activated by an exogenous stimulus can be used. An example of a promoter responding to environmental stresses, such as drought, salt, or low temperature, is a promoter of rd29A gene (Yamaguchi-Shinozaki, K. and Shinozaki, K., Plant Cell, 6: 251-264, 1994). A promoter to be activated by environmental stresses such as drought and high salt concentration is also preferably used in the present invention. Examples of such promoters are those of *Arabidopsis* AtNCED3 gene, cowpea CPRD65 gene, and so on. Moreover, by using an expression system inducible by a drug, an objective gene can be expressed at an optional timing and in an optional tissue. An example of an expression system induced by steroid hormone (glucocorticoid) is an induction system using GVG gene (GAL4, VP16, Glucocorticoid receptor) (Aoyama T. and Chua, N. H., Plant J, 11: 605-12, 1997).

A vector can be inserted into any plant cells, for example, *Arabidopsis* (*Arabidopsis thaliana*), rice (*Oriza sativa*), tobacco (*Nicotiana tabacum*), tomato (*Lycopersicon esculentum*), potato (*Solanum tuberosum*), maize (*Zea mays*), bird's foot trefoil (*Lotus japonicus*), and so on. Other crops or trees are also useful. A plant can be a conifer, a broad-leaved tree, a dicot, a monocot, etc. "Plant cell(s)" used herein include various forms of plant cells, for example, a suspended cultured cell, a protoplast, a leaf slice, a callus, etc.

For introduction of a vector into a plant cell, various methods known to one skilled in the art, for example, polyethylene glycol method, electroporation method, *agrobacterium* method, vacuum infiltration method, particle gun method, and such can be applied. A plant can be regenerated from a transformant plant cell by methods well-known to one skilled in the art, depending on a type of a plant cell. For example, a transformant of rice, *Arabidopsis*, or such can be prepared according to the method described in "Simamoto, K., Okada K. (supervisors), Cell Technology, Supplement, Plant cell Technology Series 4, Experimental Protocol for Model Plants, Shujunsha, Japan."

Once a transformant plant into which genome the DNA of the present invention is introduced is obtained, offspring can be obtained by sexual or asexual propagation from the plant. Alternatively, a propagation material (for example, a seed, a fruit, a scion, a tuber, a tuberous root, a stock, a callus, a protoplast, etc.) is obtained from the plant, its offspring, or clones, and the plant can be mass-produced from them. The present invention includes a plant cell into which the DNA of the present invention is introduced, a plant containing the cell, offspring or a clone of the plant, as well as propagation materials for the plant, its offspring, and clone.

A transformant plant produced in such a manner has an increased ABA content, compared with its wild type plant. Alternatively, a transformant plant has improved stress tolerance, compared with its wild type plant. Stress tolerance can be compared by a known method. For example, as described in Examples below, a plant is grown under the stress condition, such as drought, high salt, low temperature, or heat condition, and the growth of individuals is compared. For example, comparison can be made by measuring an appearance, a size of a plant or of a tissue such as a leaf, a stem, and a root, a weight (wet weight or dry weight), color, a relative growth rate, a photosynthetic activity, etc. as an index. Stress tolerance may increase in at least one tissue of a plant. A level of ABA in a plant can be determined by, for example, immunoassay, thin layer chromatography (TLC), gas chromatography (GC), and HPLC (refer to Takahashi, N. and Masuda, Y. (eds), "Plant Hormone Handbook (The Last)," Baifukan, Japan, pp. 1-21; and the references cited therein). For example, as described in Example 7, reliable quantification is possible by finally quantifying crude purified fraction by HPLC with GC/MS, using labeled ABA as an internal standard.

By the present invention, a useful crop can be grown in an area exposed to environmental stress, for example, a drought zone, a cold zone, or high concentration of salt. In addition, the present invention can be applied to plants other than crops for tree-planting environment.

The present invention also relates to a DNA which can decrease the expression of a gene encoding a protein having a neoxanthin cleavage activity to be used for lowering stress tolerance. The DNA can also be used as a reagent for decreasing stress tolerance (stress tolerance decreasing agent). The present invention also provides uses of a DNA which can decrease the expression of a gene encoding a protein having a neoxanthin cleavage activity for decreasing stress tolerance.

A plant with reduced stress tolerance is useful for removing weeds and such from the environment, by applying to weeds and such. For example, a plant capable of inducing the decrease in stress tolerance can be prepared to apply for land improvement and such. To a plant with high regeneration ability, such as weed, a construct which inhibits the expression of a neoxanthin cleavage enzyme gene (for example, in the antisense direction) is introduced to downstream of a promoter inducible with a chemical (for example, glucocorticoid and soon). This transformant plant can normally grow without the application of the chemical. An arid land can be improved by growing the transformant weed for several years, spraying glucocorticoid to remove the weed at once by specifically lowering stress tolerance in the weed, and planting a crop plant. As a crop plant, a transformant crop which overexpresses a neoxanthin cleavage enzyme (a plant into which the DNA is introduced in sense direction) and such can be planted.

Figure 16:
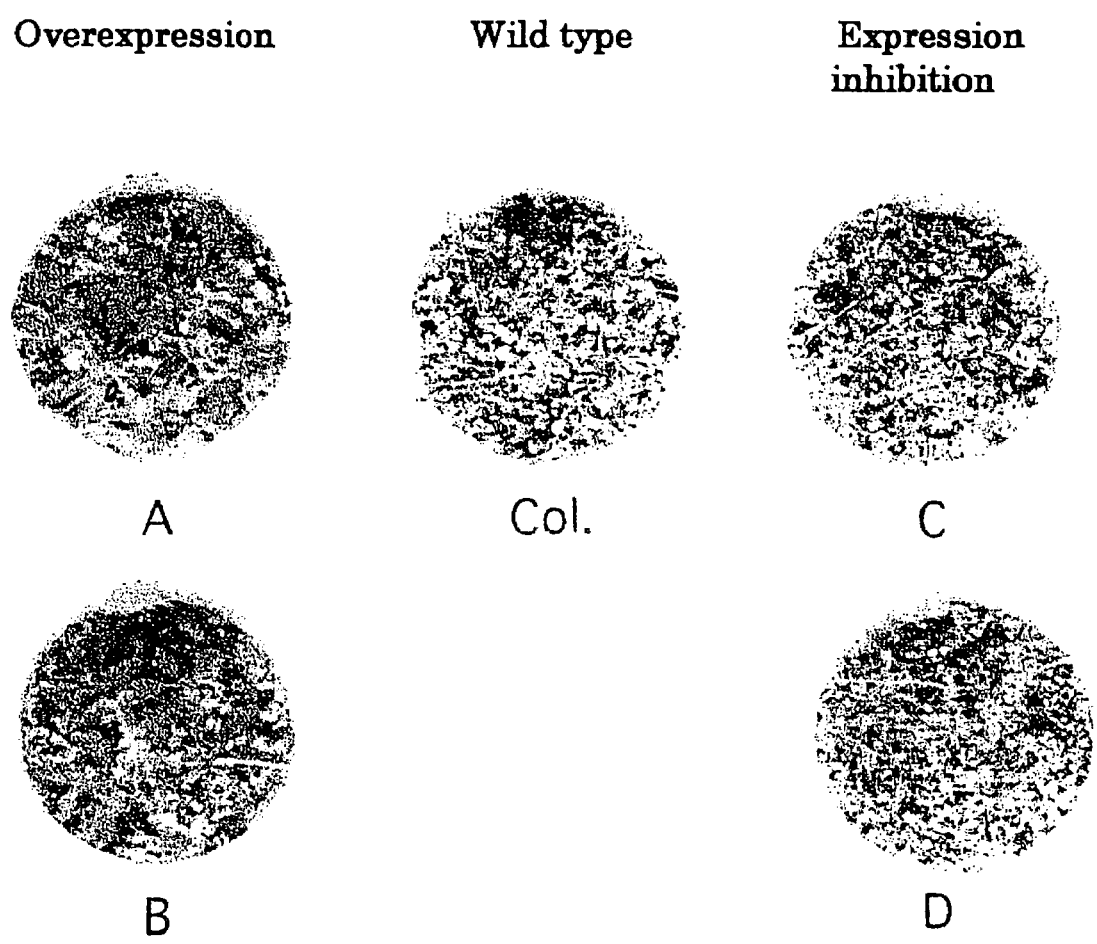
FIG. 16 shows the result of testing drought tolerance in neoxanthin cleavage enzyme transgenic plants, indicating the plants 17 days after the termination of the irrigation.

The present inventors first successfully created a transformant plant in which expression of a neoxanthin cleavage enzyme is artificially inhibited by using a gene construct which expresses an antisense RNA of a neoxanthin cleavage enzyme gene. This plant easily wilts in the non-irrigated condition compared with its wild type to show the reduced stress tolerance (FIGS. 15 and 16). In such a manner, the present inventors established a method for artificially inhibiting expression of a gene encoding a protein having a neoxanthin cleavage activity and successfully reduced stress tolerance in a plant thereby.

In the present invention, in order to reduce stress tolerance in a plant, the expression of a gene encoding a protein having a neoxanthin cleavage activity can be decreased. The term "expression" of gene used herein includes the transcription of the gene and the translation of the transcript. The inhibition of the expression includes the complete termination of the expression. To inhibit the transcription and the translation of the gene encoding a protein having a neoxanthin cleavage activity, the expression of the gene may be inhibited by targeting the DNA encoding the gene, its transcriptional control region, or the transcript of the gene.

Any plants can be used for the present invention, and various plants can be used. For example, *Arabidopsis* and such can be used. Examples of a gene encoding a protein having a neoxanthin cleavage activity, which can be a target for inhibiting the expression, are VP14 for maize (*Zea mays*) (Schwartz, S. H. et al., Science, 276: 1872-1874, 1997; Tan, B. V. et al., Proc. Natl. Acad. Sci. USA, 94: 12235-12240, 1997) (cDNA: SEQ ID NO: 13, protein: SEQ ID NO: 14), LeNCED1 for tomato (*Lycopersicon esculentum*) (Burbidge, A. et al., J. Exp. Bot., 47: 2111-2112, 1997; Burbidge, A. et al., Plant J., 17: 427-431, 1999) (cDNA: SEQ ID NO: 15, protein: SEQ ID NO: 16), AtNCED1 (cDNA: SEQ ID NO: 1, protein: SEQ ID NO: 2), AtNCED3 (cDNA: SEQ ID NO: 5, protein: SEQ ID NO: 6), and/or AtNCED5 (cDNA: SEQ ID NO: 9, protein: SEQ ID NO: 10) for *Arabidopsis*, CPRD65 (cDNA: SEQ ID NO: 11, protein: SEQ ID NO: 12) for cowpea, etc. Homologous genes derived from other plants can also be a target. Homologous genes of other plants can be identified and/or isolated by, for example, the hybridization method described above and such. For reducing stress tolerance in a given plant in the present invention, using a gene or gene sequence information of another plant species (for example, the gene above), the expression of a target gene in the desired plant can be inhibited by known methods, such as gene silencing and antisense methods. Therefore, a target gene in an objective plant is not necessarily isolated nor identified.

The expression of a gene encoding a protein having a neoxanthin cleavage activity of the present invention can be inhibited by inserting a DNA for inhibiting the expression of the gene into an appropriate vector, introducing the vector into a plant cell, and regenerating a transgenic plant from the resultant transformant cell. Any promoters can be used, for example, the promoters as described above case for improving stress tolerance. For example, use of an expression inducible type promoter can reduce stress tolerance only under a specific condition.

As a method for inhibiting the expression of a specific endogenous gene in a plant, a method using the antisense technique is used the most often by one skilled in the art.

The antisense method is an artificial gene expression inhibition method in which a double strand of a target mRNA with a DNA molecule (an antisense nucleic acid) complementary to the RNA transcribed from a given gene forms for inhibiting the expression. The gene expression inhibition method by an antisense was developed from 1960 to 1970, and in 1978, Zamecnik et al. successfully inhibited the replication and reverse transcriptase activity of chicken Rous sarcoma virus using an antisense oligomer (Zamecnik, P. C. and Stephenson, M. L., Proc. Natl. Acad. Sci. USA, 75: 280-284, 1978).

Among methods for introducing an antisense DNA, an antisense oligomer is directly administered into a cell, or transformation is conducted by ligating an antisense DNA of a target gene with an expression vector. Examples given below demonstrate the latter method. Specifically, a cDNA of a gene encoding a protein having a neoxanthin cleavage activity is ligated downstream of 35S promoter of cauliflower mosaic virus in the antisense direction to introduce the vector into a plant cell. The antisense effect in a plant cell was first demonstrated by Ecker et al. by showing the antisense effect of the antisense RNA introduced by an electroporation using a transient gene expression method in a plant (Ecker, J. R. and Davis, R. W., Proc. Natl. Acad. Sci. USA, 83: 5372, 1986). After that, inhibition of a target gene expression by an antisense RNA expression have been reported in tobacco and petunia plants (van der Krol, A. R. et al., Nature, 333: 866, 1988). At present, the antisense method is well established as a mean for inhibiting gene expression in a plant. Modes of inhibition of a target gene expression by an antisense nucleic acid include inhibition of transcription initiation by the formation of a triple strand, inhibition of transcription by the formation of a hybrid with a site at which an open loop structure is locally created by an RNA polymerase, inhibition of splicing by the formation of hybrid with an RNA in which a synthesis is occurring, inhibition of splicing by the formation of a hybrid with a spliceosome formation site, inhibition of transfer from a nucleus to a cytoplasm by the formation of a hybrid with an mRNA, inhibition of splicing by the formation of a hybrid with a capping site or a Poly(A) addition site, inhibition of translation initiation by the formation of a hybrid with a translation initiation factor binding site, inhibition of translation by the formation of a hybrid with a ribosome binding site flanking an initiation codon, inhibition of extension of a peptide strand by the formation of a hybrid with a coding region of mRNA or a polysome binding site, inhibition of gene expression by the formation of a hybrid with an interaction site between a nucleic acid and a protein, and so on. These inhibit processes of transcription, splicing, or translation to inhibit the expression of a target gene (Hirajima and Inoue, "New Biochemistry Experiment Lecture 2, Nucleic Acid IV, Replication and expression of a gene," Japanese Association of Biochemistry (eds), Tokyo-Kagakudojin, pp. 319-347, 1993).

A sequence of an antisense DNA is preferably a sequence complementary to a transcript of an endogenous gene encoding a protein having a neoxanthin cleavage activity or its part in a plant to be transformed, however, is not necessarily completely complementary as long as it effectively inhibits the gene expression. An transcribed RNA comprises preferably 90% or higher complementarity, and the most preferably 95% or higher complementarity to the transcript of a target gene. For effectively inhibiting the expression of a target gene using an antisense sequence, a length of an antisense DNA is at least 15 or more nucleotides, preferably 100 or more nucleotides, and more preferably 500 or more nucleotides. Generally, an antisense DNA to be used is shorter than 5 kb and preferably shorter than 2.5 kb.

The expression of an endogenous gene can also be inhibited by using a DNA encoding a ribozyme. Recently, the inhibition of a gene expression using a DNA encoding a ribozyme has been studied. A ribozyme is an RNA comprising an activity of catalyzing a reaction in vivo. Ribozymes have various activities. The studies of a ribozyme as an enzyme cleaving an RNA enable designing a ribozyme for the purpose of cleaving an RNA at a specific site. Ribozymes include a group I intron type, huge one of 400 or more nucleotides such as M1RNA included in RNaseP, and those called a hammer head type and hair pin type, comprising an active domain as long as 40 nucleotides (Koizumi, M., and Otsuka, E., Protein, Nucleic Acid and Enzyme, 35: 2191, 1990).

For example, a self-cleavage domain of a hammer head type ribozyme digests 3' site of C15 among G13U14C15. The formation of a base pair between U14 and A at 9th is believed to be important for this activity, and the nucleotide at 15th can be digested if it is A or U as well as C (Koizumi, M. et al., FEBS Lett., 228: 225, 1988). If a substrate binding site of a ribozyme is designed to be complementary to an RNA sequence flanking a target site, a restriction enzyme-like ribozyme which recognizes sequences of UC, UU, or UA in a target RNA can be created (Koizumi, M. et al., FEBS Lett., 239: 285, 1988; Koizumi, M., Otuska, E., Protein, Nucleic Acid and Enzyme, 35: 2191, 1990; Koizumi, M. et al., Nucleic Acids Res., 17: 7059, 1989). For example, hundreds of such sites exist in a coding region of AtNCED3 gene of *Arabidopsis*. A hairpin type ribozyme is found in, for example, a minus strand of a satellite RNA in tobacco ring spot virus (Buzayan, J. M., Nature, 323: 349, 1986). This ribozyme has also been shown to be able to be designed to specifically cleave a target RNA (Kikuchi, Y. and Sasaki, N., Nucleic Acids Res., 19: 6751, 1992; Kikuchi, H., Chemistry and Biology, 30: 112, 1992).

A ribozyme designed for cleaving a target is ligated with a promoter, for example, 35S promoter of cauliflower mosaic viruses and a transcription termination sequence, to be transcribed in a plant cell. When an extra sequence is added at 5' end or 3', end of an transcribed RNA, an activity of a ribozyme may be deleted. In this case, for accurately excising a ribozyme portion alone from a transcribed RNA containing a ribozyme, another trimming ribozyme which works cis for trimming at 5' end and 3' end of a ribozyme portion, can be placed (Taira, K. et al., Protein Eng., 3: 733, 1990; Dzianott, A. M. and Bujarski, J. J., Proc. Natl. Acad. Sci. USA., 86: 4823, 1989; Grosshans, C. A. and Cech, R. T., Nucleic Acids Res., 19: 3875, 1991; Taira, K. et al., Nucleic Acids Res., 19: 5125, 1991). In addition, such a constitutive unit is tandemly arranged to cleave multiple sites within a target gene, improving the effect (Yuyama, N. et al., Biochem. Biophys. Res. Commun., 186: 1271, 1992). By using such a ribozyme, a transcript of a target gene of this invention can be cleaved to inhibit its expression. Preferably, a ribozyme specifically cleaves a transcript of a target gene. By using such a ribozyme, a transcript of a target gene of this invention is specifically cleaved to inhibit its expression.

Inhibition of the expression of an endogenous gene can also be achieved by cosuppression due to the introduction of a DNA comprising an identical or a similar sequence to a target gene sequence. "Cosuppression" means a phenomenon in which an introduction of a gene comprising an identical or similar sequence to a target endogenous gene into a plant by transformation inhibits the expression of both an exogenous gene introduced and a target endogenous gene. Details of the mechanism of cosuppression are not clear, however, it is often observed in plants (Curr. Biol., 7: R793, 1997; Curr. Biol., 6: 810, 1996). For example, a plant in which the expression of a gene encoding a protein having a neoxanthin cleavage activity has been cosuppressed, can be obtained by preparing a vector DNA comprising a gene encoding a protein having a neoxanthin cleavage activity or a similar sequence, transforming an objective plant with the vector, and selecting among obtained plants with a trait in which the expression of a gene encoding a protein having a neoxanthin cleavage activity has been reduced.

A gene to be used for cosuppression does not need to be completely identical to a target gene, however, generally has at least 70% or higher, preferably 80% or higher, more preferably 90% or higher identity. Genetyx (Software Development), a genetic information processing software, can be used for determining an identity or complementarity. This program adopts Lipman-Pearson method (Lipman, D. J. and Pearson, W. R., Science, 227: 1435-1441, 1985). This method first compares sequence data, and calculates identity among the sequences with high homology in consideration with a deletion of a sequence (GAP).

A transformant plant with reduced stress tolerance can be prepared by using a DNA as described above to be used in the present invention that inhibits the expression of a gene. Specifically, the DNA is inserted into an appropriate vector, the vector is introduced into a plant cell, and a transgenic plant is regenerated from the transformant plant cell. As a vector to be used, any vectors can be used in the same manner as in the above case of increasing the stress tolerance as long as an inserted gene can be expressed in a plant cell. Any plant cells can be used to insert a vector. A plant can be a conifer, a broad-leaved tree, a dicot, a monocot, etc. "Plant cell(s)" referred herein include various forms of plant cells, for example, a suspended cultured cell, a protoplast, a leaf slice, a callus, and so on.

Introduction of a vector into a plant cell, and regeneration of a plant from a transformant cell, can be performed by a method known to one skilled in the art, depending on a type of plant cells in the same manner as in the case of improving stress tolerance. Once a transformant plant in which a DNA of the present invention is introduced into the genome can be obtained, offspring can be obtained from the plant by sexual or asexual propagation. Alternatively, a propagation material (for example, a seed, a fruit, a scicon, a tuber, a tuberous root, a stock, a callus, a protoplast, etc.) can be obtained from the plant, its offspring, or clones, and the plant can be mass-produced from them. The present invention includes a plant cell in which a DNA of present invention is introduced, a plant containing the cell, offspring or a clone of the plant, as well as a propagation material for the plant, its offspring, and clone.

The transformant plant created in such a manner has a reduced ABA content, compared with the wild type plant. Alternatively, the transformant plant has a decreased stress tolerance compared with the wild type plant. The present invention can be applied to, for example, a weed to effectively eliminate it. In addition, using a inducible promoter as described above, a transformant plant of the present invention can be used for land improvement and such.

The present invention enables creating a plant in which stress tolerance has been increased or decreased. A plant with the improved stress tolerance can grow in harsh land where plants cannot grow thus far. Reduction of stress tolerance can be applied to weeds and such to be eliminated. The method of the present invention can be applied to agriculture to expand cultured area and increase crop yields.

Any patents, patent applications, and publications cited herein are incorporated by reference.

The present invention is illustrated in detail below with reference to examples, but is not to be construed as being limited thereto. Experimental conditions used in the present Examples are as follows.

Growth of Cowpea

Seeds of cowpea (*Vigna unguiculata* IT84S-2246-4) were sown in pots and grown for 8 days in a greenhouse with a photoperiod of 16 hours (in addition to natural light, artificial lighting was supplemented when illumination was insufficient), temperature of 25° C., and appropriate watering.

Dehydration Treatment

For dehydration treatment, plants were pulled out of the pot carefully to avoid injury, weighed, and dehydrated on Whatman 3MM filter paper at room temperature and approximately 60% humidity under dim light (300 lux). For the control, plants were pulled out of the pot and immediately transplanted in well-watered soil that was maintained under the same condition for dehydration treatment group.

Analysis of DNA Sequence

Plasmid DNA templates were prepared using the Automatic Plasmid Isolation System Model PI-100 (KURABO) and sequenced using the DNA Sequencer Model 373A (ABI). Nucleotide sequences and amino acid sequences were analyzed using a GeneWorks Software System (IntelliGenetics, Inc.), Sequencher 3.0 (Hitachi Software), and the University of Wisconsin Genetic Computer Group (GCG) program.

EXAMPLE 1

Isolation of cDNA Clones Corresponding to Genes Induced by Dehydration

A cDNA library was constructed with poly(A)$^+$ RNA that had been isolated from 8-day-old cowpea plants after dehydration stress for 10 hours as follows.

Whole plants were harvested, washed gently to remove soil from the roots and dehydrated on Whatman 3MM filter paper at room temperature and approximately 60% humidity under dim light for 10 hours. Total RNA was prepared from the plants after dehydration treatment by the aforementioned method (Nagy, F. et al., "Analysis of gene expression in transgenic plants." In Gelvin and Schilperoort (eds), "Plant Molecular Biology Manual. B4.," Kluwer Academic Publishers, Dordrecht, pp. 1-29, 1988). By following the reference (Sambrook, J. et al., "Molecular Cloning: A Laboratory Manual," 2nd ed, Cold Spring Harbor Laboratory Press, Cold Spring Harbor, N.Y., 1989), total RNA was passed through an Oligo-dT cellulose column twice to prepare poly(A)$^+$ RNA. About 2% of the RNA applied to the column was collected as the Poly(A)$^+$ RNA fraction. Double-stranded cDNA was synthesized from the Poly (A)$^+$ RNA using cDNA Synthesis System Plus (Amersham Pharmacia Biotech). A cDNA library was constructed from the cDNA using cDNA Cloning System (Amersham Pharmacia Biotech).

The cDNA library was differentially screened with cDNA prepared from poly(A)$^+$ RNA that had been isolated from unstressed cowpea plants and with cDNA prepared from poly (A)$^+$ RNA that had been isolated from plants after dehydration stress for 10 hours. By following the reference (Sambrook, J. et al., "Molecular Cloning: A Laboratory Manual," 2nd ed, Cold Spring Harbor Laboratory Press, Cold Spring Harbor, N.Y., 1989), plaque hybridization was conducted to screen 1×10$^4$ plaques from the cDNA library.

As a result, plaques giving a stronger hybridization signal with [$^{32}$P]-labeled cDNA were obtained from 10-hour dehydrated cowpea plants. The plasmid regions of the phage clones were excised in vivo and used to transform *Escherichia coli* cells. The cDNA fragments from the resultant plasmids were analyzed using the restriction map and the border sequences of the cDNA fragments. From these analyses, cDNA was grouped, and a cDNA clone, named CPRD (CowPea Responsive to Dehydration) 65 could be identified.

Dehydration-induced expression of the gene corresponding to the CPRD65 clone was analyzed by Northern blot hybridization. The 8-day-old plants were pulled out of the soil and dehydrated for various periods up to 12 hours. As controls, similar cowpea plants were pulled out of the soil and were immediately transplanted to well-watered soil. Total RNA was then isolated from dehydrated or control plants for Northern blot hybridization.

Total RNA was isolated according to the method of Nagy et al. (Nagy, F. et al., "Analysis of gene expression in transgenic plants." In Gelvin and Schilperoort (eds), "Plant Molecular Biology Manual, B4.," Kluwer Academic Publishers, Dordrecht, pp, 1-29, 1988), fractionated in a 1% agarose gel containing formaldehyde, and transferred to a nylon filter (Sambrook, J. et al., "Molecular Cloning: A Laboratory Manual," 2nd ed, Cold Spring Harbor Laboratory Press, Cold Spring Harbor, N.Y., 1989). The nylon filter was hybridized with [$^{32}$P]-labeled CPRD65 cDNA fragments in 50% formamide, 5×SSC, 25 mM sodium phosphate buffer (pH 6.5), 10× Denhardt's solution, and 250 µg/ml of denatured salmon sperm DNA at 42° C. The filter was washed twice with 0.1×SSC, 0.1% SDS at 60° C. for 15 min, and subjected to autoradiography.

FIG. 1 shows the time course of induction of the expression that corresponds to the CPRD65 gene against dehydration treatment. The expression of CPRD65 was significantly increased by dehydration stress. The mRNA corresponding to the CPRD65 was observed to accumulate within 2 hours after the initiation of dehydration treatment.

Cowpea plants dehydrated for 10 hours appeared wilted. These wilted plants showed recovery from wilting within 4 hours after transfer to well-watered soil (rehydration treatment). After rehydration, the level of CPRD65 mRNA decreased (FIG. 1). The CPRD65 gene exhibited typical and significant responses to drought stress, namely, induction of the transcriptions by dehydration and reduction of the level upon rehydration. These facts suggested that the CPRD65 gene is involved in drought tolerance.

EXAMPLE 2

Sequence Analysis of the CPRD65 cDNA

Since the CPRD65 cDNA fragment isolated in Example 1 was not possibly full length, the same cDNA library was screened again with a partial CPRD65 cDNA as a probe to isolate a full-length cDNA (SEQ ID NO: 11). An amino acid sequence encoded by the full-length cDNA clone (SEQ ID NO: 12) was shown in FIG. 2. The full-length CPRD65 cDNA consists of 2432 bp, including a 5'-flanking region of 125 bp and 3'-flanking region of 486 bp. One polyadenylation consensus sequence (AATAAA) was found in the 3'-flanking region. This sequence has an open reading frame encoding a polypeptide of 612 amino acids with a calculated molecular weight for the putative protein of 67.6 kDa. Comparison of the deduced amino acid sequence of the CPRD65 protein with the protein database revealed an extensive homology with VP14 from maize (*zea mays*) (61%) (Schwartz, S. H., Science, 276: 1872-1874, 1997) and a neoxanthin cleavage enzyme from tomato (*Lycopersicon esculentum*) (69%), (Burbidge, A. et al., J. Exp. Bot., 47: 2111-2112, 1997; Burbidge, A. et al., Plant J., 17: 427-431, 1999) as shown in FIG. 2. The putative CPRD65 protein seems to contain a transit polypeptide in its N-terminal region like the VP14 protein. The N-terminal sequences of the CPRD65, VP14, and tomato neoxanthin cleavage enzyme have low sequence similarity, but structural similarity.

EXAMPLE 3

Genomic Southern Blot Analysis of the CPRD65 Gene

In order to analyze genes related to the CPRD65 of cowpea plants, genomic Southern blot hybridization was conduced in the conditions of two stringencies (FIG. 3).

The genomic Southern blot analysis was conducted according to the method of the reference (Sambrook, J. et al., "Molecular Cloning: A Laboratory Manual," 2nd ed, Cold Spring Harbor Laboratory Press, Cold Spring Harbor, N.Y., 1989). Genomic DNA of 10 µg was digested with restriction enzymes, separated in a 1% agarose gel, and blotted to a nylon filter. The filter was hybridized with [$^{32}$P]-labeled fragments in 30% formamide, 6×SSC, 5× Denhardt's solution, and 100 µg/ml of denatured salmon sperm DNA at 42° C. The filter was washed twice with 0.1×SSC, 0.1% SDS at 60° C. for 15 min (B), or washed twice with 0.5×SSC, 0.5% SDS at 37° C. for 15 min (A), and subjected to autoradiography.

The CPRD65 cDNA had no internal restriction site for EcoRI and XbaI and had two flanking internal restriction sites for HindIII, confirmed by its nucleotide sequence. One hybridized band in the EcoRI and XbaI digest and two hybridized bands in the Hind III digest were detected using the CPRD65 cDNA as a probe. Some additional faint hybridized bands were detected under the above stringency condition (A). These results suggest that the CPRD65 gene constitutes a small gene family with related genes.

EXAMPLE 4

Northern Blot Analysis of the CPRD65 Gene

The effects of various environmental stresses on the expression of the CPRD65 gene were analyzed. For high salinity, ABA, and water treatments, plants were pulled out of the soil in the same manner as in the dehydration treatment, and grown by the hydroculture in the solutions containing 250 mM NaCl, 100 µM ABA, and deionized water, respectively. For heat and cold treatments, potted plants were transferred to the incubators at 40° C. and 4° C., respectively. Each stress treatment to plants was conducted for 0, 1, 2, 5, 10, and 24 hours. After the treatments, the treated plants were immediately frozen with liquid nitrogen, and the RNAs were isolated for Northern blot analysis.

As a result, it was found that the expression of this gene was strongly induced under a high-salt condition, but not by cold or heat stress (FIG. 4A). The induction of the CPRD65 gene was not detected by ABA treatment or water treatment.

To determine the tissue specificity of the expression of the CPRD65 gene under drought stress, Northern blot hybridization of total RNA prepared from leaves, stems, or roots under a normal or drought condition was performed (FIG. 4B). The CPRD65 transcript was strongly induced in stems and leaves by drought treatment, but less in roots.

EXAMPLE 5

Enzymatic Activity of the Bacterially Expressed CPRD65 Protein

The deduced amino acid sequence of the CPRD65 gene has high homology with an amino acid sequence of a neoxanthin cleavage enzyme encoded by the maize VP14 gene (FIG. 2). To examine whether the CPRD65 gene encodes a neoxanthin cleavage enzyme, the biochemical properties of the recombinant CPRD65 protein expressed in *E. coli* were analyzed. A DNA fragment for the CPRD65 coding region was amplified by PCR and fused to the GST gene in frame using the pGEX4T-1 (Pharmacia) to construct a chimeric plasmid pGST-CPRD65 as follows.

The DNA encoding the CPRD65 protein was amplified by PCR using primers: 5'-ATTGAATTCATGCCTTCAGCT-TCAAAC-3' (SEQ ID NO: 19) and 5'-ATTGGATC-CCAAAAGCTACACGCTGGTCCCC-3' (SEQ ID NO: 20). The PCR fragment was inserted into the EcoRV site of pBluescript II SK$^+$ vector. Sequences of the inserted PCR fragments were confirmed to determine whether a mutation was generated in a nucleotide sequence by PCR. The PCR fragment in which any mutation was not identified in the nucleotide sequence was isolated from the pBluescript II SK$^+$ vector as a DNA fragment using restriction enzymes (EcoRI and XhoI) and inserted into the EcoRI to XhoI site of pGEX4T-1 (Amersham Pharmacia Biotech) to construct pGST-CPRD65. Cells of *Escherichia coli* strain JM109 were transformed with pGST-CPRD65 or pGEX4T-1 and cultured in L broth at 37° C. When OD$_{600}$ reached about 0.5, isopropyl β-D-thiogalactopyranoside (IPTG) was added, and incubation was continued for 12 hours at 17° C. The cells were harvested, washed, and suspended in extraction buffer [10 mM Tris-HCl (pH 8.0), 5 mM MgCl$_2$, 5% glycerol, 0.1 mM phenylmethylsulfonyl fluoride (PMSF), and 0.1 mM dithiothreitol (DTT)]. The procedures for purification of the fused protein and digestion with thrombin were performed according to the instruction manual for the GST gene fusion system (Amersham Pharmacia Biotech). The protein concentration was determined with a protein assay kit (Bio-Rad).

The GST-CPRD65 fusion protein was overexpressed in *E. coli* in the manner described above, and purified from the crude cell extract using a glutathione-Sepharose 4B. Whether this purified GST-CPRD65 recombinant protein digests cis-neoxanthin, trans-violaxanthin, and cis-violaxanthin to produce xanthoxin was examined.

The assay procedures for neoxanthin cleavage enzyme activity have been described (Schwartz, S. H. et al., Science, 276: 1872-1874, 1997). cis-Neoxanthin and trans-violaxanthin were prepared from spinach leaves. cis-violaxanthin was prepared from orange peel. The reaction mixture (100 µl) contained 100 mM Bis-Tris (pH 6.7), 0.05% Triton X-100, 10 mM ascorbic acid, 5 mM FeSO$_4$, and a protein sample. The reaction was allowed to proceed at room temperature for 1 hour. After addition of 1 ml of water, the reaction mixtures were extracted with n-hexane (1 ml×2) and then ethyl acetate (1 ml×2). The n-hexane fraction was concentrated and submitted to HPLC analysis on a column of Nucleosil 5 C$_{18}$ (150 mm length, 8 mm internal diameter (i. d.)). The column was eluted with a linear gradient between solvent A (85% ethanol) and solvent B (chloroform and methanol, 1:1) at a flow rate of 1.5 ml/min. The concentration of solvent B was increased from 10% to 50% in 25 min, and kept at 50% for 5 min. The absorbance of the eluate was monitored with a UV detector at 440 nm. The ethyl acetate fraction was purified with HPLC on a column of Nucleosil 5 C$_{18}$ (150 mm length, 8 mm i. d.). The column was eluted with 50% aqueous methanol at a flow rate of 1.5 ml/min, and the absorbance of the eluate was monitored with a UV detector at 260 nm. The predicted xanthoxin fraction was collected and submitted to GC-MS analysis. In each step, samples were shielded from light as much as possible.

GC-MS analysis was conducted as follows. An AUTO-MASS mass-spectrometer (Nippon Denshi) equipped with a 5890 gas chromatography (Hewlett Packard) was used for the analysis. The analytical conditions were as follows: ionization, EI 70 eV; column, DB-5 (15 m length; 0.25 mm i. d.; 0.25 µm film thickness; J&W Scientific); carrier gas, He (1 ml min$^{-1}$); injection temperature, 250° C.; transfer line temperature, 250° C.; and initial heating temperature, 80° C. Starting 1 min after injection, the heating temperature was increased to 200° C. at a rate of 30° C. min$^{-1}$ followed by further increment to 230° C. at a rate of 5° C. min$^{-1}$.

As shown in FIG. 5, the predicted C25-product and xanthoxin were detected in the reaction mixture with the GST- CPRD65 protein and cis-neoxanthin by HPLC analysis. The occurrence of xanthoxin was confirmed by GC-MS analysis in which ions characteristic to xanthoxin were observed. The ions and their relative intensities were: m/z 250 (4), 168 (32), 149 (77), 107 (61), and 95 (100). Xanthoxin and C25-product were not formed from trans-violaxanthin (data not shown). These results were not affected by the treatment with thrombin which separates the GST-CPRD65 recombinant protein into GST and CPRD65 portions.

EXAMPLE 6

Analysis of N Terminal Region of the CPRD65 Protein as a Transit Peptide in Protoplasts Prepared from *Arabidopsis*

The N-terminal region of the CPRD65 protein has typical structural features of transit peptides that are involved in chloroplast targeting. This structural feature of the CPRD65 protein suggests that the mature CPRD65 protein is located in plastids including chloroplasts. To analyze the role of its N-terminal region as a transit peptide, a chimeric gene 35S::CPRD65N-sGFP that encodes the N-terminal region of the CPRD65 protein (1-148) between the CaMV 35S promoter and the synthetic green florescent protein (sGFP) gene of the jellyfish *Aequorea victoria* (Chiu, W., et al., Curr. Biol., 6: 325-330, 1996) was constructed.

The DNA corresponding to the N-terminal peptide (1 to 148 amino acids) of the CPRD65 protein was amplified by PCR using primers: 5'-ATATATCTAGAATGCCTTCAT-CAGCTTCAAACACTTGG-3' (SEQ ID NO: 21) and 5'-ATATAGGATCCCTCCGGCACCGGCGC-GAAGTTCCCG-3 (SEQ ID NO: 22). The PCR fragment was inserted into the pBluescript II SK+ vector and verified to have no sequence mutation caused by PCR. The DNA fragment was inserted into the site between 35S-promoter and sGFP gene on transient expression vector (Chiu, W. et al., Curr. Biol., 6: 325-330, 1996). The preparation, DNA transfection, and incubation of the *Arabidopsis* protoplasts were performed as previously described (Abel, S. and Theologis, A., Plant J., 5: 421-427, 1994).

Figure 6:
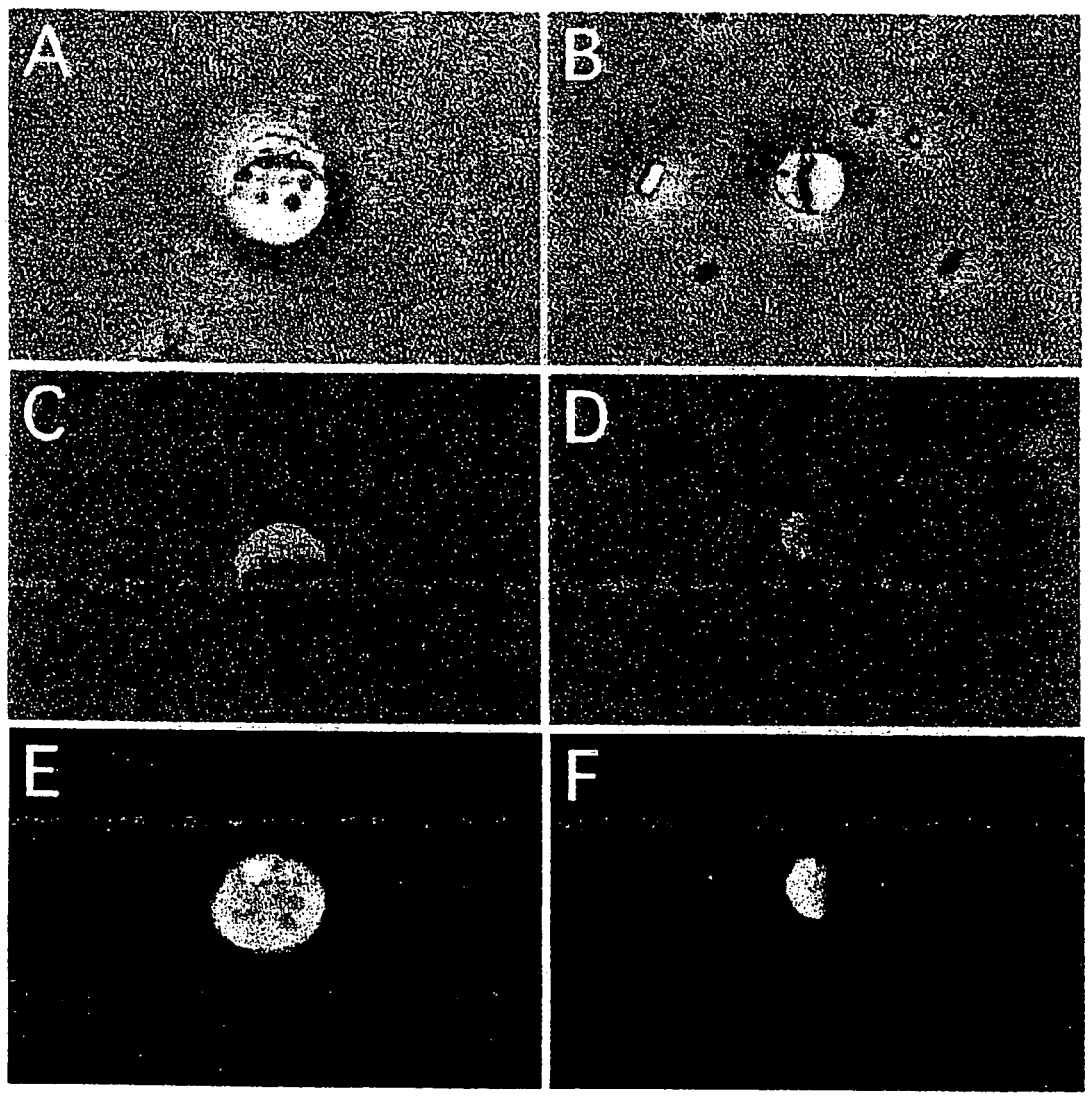
FIG. 6 shows plastid targeting of the CPRD65N-sGFP chimeric protein in protoplasts. Constructs carrying the 35S-sGFP (A, C, E) or the 35S-CPRD65N-sGFP chimeric constructs (B, D, F) were transfected into *A. thaliana* protoplasts using polyethylene glycol (PEG). Transfected protoplasts were observed by optical microscopy (A, B) or fluorescent microscopy with an interference filter type green (E, F) or red (C, D). E and F indicate GFP localization, and C and D chloroplast.

35S::CPRD65N-sGFP fusion construct and its control construct (35S::sGFP) were introduced into protoplasts prepared from *Arabidopsis* by a DNA-transfection method (Abel, S. and Theologis, A., Plant J., 5: 421-427, 1994). The protoplasts were observed by fluorescent microscopy 2 to 4 days after the transformation. As shown in FIG. 6, when 35S::CPRD65N-sGFP was transiently expressed in the protoplasts, fluorescence was localized in plastids. On the other hand, when 35S::sGFP construct was introduced, fluorescence was detected not in plastids, but mainly in the cytoplasm. These results suggest that N-terminal region of the CPRD65 protein functions as a transit peptide to target the CPRD65 protein into the plastids. The CPRD65 protein was expected to be localized in plastids, and function to produce ABA in plastids.

EXAMPLE 7

Accumulation of ABA by Dehydration Stress in 8-day-old Cowpea Plants

The accumulation of endogenous ABA level in a 8-day-old cowpea plant was measured by dehydration conditions.

Samples were homogenized in liquid nitrogen and extracted with aqueous methanol (20 to 80%) twice. After addition of [$^2H_3$]ABA, the extracts were concentrated, and submitted to a standard solvent fractionation procedure to give an acidic-ethyl acetate soluble fraction. It was purified using Bond Elut cartridge ($C_{18}$ and DEA, Varian) by the procedure reported previously (Wijayanti, L., et al., Biosci. Biotech. Biochem., 59: 1533-1535, 1995). Purified samples from undesiccated plants were then subjected to HPLC analysis with a Senshu Pak ODS-2101-N column (100 mm length, 6 mm i. d., Senshu Scientific Co.). The analytical conditions were the same as reported previously (Wijayanti, L., et al., Biosci. Biotech. Biochem., 59: 1533-1535, 1995). Samples thus purified were methylated with etherial diazomethane and submitted to GC-SIM analysis.

Figure 7:
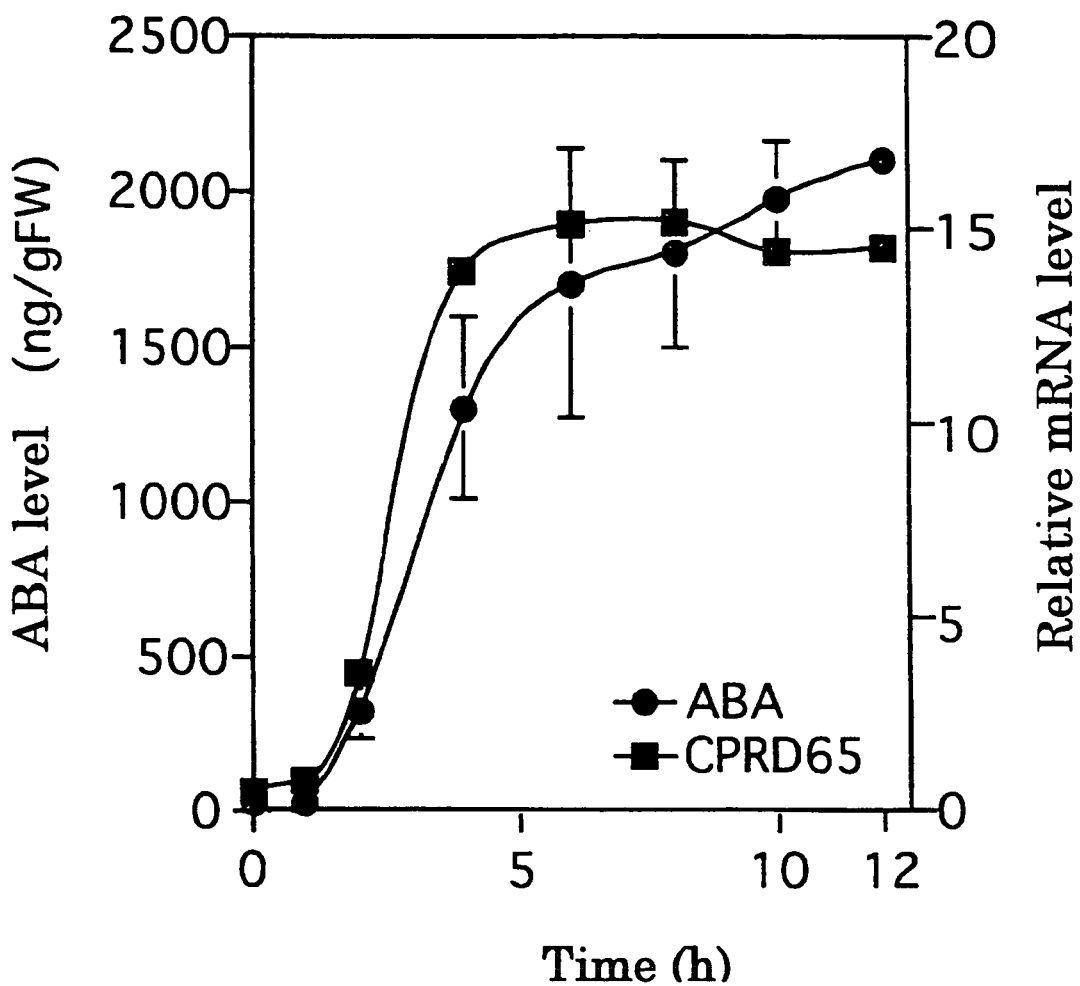
FIG. 7 shows the relationship between the accumulation of ABA and the expression of the gene for CPRD65 during dehydration. The radioactivity retained on the nylon filter in FIG. 1 was quantified and plotted as shown. The procedure for quantification of ABA is described in Examples. Error bars show standard errors. The experiment was repeated three times.

As shown in FIG. 7, ABA began to accumulate within 2 hours after dehydration. The level of ABA in 10-hour dehydrated plants was 140 times higher than that in unstressed control plants. The timing of accumulation of the CPRD65 mRNA was earlier than that of ABA mRNA accumulation (FIG. 7).

Figure 8:
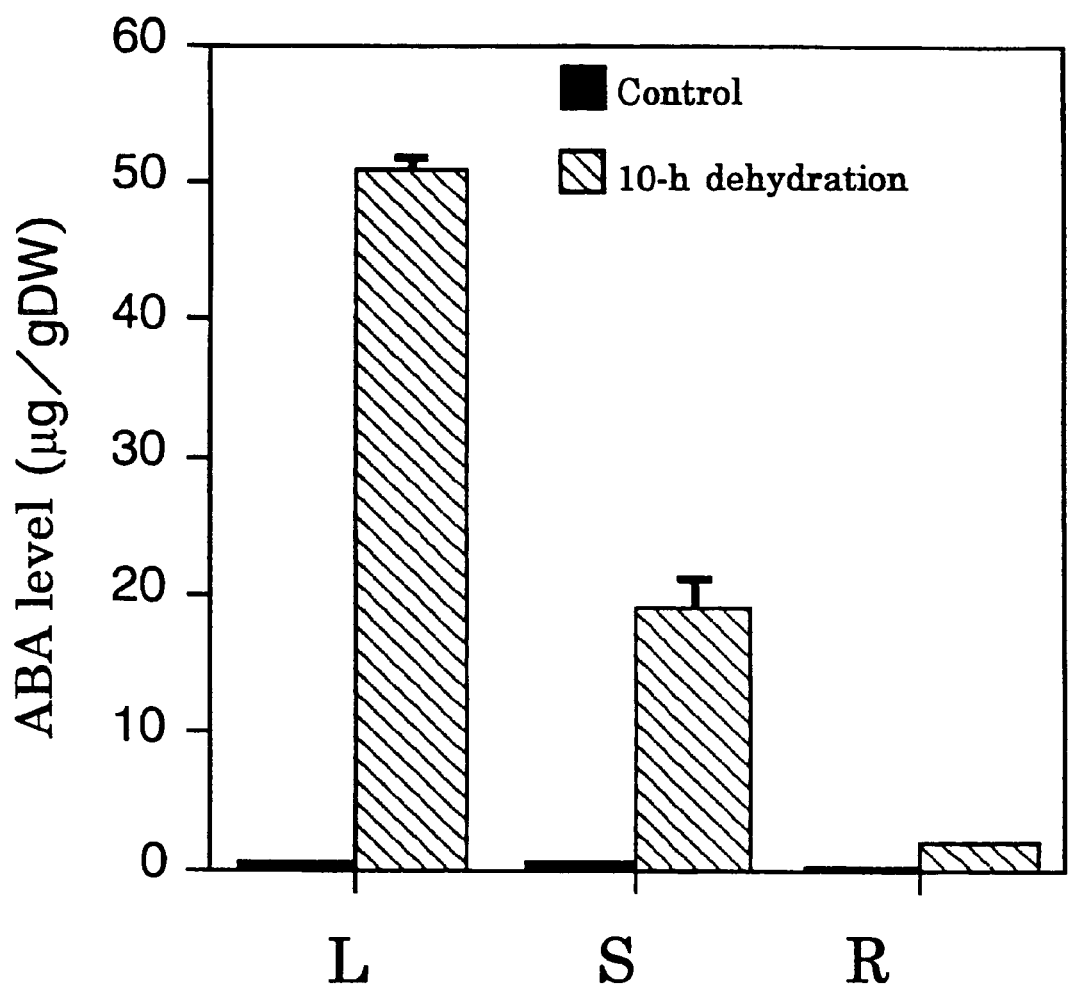
FIG. 8 shows the accumulation of endogenous ABA in leaves (L), stems (S), and roots (R) of cowpea plants during dehydration treatment after separation of organs. The procedure for quantification of ABA is the same as described in Example 7 (FIG. 7).

The expression of the CPRD65 gene was strongly induced by drought stress in leaves and stems, but slightly in roots (FIG. 4B). The relationship between the expression of the CPRD65 gene and the accumulation of endogenous ABA under drought stress was examined. The 8-day-old cowpea plants were separated into leaves, stems, and roots, and then dehydrated. The endogenous ABA levels in these organs were measured before or after dehydration treatment. As shown in FIG. 8, endogenous ABA were dramatically accumulated by drought stress in leaves and stems, but slightly in roots. The tissue-specific pattern of ABA accumulation under drought stress was consistent with that of the expression of the CPRD65 gene as shown in FIGS. 4B and 8.

EXAMPLE 8

Analysis of Xanthophylls in Cowpea Leaf

Xanthophylls in cowpea leaf were analyzed to find possible substances for the CPRD65 protein.

Samples were extracted with acetone twice, and the extracts were concentrated, dissolved in 80% methanol (1 ml), and loaded onto a Bond Elut $C_{18}$ column. The column was washed with additional 4 ml of 80% methanol, and xanthophylls were eluted with 5 ml of methanol-water-chloroform (71:9:20). The eluate was concentrated and applied to HPLC analyses with columns of Nucleosil 5 $C_{18}$ and Senshu Pak Silica-2251-S (250 mm length, 6 mm i. d.). Conditions for ODS-HPLC were the same as described above. For Silica-HPLC, a flow rate of 1.5 ml/min and a linear gradient of solvent B concentration from 10% to 100% in 30 min were used where solvent A was ethyl acetate-n-hexane (1:1) and solvent B is ethyl acetate. The xanthophylls were identified from their visible and ultraviolet spectroscopic data.

trans-Neoxanthin, trans-violaxanthin, and cis-neoxanthin were detected as major xanthophylls, and cis-violaxanthin was detected as a minor component in cowpea leaf by optical spectroscopic analysis of visible and ultraviolet lights (data not shown). The endogenous amounts of trans-neoxanthin, trans-violaxanthin, and cis-neoxanthin were not significantly different between under normal growth conditions and drought conditions.

As shown above, cowpea drought-inducible CPRD65 gene encodes the neoxanthin cleavage enzyme, and its product is localized in plastids. The CPRD65 gene was strongly induced mainly in leaves and stems under drought and high salt conditions. Strong accumulation of ABA in leaves and stems under drought conditions was observed, which showed a similar pattern of the CPRD65 gene expression. These results strongly suggest that the CPRD65 protein is an enzyme mainly-involved in the ABA biosynthesis under drought stress in cowpea plants.

EXAMPLE 9

Isolation of *Arabidopsis* cDNA Clone Encoding a Homolog of Neoxanthin Cleavage Enzyme Gene Using the CPRD65 as a probe, a cDNA library of *Arabidopsis* (Abe H. et al, Plant Cell, 9: 1859-1868, 1997) was screened. As a result, many plaques indicating strong hybridization signals were obtained. From these plaques, phage clones were isolated, and a cDNA region was excised with restriction enzymes to insert it into a pBluescript SK+ and transfect *E. coli*. By analysis of a DNA sequence, these clones were classified into one group. This was designated AtNCED3. The AtNCED3 showed a significant homology with the CPRD65 encoding a neoxanthin cleavage enzyme (FIG. 9). A nucleotide sequence of the AtNCED3 cDNA and an amino acid sequence of the AtNCED3 protein are shown in SEQ ID NOs: 5 and 6, respectively.

EXAMPLE 10

Isolation of the AtNCED1, 2, 4, and 5, and Analysis of Phylogenic Tree

Search on DNA databases using the nucleotide sequences of the CPRD65 and the AtNCED3 identified four sequences with high homology (Ac. No. AL021713, AL021687, AJ005813, AB028621).

In order to isolate a gene with high homology existing in the AL021713 sequence, a target gene fragment was amplified by the PCR method using a gDNA as a template, and 5'-CCCGGGATCCCTCAAGCCTCTCTATACCG-3' (SEQ ID NO: 23) and 5'-CCCGGGATCCTTTATACGGATTCT-GAGGGAG-3' (SEQ ID NO: 24) as primers. Using the fragment as a probe, a clone containing the target gene was isolated from the gDNA library (Clontech). The gene was amplified again by the PCR method using 5'-CCCGGGATC-CCTCAAGCCTCTCTATACCG-3' (SEQ ID NO: 23) and 5'-CCCGGGATCCTTTATACGGATTCTGAGGGAG-3' (SEQ ID NO: 24) as primers, and cloned into the EcoRV site of pBluescript II SK+ (Stratagene) to determine a nucleotide sequence. This gene was designated AtNCED1. A nucleotide sequence of the AtNCED1 cDNA and an amino acid sequence of the AtNCED1 protein are shown in SEQ ID NOs: 1 and 2, respectively.

In order to isolate a gene with high homology existing in the AL021687 sequence, a target gene fragment was amplified by the PCR method using a gDNA as a template, and 5'-ATTGAATTCATGGACTCTGTTTCTTCTTCTTCC-3' (SEQ ID NO: 25) and 5'-ATTGAATTCTTAAAGCTTAT-TAAGGTCACTTTCC-3' (SEQ ID NO: 26) as primers. Using the fragment as a probe, a clone containing the target gene was isolated from the gDNA library (Clontech). The gene was amplified again by the PCR method using 5'-AT-TGAATTCATGGACTCTGTTTCTTCTTCTTCC-3' (SEQ ID NO: 25) and 5'-ATTGAATTCTTAAAGCTTATTAAG-GTCACTTTCC-3' (SEQ ID NO: 26) as primers, and cloned into the EcoRV site of pBluescript II SK+ (Stratagene) to determine a nucleotide sequence. This gene was designated AtNCED2. A nucleotide sequence of the AtNCED2 cDNA and an amino acid sequence of the AtNCED2 protein are shown in SEQ ID NOs: 3 and 4, respectively.

In order to isolate a gene with high homology existing in the AJ005813 sequence, a target gene fragment was amplified by the PCR method using a gDNA as a template, and 5'-AA-GAATTCATGGCGGAGAAACTCAGTGATGGCAGC-3' (SEQ ID NO: 27) and 5'-AAAAGAATTCGGCTTATATAA-GAGTTTGTTCCTGG-3' (SEQ ID NO: 28) as primers. Using the fragment as a probe, a clone containing the target gene was isolated from the cDNA library (Clontech). The gene was amplified again by the PCR method using 5'-AA-GAATTCATGGCGGAGAAACTCAGTGATGGCAGC-3' (SEQ ID NO: 27) and 5'-AAAAGAATTCGGCTTATATAA-GAGTTTGTTCCTGG-3' (SEQ ID NO: 28) as primers, and cloned into the EcoRV site of pBluescript II SK+ (Stratagene) to determine a nucleotide sequence. This gene was designated AtNCED4. A nucleotide sequence of the AtNCED4 cDNA and an amino acid sequence of the AtNCED4 protein are shown in SEQ ID NOs: 7 and 8, respectively.

In order to isolate a gene with high homology existing in the AB028621 sequence, DNA was isolated from P1 clone MUJ8. The gene was amplified by the PCR method using 5'-CGGGATCCATGCAACACTCTCTTCGT-TCTGATCTTCTTC-3' (SEQ ID NO: 29) and 5'-CGG-GATCCTCAGAAAACTTGTTCCTTCAACT-GATTCTGC-3' (SEQ ID NO: 30) as primers, and cloned into the EcoRV site of pBluescript II SK+ (Stratagene) to determine a nucleotide sequence. This gene was designated AtNCED5. A nucleotide sequence of the AtNCED5 cDNA and an amino acid sequence of the AtNCED5 protein are shown in SEQ ID NOs: 9 and 10, respectively.

Figure 11:
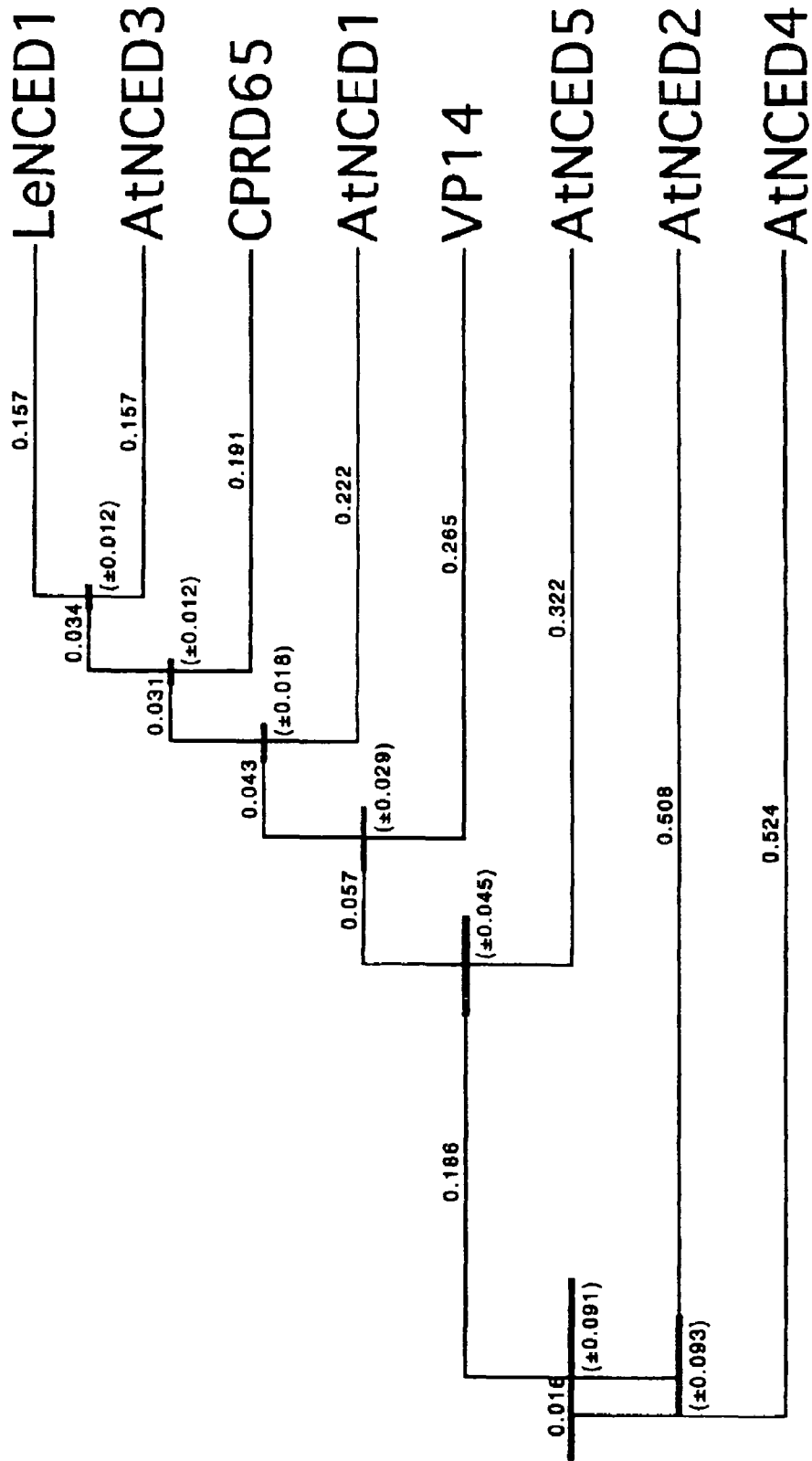
FIG. 11 shows the result of the phylogenic analysis to examine relationship between the amino acid sequences of AtNCED1, 2, 3, 4, 5, and CPRD65, and their related sequences on the databases. LeNCED1 (Ac. No. Z97215) and VP14 (Ac. No. U95953) show the proteins derived from tomatoes and maize, respectively.

FIG. 10 shows the alignments of the amino acid sequences of the AtNCED1 to 5. To examine relationship between amino acid sequences deduced from each sequence and sequences on the databases, the phylogenic tree analysis was conducted (FIG. 11). A phylogenic tree was constructed using GeneWorks (Intelligenetics, Inc.), a software for analyzing genes. Algorithm used UPGMA (Unweighted Pair Group Method with Arithmetic Mean: Molecular Evolutionary genetics, written by Nei, M., translated by Gojo, H. and Saito N., Baifukan, pp. 252-256, Japan).

EXAMPLE 11

Northern Blot Analysis of the AtNCED Genes

Effects of various environmental stresses on the expression of each identified AtNCED gene were analyzed by Northern blot analysis.

Plants grown on an agar plate for three weeks were used for each stress treatment. For dehydration stress, plants were pulled out of an agar medium, and air-dried on filter paper (relative humidity 50%). For salt stress, ABA treatment, and water treatment as a control, plants were pulled out and placed in a Petri dish containing 250 mM NaCl solution, 100 µM ABA solution, and distilled water, respectively, so that only roots were immersed, for a certain period of time at room temperature with a lid closed. For cold and heat stresses, agar plates were placed in a constant-temperature incubator at 4° C. and 40° C., respectively, for a certain period of time.

The plants treated with each environmental stress above were crushed in liquid nitrogen, total RNA was extracted (Nagy F, Kay S A and Chua N-H (1988) Analysis of gene expression in transgenic plants. In Gelvin and Schilperoort (eds), Plant Molecular Biology Manual, B4. Kluwer Academic Publishers, Dordrecht, pp 1-29), and 20 μg each of samples were loaded on each lane of a 1% agarose gel and electrophoresed. The RNA was blotted from the gel to a nylon membrane after the electrophoresis, and subjected to Northern hybridization using a [$^{32}$P]-labeled cDNA probe (Sambrook, J., Fritsch E F and Maniatis T (1989) Molecular Cloning: A Laboratory manual, 2nd ed, Cold Spring Harbor Laboratory Press, Cold Spring Harbor, N.Y.).

Figure 12:
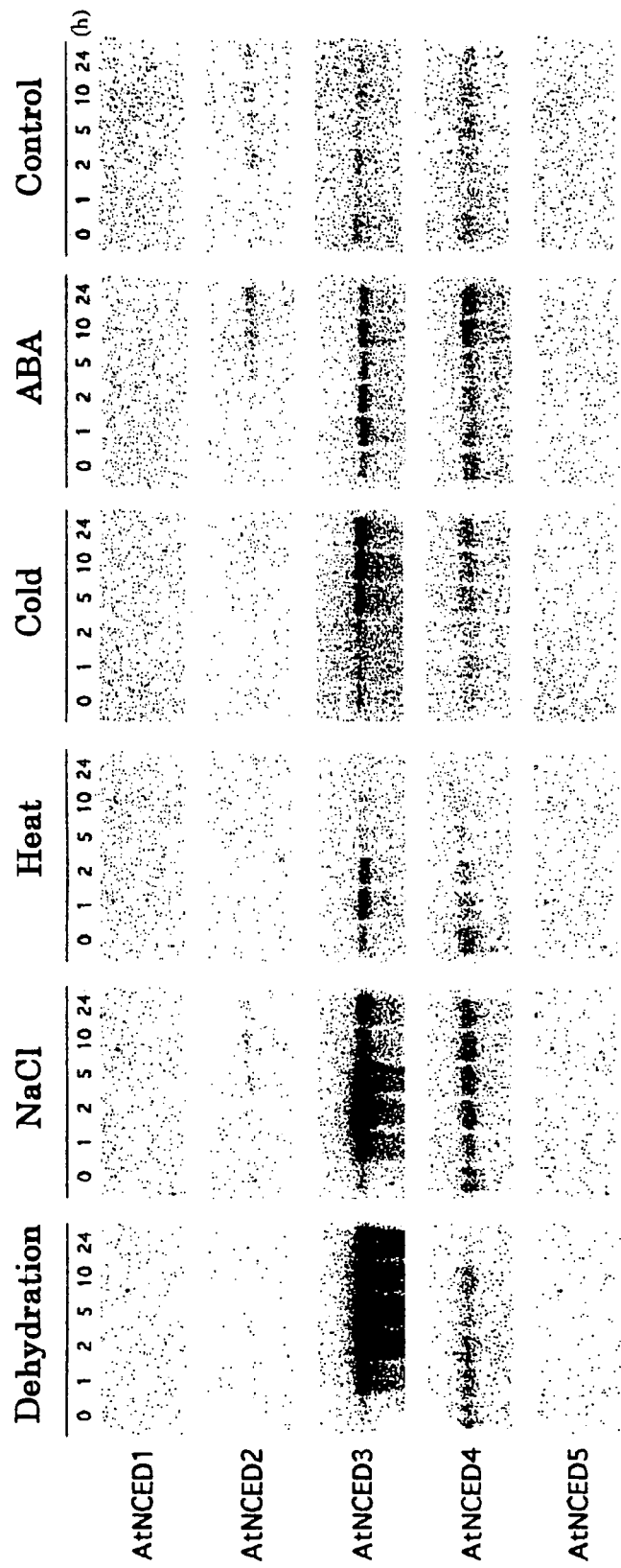
FIG. 12 shows the expression of the AtNCED genes against each stress.

As a result, it was found the AtNCED3 gene expression was strongly induced by drought, high salt concentration, and cold condition. Heat condition did not induce the expression. In addition, for ABA treatment or water treatment, the induction of the AtNCED3 gene expression was not detected (FIG. 12).

EXAMPLE 12

Enzymatic Properties of the Bacterially Expressed AtNCED Protein

The deduced amino acid sequence of the AtNCED3 gene has high homology with that of the cowpea CPRD65 gene encoding a neoxanthin cleavage enzyme (FIG. 9). To examine whether the AtNCED3 gene encodes a neoxanthin cleavage enzyme, the biochemical properties of the recombinant AtNCED3 protein expressed in *E. coli* were analyzed.

The DNA encoding the AtNCED3 protein was amplified by PCR using the cloned AtNCED3 cDNA as a template, and 5'-ATTGAATTCATGGCTTCTTTCACGGCAACGGC-3' (SEQ ID NO: 31 and 5'-GTTTTCCCAGTCACGAC-3' (SEQ ID NO: 32) as primers. The PCR fragment was cloned into the EcoRV site of pBluescript II SK$^+$ (Stratagene). Sequences of the inserted PCR fragments were confirmed to determine whether a mutation was generated in a nucleotide sequence by PCR. The DNA fragment in which any mutation was not identified was cloned in frame into the EcoRI site of pGEX4T-1 containing glutathione S-transferase (GST) gene (Amersham Pharmacia Biotech) to construct chimeric plasmid pGST-AtNCED3. Cells of *Escherichia coli* strain JM109 were transformed with pGST-AtNCED3 or pGEX4T-1 and cultured in L broth at 37° C. When CD$_{600}$ reached about 0.5, isopropyl β-D-thiogalactopyranoside (IPTG) was added, and incubation was continued for 12 hours at 17° C. The *E. coli* cells were harvested, washed, and suspended in extraction buffer [10 mM Tris-HCl (pH 8.0), 5 nM MgCl$_2$, 5% glycerol, 0.1 mM phenylmethylsulfonyl fluoride (PMSF), and 0.1 mM dithiothreitol (DTT)]. The procedures for purification of the fused protein and digestion with thrombin were performed using glutathione-Sepharose 4B [the GST gene fusion system (Amersham Pharmacia Biotech)] according to its instruction manual. The protein concentration was determined with a protein assay kit (Bio-Rad, CA, USA).

As a result of assays for the neoxanthin cleavage enzyme activity, expected C25 product and xanthoxin were detected in the reaction mixture containing GST-AtNCED3 protein and cis-neoxanthin, confirming that the AtNCED3 protein comprises a neoxanthin cleavage activity. The similar experiment detected a neoxanthin cleavage activity in the AtNCED1 and AtNCED5.

EXAMPLE 13

Preparation of Transgenic Plants

*Arabidopsis* (*Arabidopsis thaliana* (L.) Heynh. ecotype Columbia) was used as a sample. Wild type *Arabidopsis* plants were sown in a 9 cm-diameter plastic-pot with culture soil, grown for 6 weeks at 22° C. with a photoperiod of 16-hours, and then used for transformation.

A vector without a GUS reporter gene (pBE2113NOT) was constructed from a pBE2113 vector with a kanamycin resistant marker and a 35S promoter of cauliflower mosaic virus (Mitsuhara, I. et al., Plant Cell Physiol., 37: 49-59, 1996), and the cDNA of the AtNCED3 isolated from *Arabidopsis* was ligated to the vector at BamHI site in the right direction (a sense direction) or the opposite (an antisense direction). The obtained vectors were introduced into a soil bacterium (*Agrobacterium tumefaciens* strain GV3101 (pMP90)) by mixing the vectors with the bacterium. The *Agrobacterium tumefaciens* with the target gene was selected by kanamycin (Km) resistance, and infected wild type *Arabidopsis* plants using the vacuum infiltration method (Bechtold, N. et al., C. R. Acad. Sci. Paris, Life Sci., 316: 1194-1199, 1993). From the infected plants, dry seeds were harvested, sown on an agar plate supplemented with Km, and grown to select individuals of the transformant first generation (T1). Seeds of transformant second generation (T2) obtained from the transformant first generation were sown on an agar plate supplemented with Km, and grown to collect seeds for the third generation (T3) from plants showing Km resistance. Moreover, seeds of the third generation were sown on a plate supplemented with Km in the similar manner, and those of all seeds showing drug resistance were used for the following experiments as a T3 homologous line. Finally, two lines for each sense and antisense transformant of the AtNCED3 gene were isolated.

EXAMPLE 14

Evaluation of the Expression of the AtNCED3 Gene in Transformants

The expression of the AtNCED3 gene in wild type *Arabidopsis* and AtNCED3 gene-transformant plants was evaluated by Northern hybridization method.

Plants cultivated for a month were used for analyses of the AtNCED3 gene expression in transformants. The plants were pulled out and air-dried on filter papers as drought stress (relative humidity 50%). Plants that bore the environmental stress treatment above were broken in liquid nitrogen to extract total RNA (Nagy, F., Kay, S. A. and Chua, N. -H. (1988) Analysis of gene expression in transgenic plants. In Gelvin and Schilperoort, eds, Plant Molecular Biology Manual, B4. Kluwer Academic Publishers, Dordrecht, pp 1-29). The RNA was electrophoresed (20 μg per lane) on 1% agarose gel, transferred from the electrophoresed gel onto a nylon membrane, and subjected to Northern hybridization by using a [$^{32}$P]-labeled RNA probe (Sambrook, J., Fritsch, E. F. and Maniatis, T. (1989) Molecular Cloning: A Laboratory Manual, 2nd ed, Cold Spring Harbor Laboratory Press, Cold Spring Harbor, N.Y.).

Figure 13:
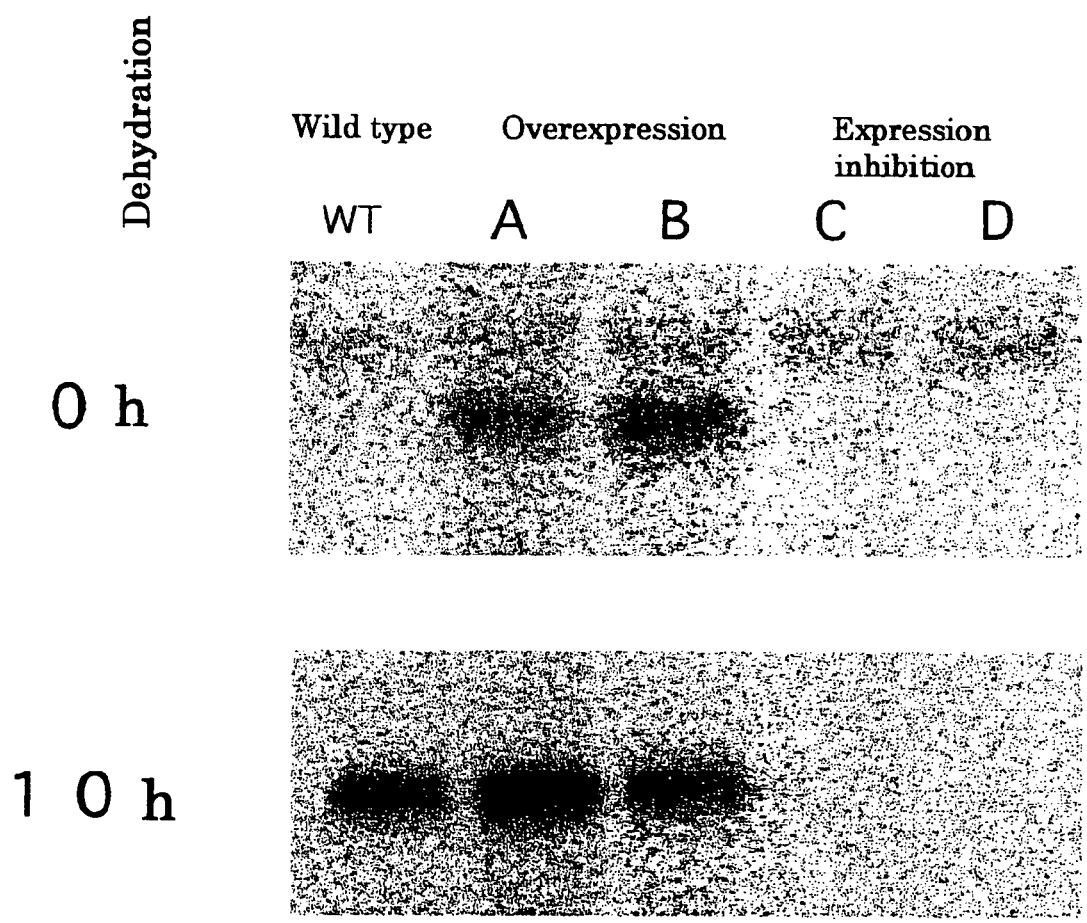
FIG. 13 shows the expression of the AtNCED3 gene in AtNCED3-transformants. The upper and lower panels show the expression of the AtNCED3 gene in plants before drought and after drought stress treatment, respectively. Two strains were used for both of plants expressing the sense AtNCED3 gene (overexpression) (A and B) and plants expressing the antisense (expression inhibition) (C and D).

As a result, the AtNCED3 gene was not expressed in the wild type before the drought stress but already expressed in the sense plants. On the other hand, after the drought treatment, the AtNCED3 gene was induced to express by drought in the wild type plants but not expressed in the antisense plants even after the drought stress treatment (FIG. 13).

EXAMPLE 15

Evaluation of Endogenous ABA Amount in Transformants

Endogenous ABA amounts were measured in wild type *Arabidopsis* and AtNCED3 gene-transformant plants.

Plants cultivated for a month were used for evaluation of endogenous ABA amounts in wild type *Arabidopsis* and transformants. Samples were homogenized in liquid nitrogen and extraction with aqueous methanol (20 to 80%) was performed twice. After adding [$^2$H$_3$] ABA, extracts were concentrated, and acidic-ethyl acetate soluble fractions were obtained by a standard solvent fractionation. These fractions were purified using Bond Elut cartridge (C$_{18}$ and DEA, Varian) by following the method described in Wijayanti, L. et al., Biosci. Biotech. Biochem., 59: 1533-1535, 1995. Samples purified from undehydrated plants were analyzed using Senshu Pak ODS-2101-N column (100 mm length, 6 mm i. d.) (Senshu Scientific Co.) by HPLC. Analytic conditions were the same as described in Wijayanti, L. et al., Biosci. Biotech. Biochem., 59: 1533-1535, 1995. Purified samples were methylated by etherial diazomethane and analyzed by GC-SIM.

Figure 14:
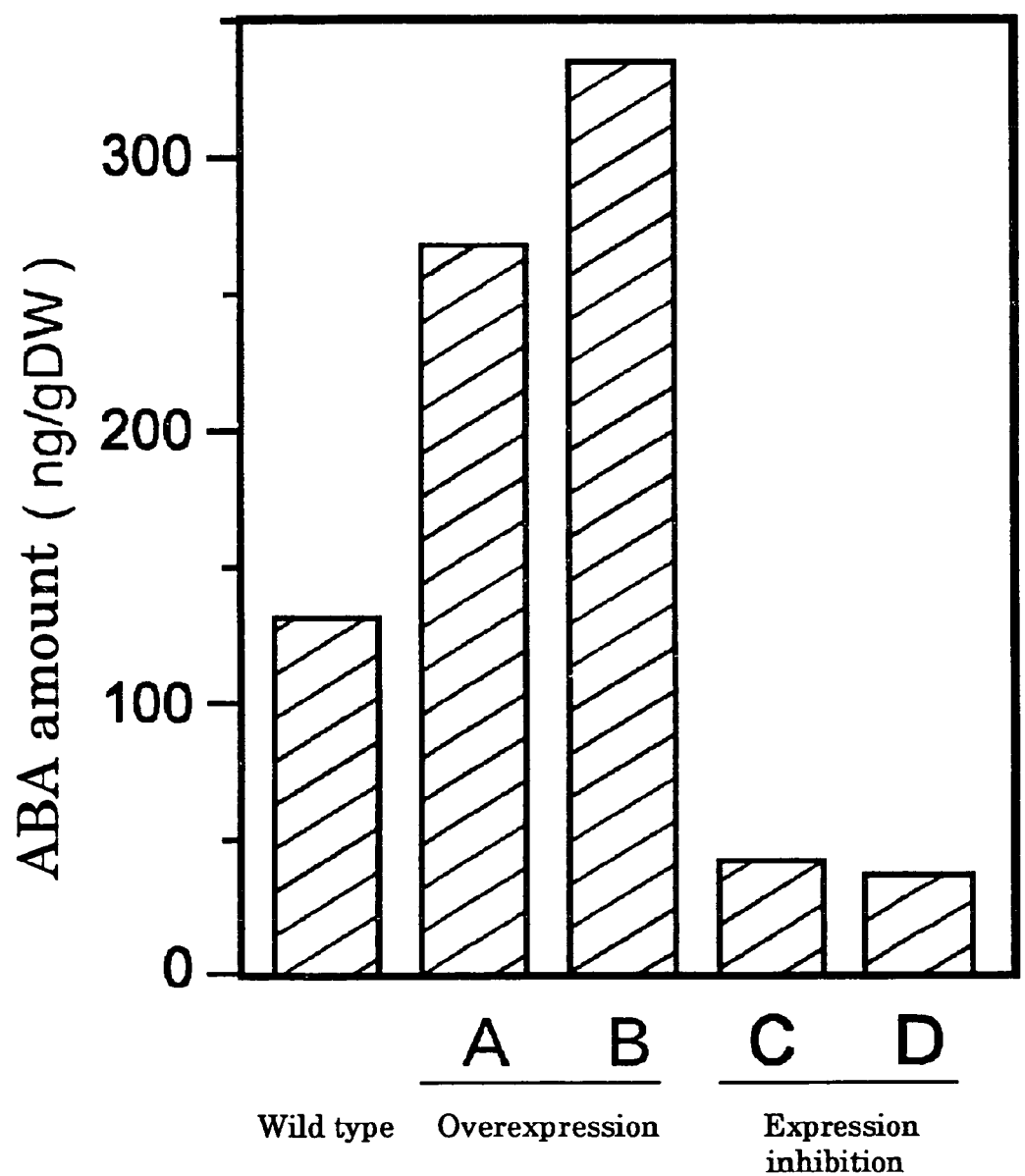
FIG. 14 shows endogenous ABA amounts in AtNCED3-transformants. Endogenous ABA amounts increased in plants expressing the sense AtNCED3 gene (overexpression) (A and B) but decreased in those expressing the antisense (expression inhibition) (C and D), compared with wild type plants.

As a result, the ABA amount increased in the sense plant compared with its wild type and decreased in the antisense plant (FIG. 14).

EXAMPLE 16

Results of Evaluation of Drought Tolerance

The seeds of the obtained transformant plants were sown on an agar plate supplemented with nutritive salts (Valvekens, D. et al., Proc. Natl. Acad. Sci. USA, 85: 5536-5540, 1988), and grown under the above growing condition for two weeks to subject to the following experiment.

Four individuals of the above plants were transplanted to plastic pots with a diameter of 9 cm filled with the soil (vermiculite:perlite=1:1) and grown under the condition with temperature of 22° C. and a photoperiod of 16 hours. Three weeks after sowing seeds (two weeks after the transplantation), the pots with the plants were dehydrated by stopping watering to naturally give drought stress. Fourteen days and 17 days after the initiation of non-irrigation, the pictures of the plants were taken. The plants in which the AtNCED3 gene was introduced in the antisense direction wilted 14 days after the initiation of non-irrigation (FIG. 15). In contrast, the transformant plants in which the gene was introduced in the sense direction seldom wilted. The wild lines also wilted 17 days after the initiation of non-irrigation, while the transformant plants in which the gene was introduced in the sense direction showed significant tolerance to drought (FIG. 16).

What is claimed is:

1. An isolated DNA encoding a protein having neoxanthin cleavage activity, wherein said protein is selected from the group consisting of:
   (a) a protein comprising the amino acid sequence of SEQ ID NO:12;
   (b) a protein encoded by a polynucleotide that hybridizes under highly stringent conditions with a DNA comprising the nucleotide sequence of SEQ ID NO:11, wherein said highly stringent conditions are: hybridization in a solution containing 30% formamide, 6X SSC, 5X Denhardt's solution, and 100 μg/ml denatured salmon sperm DNA at 37° C. and washing in 0.1X SSC, 0.1% SDS at 60° C. for 15 min; and
   (c) a protein comprising an amino acid sequence that is at least 95% identical to the sequence set forth in SEQ ID NO:12.

2. A transformed plant cell into which the DNA of claim 1 was introduced by inserting the DNA into a vector, and introducing the vector into a plant cell.

3. A transgenic plant comprising the transformed plant cell of claim 2.

4. A transgenic plant which is an offspring or a clone of the transgenic plant of claim 3.

5. The transgenic plant of claim 3, wherein the expression of the DNA encoding a protein having neoxanthin cleavage activity is increased or decreased compared to the expression level in the wild type of said transgenic plant.

6. The transgenic plant of claim 3, wherein the amount of abscisic acid is increased or decreased compared to the wild type of said transgenic plant.

7. The transgenic plant of claim 3, wherein stress tolerance to drought, high salt, or low temperature is increased compared to the wild type of said transgenic plant.

8. A transgenic propagation material for the transgenic plant of claim 3.

9. A vector comprising the DNA of claim 1.

10. A method for producing the transgenic plant comprising the DNA of claim 1, comprising the steps of introducing the DNA of into a plant cell and regenerating a plant from the plant cell.

11. A method for increasing stress tolerance to drought, high salt, or low temperature in a plant compared to a wild type of the plant, comprising expressing the DNA of claim 1 in a plant cell.

12. The isolated DNA of claim 1, wherein said isolated DNA encodes a protein that is at least 99% identical to the amino acid sequence of SEQ ID NO:12.

13. The isolated DNA of claim 1, wherein said isolated DNA comprises a nucleotide sequence that is at least 95% identical to SEQ ID NO:11.

14. An isolated DNA encoding a protein having neoxanthin cleavage activity, wherein said protein comprises the amino acid sequence of SEQ ID NO:12.

15. The method according to claim 11, wherein the DNA encodes a protein having neoxanthin cleavage activity and said protein is selected from the group consisting of:
   (a) a protein comprising the amino acid sequence of SEQ ID NO:12;
   (b) a protein encoded by a DNA that hybridizes under highly stringent conditions with the nucleotide sequence of SEQ ID NO:11, wherein said highly stringent conditions are: hybridization in a solution containing 30% formamide, 6X SSC, 5X Denhardt's solution, and 100 μg/ml denatured salmon sperm DNA at 37° C. and washing in 0.1X SSC and 0.1% SDS at 60° C. for 15 min; and
   (c) a protein comprising an amino acid sequence that is at least 95% identical to SEQ ID NO:12.

16. A transformed plant cell into which the DNA of claim 14 was introduced by inserting the DNA into a vector, and introducing the vector into a plant cell.

17. A transgenic plant comprising the transformed plant cell of claim 16.

18. A transgenic plant which is an offspring or a clone of the transgenic plant of claim 17.

19. A transgenic propagation material for the transgenic plant of claim 17.

20. A vector comprising the DNA of claim 14.

21. A method for producing the transgenic plant comprising the DNA of claim 14, comprising the steps of introducing the DNA of into a plant cell and regenerating a plant from the plant cell.

22. A method for increasing stress tolerance to drought, high salt, or low temperature in a plant compared to a wild type of the plant, comprising expressing the DNA of claim 14 in a plant cell.

* * * * *